(12) United States Patent
King et al.

(10) Patent No.: US 8,841,301 B2
(45) Date of Patent: Sep. 23, 2014

(54) SELECTIVE NR2B ANTAGONISTS

(71) Applicant: Bristol-Myers Squibb Company, Princeton, NJ (US)

(72) Inventors: Dalton King, Hamden, CT (US); John E. Macor, Guilford, CT (US); Richard E. Olson, Orange, CT (US); Christiana I. Iwuagwu, Hamden, CT (US); George N. Karageorge, Portland, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/625,015

(22) Filed: Sep. 24, 2012

(65) Prior Publication Data

US 2013/0079338 A1    Mar. 28, 2013

Related U.S. Application Data

(60) Provisional application No. 61/539,113, filed on Sep. 26, 2011.

(51) Int. Cl.
| | | |
|---|---|---|
| C07D 403/12 | (2006.01) | |
| C07D 413/12 | (2006.01) | |
| A61K 31/536 | (2006.01) | |
| A61K 31/4709 | (2006.01) | |

(52) U.S. Cl.
USPC ...... 514/252.02; 514/275; 514/272; 514/312; 544/332; 544/331; 544/296; 544/238

(58) Field of Classification Search
USPC ............. 514/312, 275, 272, 252.02; 544/332, 544/331, 296, 238
See application file for complete search history.

(56) References Cited

U.S. PATENT DOCUMENTS

| 6,316,474 | B1 | 11/2001 | McCauley et al. |
| 7,253,286 | B2 | 8/2007 | Funahashi et al. |
| 7,893,075 | B2 * | 2/2011 | Zhang et al. ................ 514/275 |
| 2004/0204341 | A1 | 10/2004 | Allen et al. |
| 2005/0245530 | A1 | 11/2005 | Borzilleri et al. |
| 2006/0128734 | A1 | 6/2006 | Floersheimer et al. |
| 2008/0090856 | A1 | 4/2008 | Flynn et al. |
| 2008/0255155 | A1 | 10/2008 | Raeppel et al. |
| 2008/0312192 | A1 | 12/2008 | Bold et al. |
| 2009/0124645 | A1 * | 5/2009 | Sorensen et al. ............ 514/272 |
| 2009/0149467 | A1 | 6/2009 | Dinsmore et al. |
| 2009/0253710 | A1 | 10/2009 | Liotta et al. |
| 2010/0029610 | A1 | 2/2010 | Singh et al. |
| 2010/0190804 | A1 | 7/2010 | Combs et al. |
| 2011/0159019 | A1 | 6/2011 | Tanaka et al. |
| 2012/0009151 | A1 | 1/2012 | Han et al. |
| 2013/0085138 | A1 | 4/2013 | King et al. |

FOREIGN PATENT DOCUMENTS

| EP | 2 325 175 | 5/2011 |
| WO | WO 2006/017409 | 2/2006 |
| WO | WO 2007042571 A1 * | 4/2007 |
| WO | WO 2009/104990 | 8/2009 |

OTHER PUBLICATIONS

Wermuth, C.G., Chapter 13: "Molecular Variations Based on Isosteric Replacements", The Practice of Medicinal Chemistry, pp. 203-237, Academic Press Limited, publ. (1996).

* cited by examiner

Primary Examiner — Kahsay Habte
(74) Attorney, Agent, or Firm — James Epperson

(57) ABSTRACT

The disclosure generally relates to compounds of formula I, including their salts, as well as compositions and methods of using the compounds. The compounds are ligands, antagonists of the NR2B receptor and may be useful for the treatment of various disorders of the central nervous system.

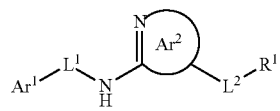

10 Claims, No Drawings

SELECTIVE NR2B ANTAGONISTS

CROSS-REFERENCE TO RELATED APPLICATIONS

This application claims the benefit of U.S. provisional application Ser. No. 61/539,113 filed Sep. 26, 2011.

BACKGROUND OF THE INVENTION

The disclosure generally relates to compounds of formula I, including their salts, as well as compositions and methods of using the compounds. The compounds are ligands for the NR2B NMDA receptor and may be useful for the treatment of various disorders of the central nervous system.

N-Methyl-D-aspartate (NMDA) receptors are ion channels which are gated by the binding of glutamate, an excitatory neurotransmitter in the central nervous system. They are thought to play a key role in the development of a number of neurological diseases, including depression, neuropathic pain, Alzheimer's disease, and Parkinson's disease. Functional NMDA receptors are tetrameric structures primarily composed of two NR1 and two NR2 subunits. The NR2 subunit is further subdivided into four individual subtypes: NR2A, NR2B, NR2C, and NR2D, which are differentially distributed throughout the brain. Antagonists of NMDA receptors, in particular NR2B, have been investigated as therapeutic agents for the treatment of major depressive disorder (G. Sanacora, 2008, Nature Rev. Drug Disc. 7: 426-437).

The NR2B receptor may be characterized by agonist binding sites in addition to that for glutamate. Non-selective NMDA antagonists such as Ketamine are pore blockers, interfering with the transport of $Ca^{++}$ through the channel. Ketamine has demonstrated rapid and enduring antidepressant properties in human clinical trials as an i.v. drug. Additionally, efficacy was maintained with repeated, intermittent infusions of Ketamine (Zarate et al., 2006, Arch. Gen. Psychiatry 63: 856-864). This class, though, has limited therapeutic value because of its CNS side effect profile which includes dissociative effects.

An allosteric, non-competitive binding site has also been identified in the N-terminal domain of NR2B. Agents which bind selectively at this site, such as Traxoprodil, exhibited a sustained antidepressant response and improved side effect profile in human clinical trials as an i.v. drug (Preskorn et al., 2008, J. Clin. Psychopharmacol., 28: 631-637, and F. S. Menniti, et al., 1998, CNS Drug Reviews, 4, 4, 307-322). However, development of drugs from this class has been typically hindered by low bioavailability and poor pharmacokinetics. Thus, in the treatment of major depressive disorder, there remains an unmet clinical need for the development of effective NR2B-selective antagonists which have a favorable tolerability profile.

NR2B receptor antagonists have been disclosed in PCT publication WO 2009/006437.

The invention provides technical advantages, for example, the compounds are novel and are ligands for the NR2B receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders related to levels of tachykinins or serotonin or both.

One aspect of the invention is a compound of formula I

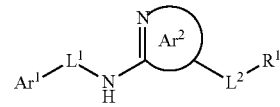

where:

$R^1$ is selected from the group consisting of

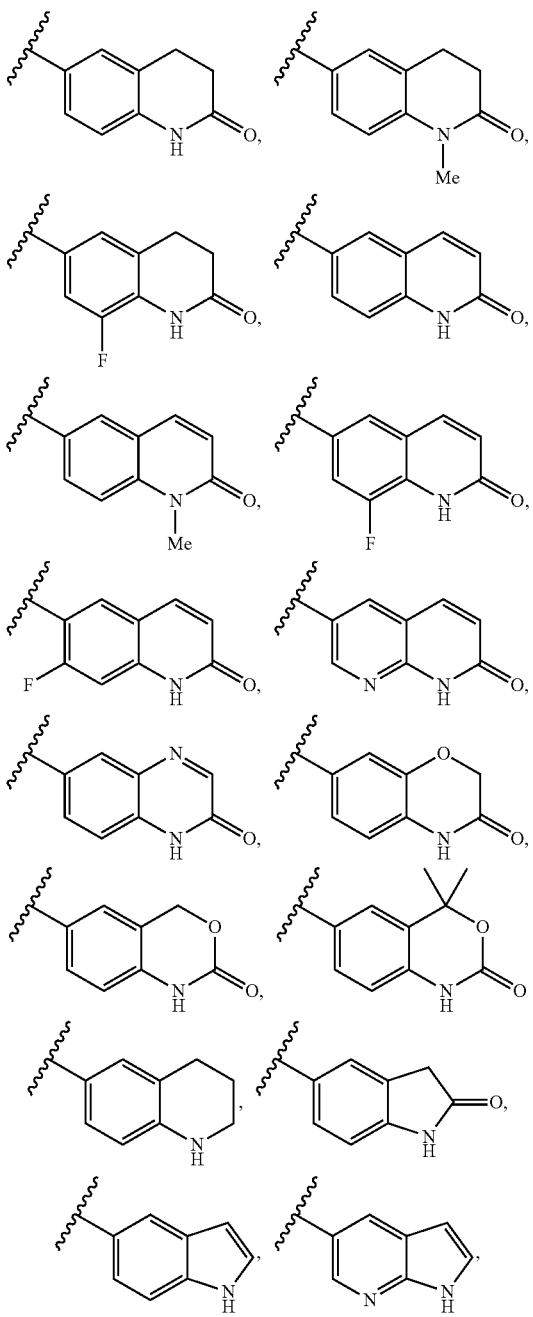

-continued

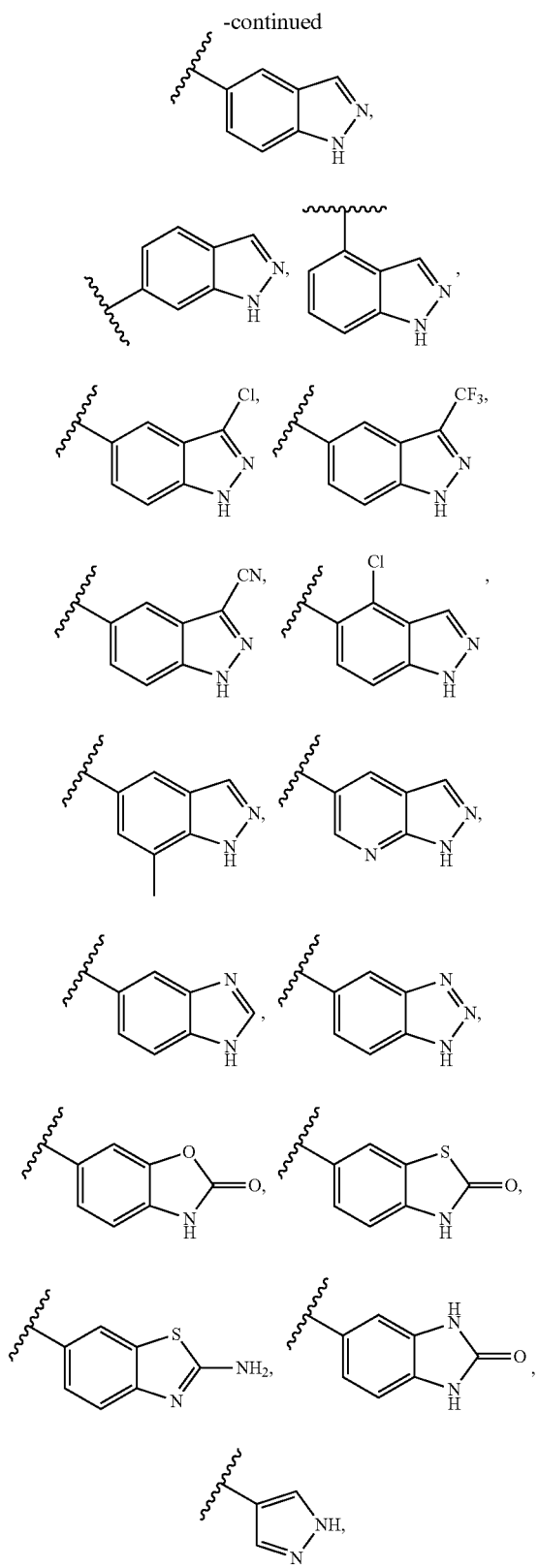

Ar³, ((thiazolyl)amino)phenyl, (pyrimidinyl)amino, and (pyrazolopyrimidinyl)amino;
R² is hydrogen, alkyl, haloalkyl, alkoxy, haloalkoxy, or alkylSO₂;

Ar¹ phenyl or pyridinyl and is substituted with 0-3 substituents selected from halo, alkyl, haloalkyl, alkoxy, haloalkoxy, dialkylamino, and alkylSO₂;
Ar² is

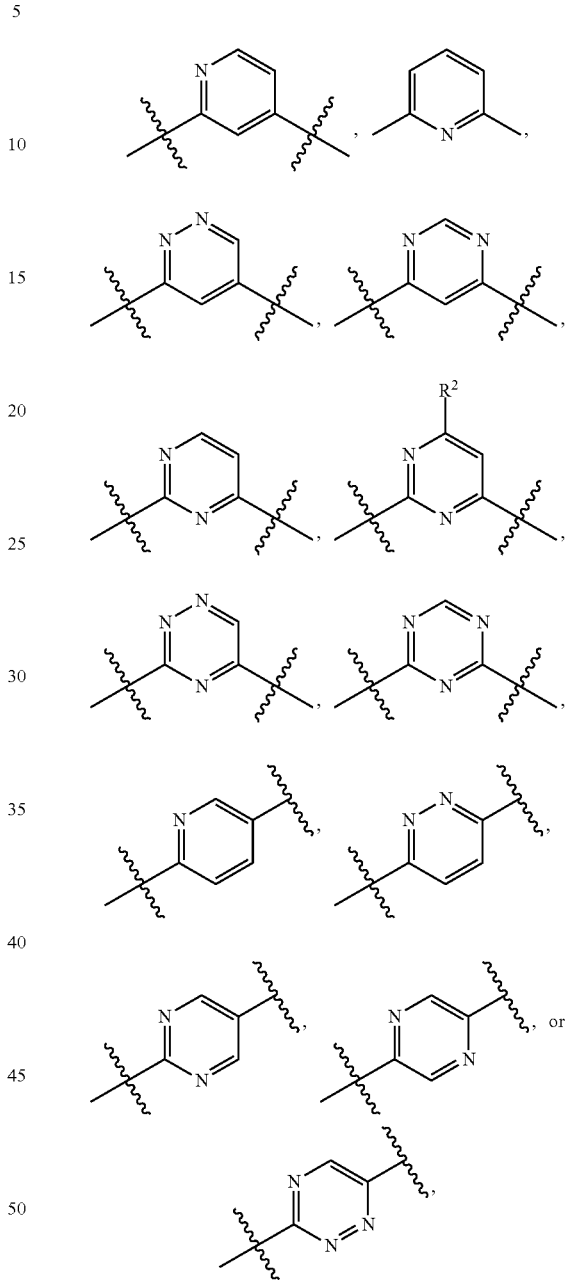

and where Ar² is substituted with 0-1 substituents selected from the group consisting of hydroxy, cyano, halo, alkyl, alkoxy, and haloalkoxy;
Ar³ is phenyl, pyridinyl, pyrazinyl, pyrimidinyl, or pyridazinyl, and is substituted with 1 substituent selected from hydroxy, amino, NHCO₂alkyl, or NHSO₂alkyl, and is also substituted with 0-3 substituents selected from halo, alkyl, and haloalkyl;
L¹ is a direct bond, —CH₂—, or —CH₂CH₂—; and
L² is —O—, —CH₂—, —OCH₂—, —CH₂NH—, —NHCH₂—, —CH₂—, —CH₂CH₂—, —CH(CH₃)CH₂—, —CH₂CH(CH₃)—, —CH₂CH₂CH₂—, or cyclopropdiyl;
or a pharmaceutically acceptable salt thereof.

Another aspect of the invention is a compound of formula I where

R¹ is selected from the group consisting of

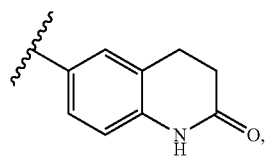 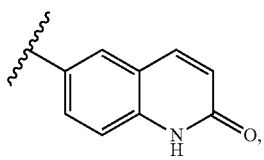

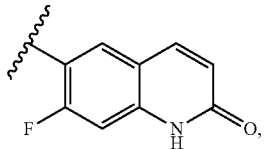 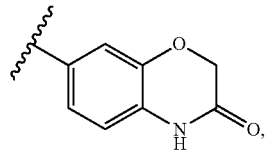

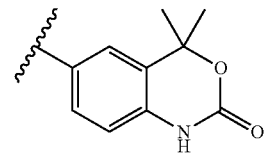 

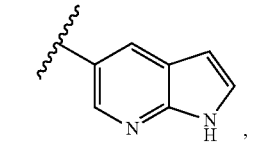 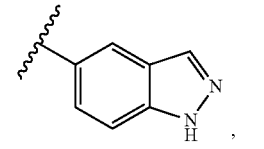

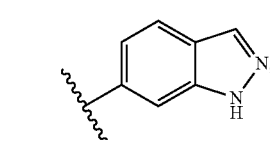 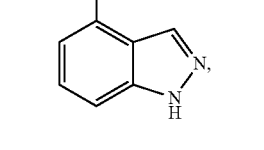

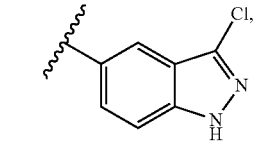 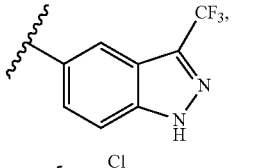

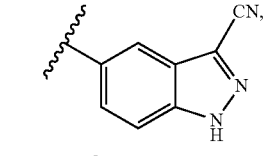 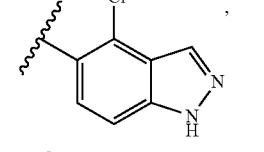

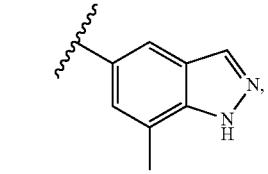 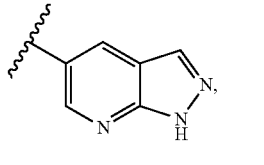

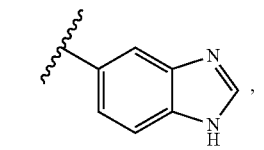 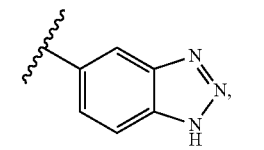

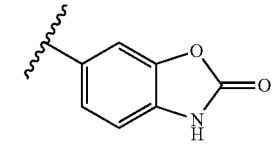 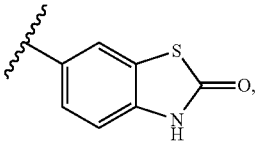

-continued

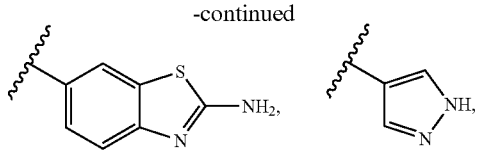

Ar³, ((thiazolyl)amino)phenyl, (pyrimidinyl)amino, or (pyrazolopyrimidinyl)amino;

R² is hydrogen, alkyl, or haloalkyl;

Ar¹ is phenyl or pyridinyl and is substituted with 0-3 substituents selected from halo, alkyl, alkoxy, haloalkoxy, and alkylSO₂;

Ar² is

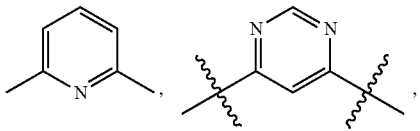

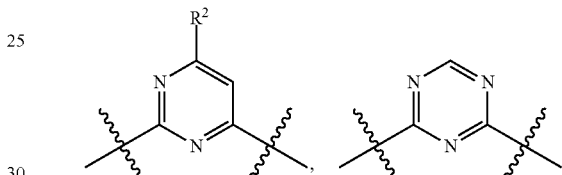

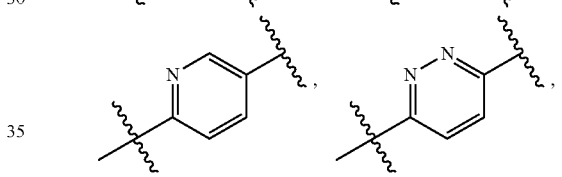

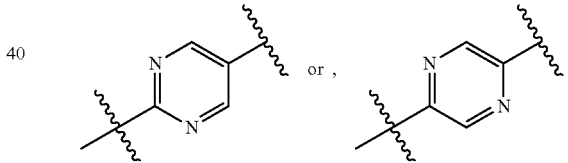

Ar³ is phenyl, pyridinyl, or pyridazinyl, and is substituted with 1 substituent selected from hydroxyl or amino;

L¹ is a direct bond, or; and

L² is —O— or —CH₂—, —CH₂CH₂—CH₂CH₂—, —CH(CH₃)CH₂—, —CH₂CH(CH₃)—, —CH₂CH₂CH₂—, or cyclopropdiyl;

or a pharmaceutically acceptable salt thereof or a pharmaceutically acceptable salt thereof.

Another aspect of the invention is a compound of formula I where

R¹ is selected from the group consisting of

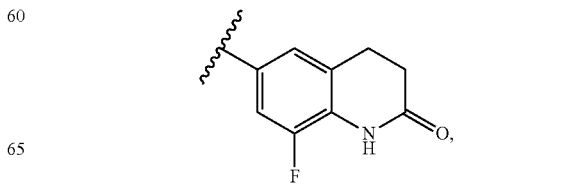

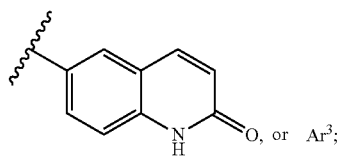

Ar¹ phenyl or pyridinyl and is substituted with 0-3 substituents selected from halo, alkyl, alkoxy, and haloalkoxy;
Ar³ is phenyl and is substituted with 1 hydroxy substituent;
L¹ is a direct bond or —CH₂—; and
L² is —CH₂O—;
or a pharmaceutically acceptable salt thereof.
Another aspect of the invention is a compound of formula I where R¹ is selected from the group consisting of

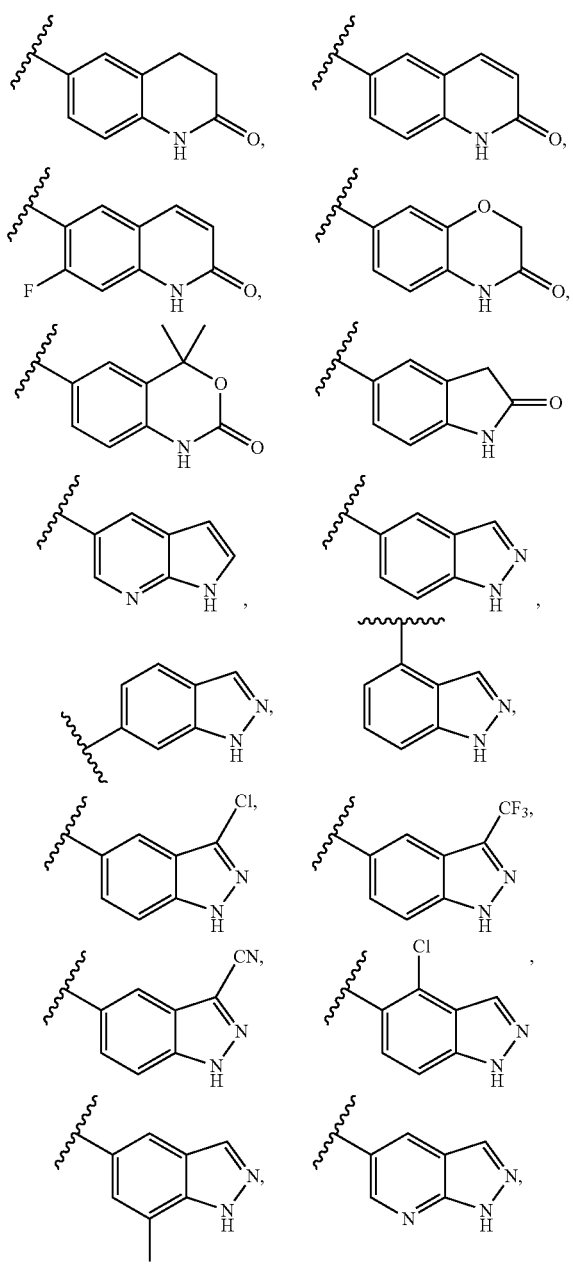

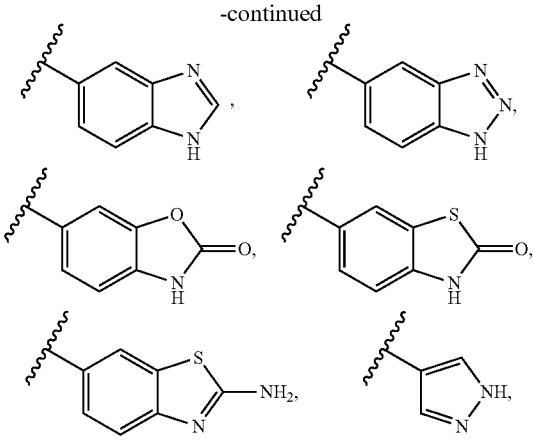

Ar³, ((thiazolyl)amino)phenyl, (pyrimidinyl)amino, or (pyrazolopyrimidinyl)amino; and
Ar³ is phenyl, pyrimidinyl, or pyridazinyl, and is substituted with 1 substituent selected from hydroxy and amino;
Another aspect of the invention is a compound of formula I where Ar² is

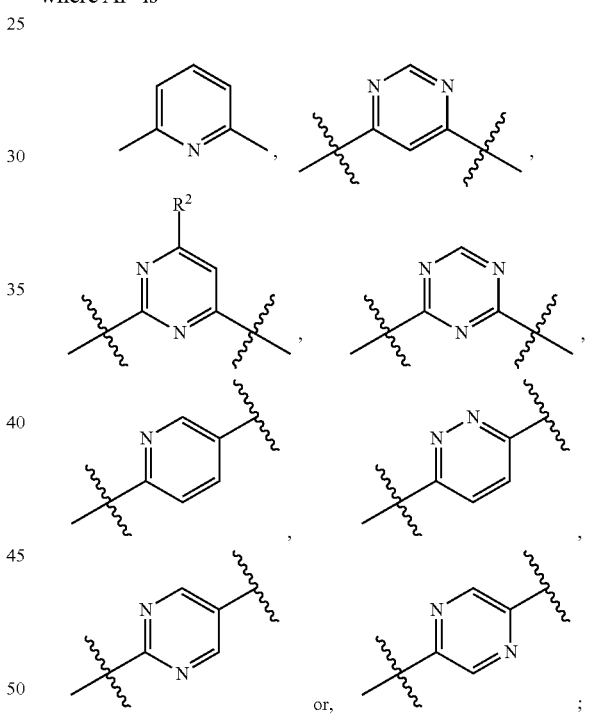

and
R² is hydrogen, alkyl, or haloalkyl.
where:
where:
R¹ is selected from the group consisting of

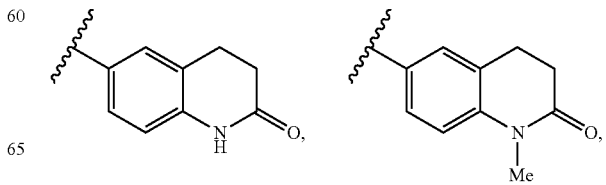

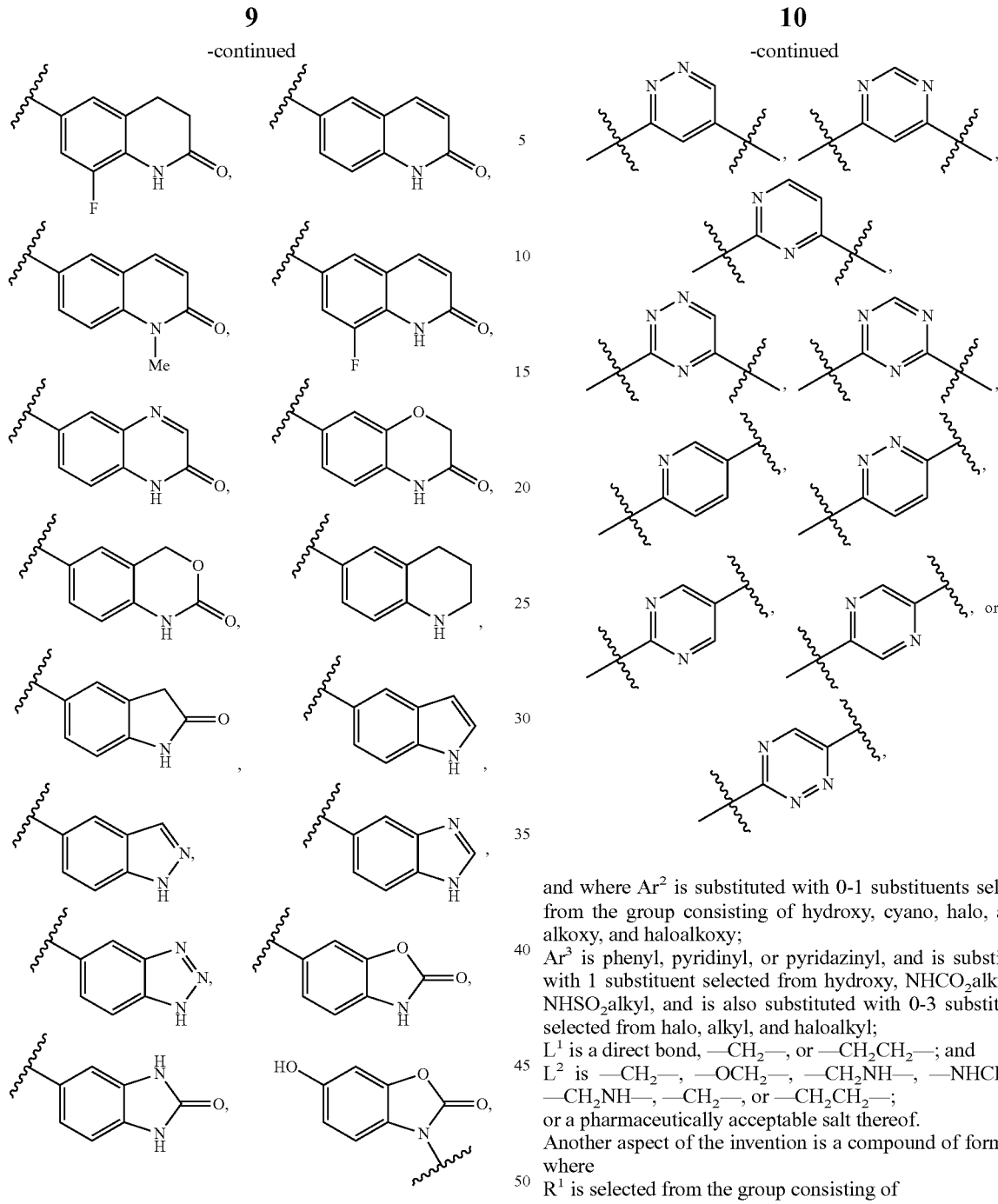

and where Ar² is substituted with 0-1 substituents selected from the group consisting of hydroxy, cyano, halo, alkyl, alkoxy, and haloalkoxy;
Ar³ is phenyl, pyridinyl, or pyridazinyl, and is substituted with 1 substituent selected from hydroxy, NHCO₂alkyl, or NHSO₂alkyl, and is also substituted with 0-3 substituents selected from halo, alkyl, and haloalkyl;
L¹ is a direct bond, —CH₂—, or —CH₂CH₂—; and
L² is —CH₂—, —OCH₂—, —CH₂NH—, —NHCH₂—, —CH₂NH—, —CH₂—, or —CH₂CH₂—;
or a pharmaceutically acceptable salt thereof.
Another aspect of the invention is a compound of formula I where
R¹ is selected from the group consisting of

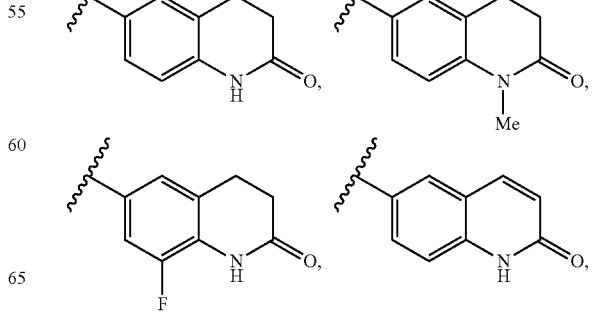

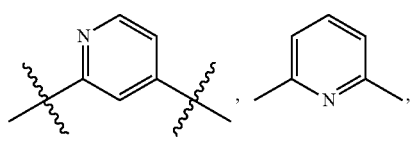

Ar³, or (pyrimidinyl)amino;
R² is hydrogen or alkyl;
Ar¹ phenyl or pyridinyl and is substituted with 0-3 substituents selected from halo, alkyl, haloalkyl, alkoxy, and haloalkoxy;
Ar² is

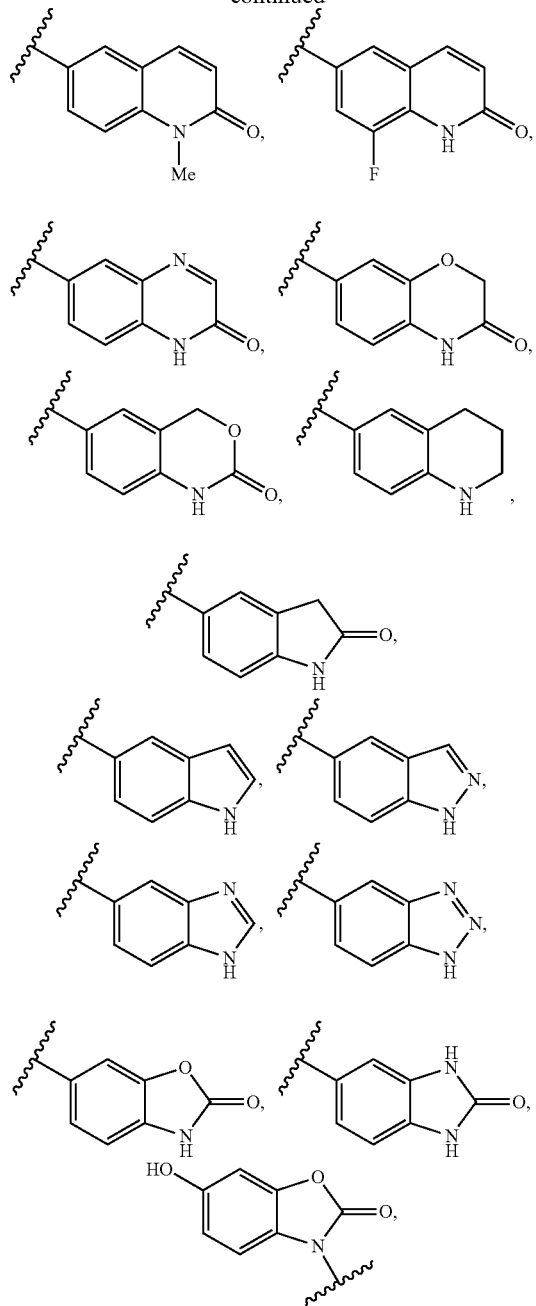

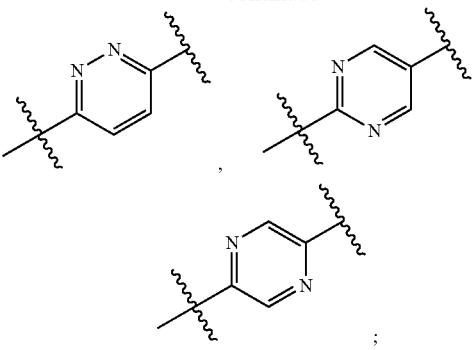

Ar³ is phenyl, pyridinyl, or pyridazinyl, and is substituted with 1 substituent selected from hydroxy, NHCO₂alkyl, or NHSO₂alkyl, and is also substituted with 0-3 substituents selected from halo, alkyl, and haloalkyl;
L¹ is a direct bond, —CH₂—, or —CH₂CH₂—; and
L² is —CH₂O—, —OCH₂—, —NHCH₂—, —CH₂—, or —CH₂CH₂—;
or a pharmaceutically acceptable salt thereof. or a pharmaceutically acceptable salt thereof.

Another aspect of the invention is a compound of formula I where
R¹ is selected from the group consisting of

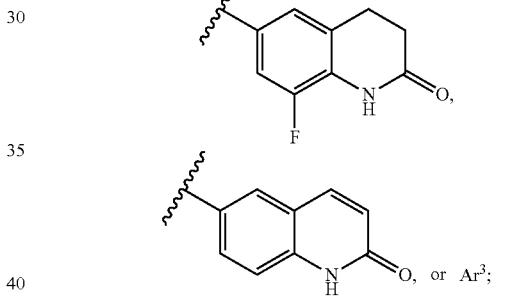

Ar³, or (pyrimidinyl)amino;
Ar¹ phenyl or pyridinyl and is substituted with 0-3 substituents selected from halo, alkyl, haloalkyl, alkoxy, and haloalkoxy;
Ar³ is phenyl and is substituted with 1 hydroxy substituent;
L¹ is a direct bond or —CH₂—; and
L² is —CH₂O—;
or a pharmaceutically acceptable salt thereof.

Another aspect of the invention is a compound of formula I where
Ar² is

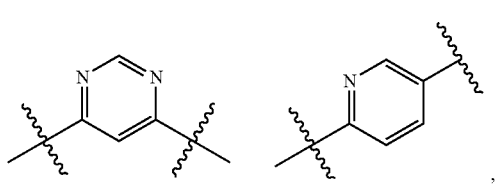

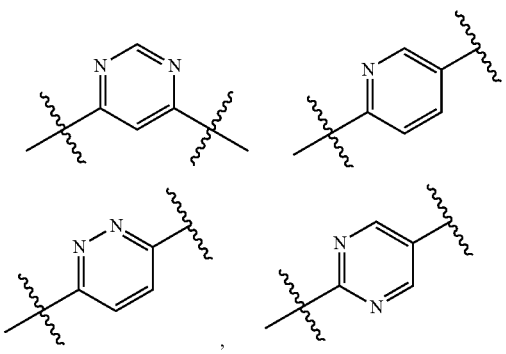

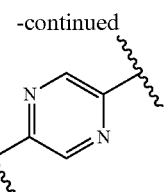

or a pharmaceutically acceptable salt thereof.

Another aspect of the invention is a compound of formula I where $L^1$ is a direct bond, or —CH$_2$—; and $L^2$ is —CH$_2$O—; or a pharmaceutically acceptable salt thereof.

For a compound of formula I, the scope of any instance of a variable substituent, including $R^1$, $R^2$, $Ar^1$, $Ar^2$, $Ar^3L^1$, and $L^2$ can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The compounds include all tautomeric forms. For example, $Ar^2$ substituted with 1 hydroxy adjacent to a nitrogen atom would include the keto tautomer.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom. The invention includes all stereoisomeric forms of the compounds, both mixtures and separated isomers. Mixtures of stereoisomers can be separated into individual isomers by methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

Scheme 1.

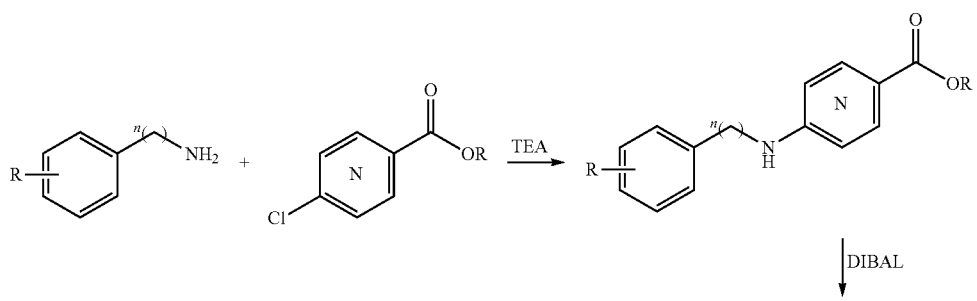

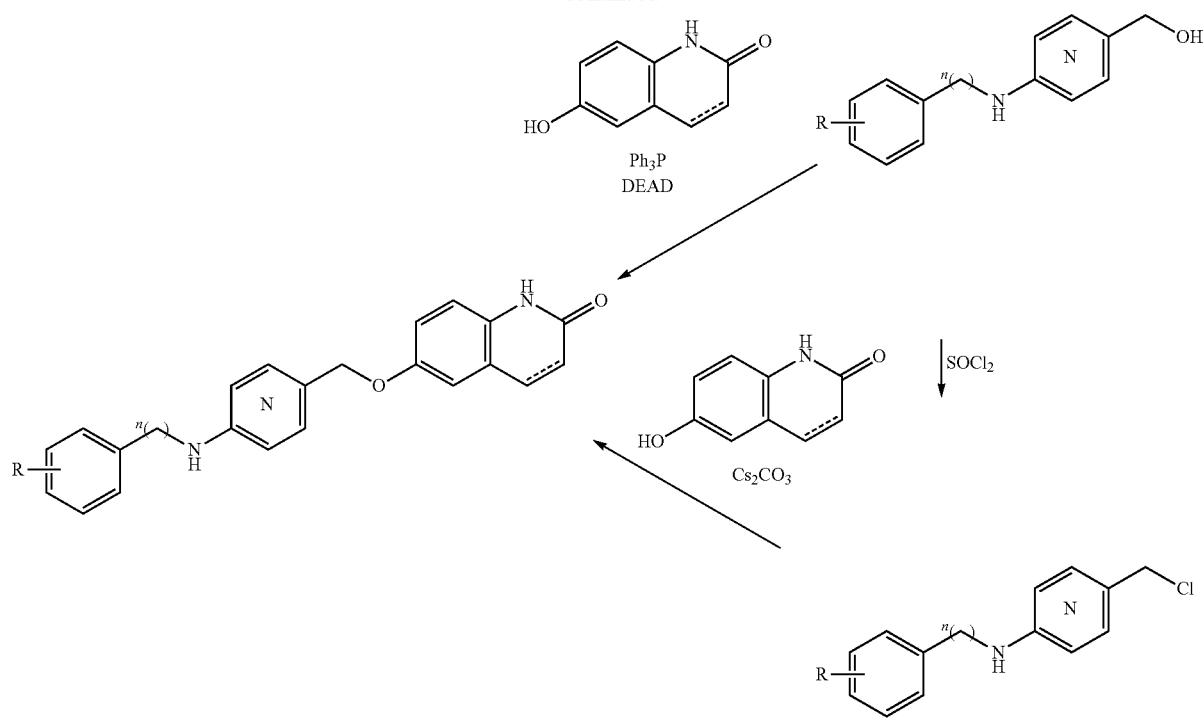
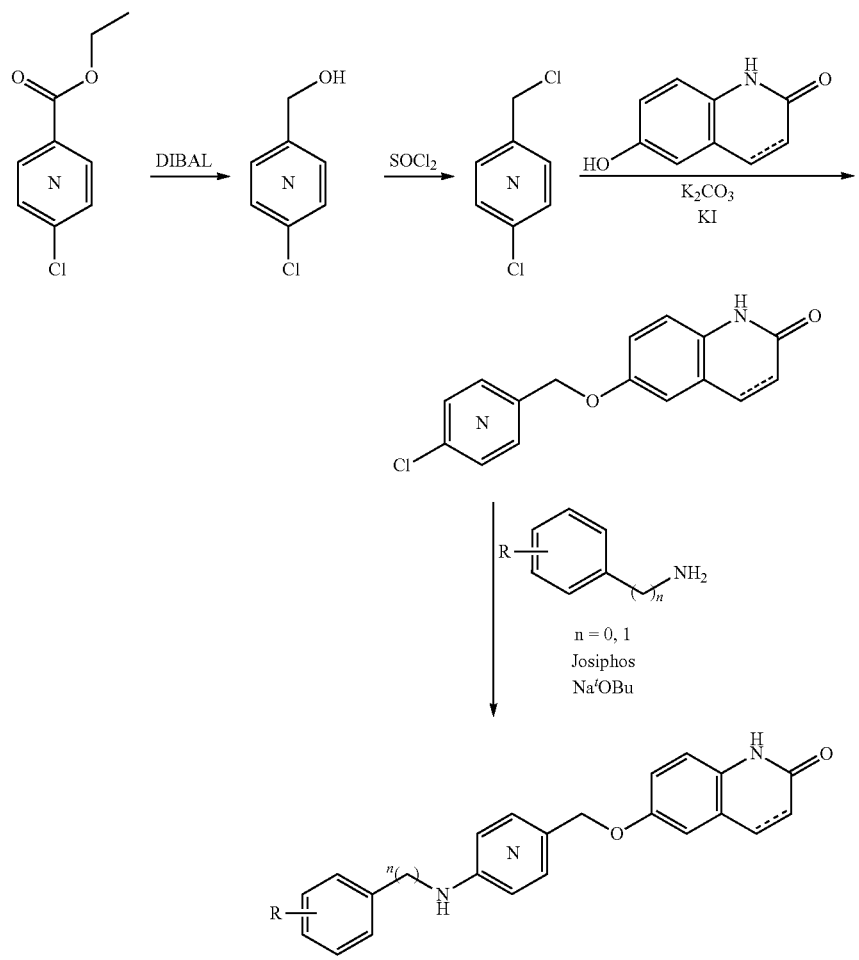
Scheme 2.

Biological Methods

Electrophysiology NMDA Receptor Experiments.

Stage V and VI oocytes were surgically removed from the ovaries of large, well-fed and healthy *Xenopus laevis* anesthetized with 3-amino-benzoic acid ethyl ester (3 gm/l). Clusters of isolated oocytes were incubated with 292 U/ml Worthington (Freehold, N.J.) type IV collagenase or 1.3 mg/ml collagenase (Life Technologies, Gaithersburg, Md.; 17018-029) for 2 hr in $Ca^{2+}$-free solution comprised of (in mM) 115 NaCl, 2.5 KCl, and 10 HEPES, pH 7.5, with slow agitation to remove the follicular cell layer. Oocytes were then washed in the same solution supplemented with 1.8 mM $CaCl_2$ and maintained in Barth's solution comprised of (in mM): 88 NaCl, 1 KCl, 2.4 $NaHCO_3$, 10 HEPES, 0.82 $MgSO_4$, 0.33 $Ca(NO_3)_2$, and 0.91 $CaCl_2$ and supplemented with 100 µg/ml gentamycin, 10 µg/ml streptomycin, and 10 µg/ml penicillin. Oocytes were manually defolliculated and injected within 24 hrs of isolation with 3-5 ng of human GluN1 subunit cRNA and 7-10 ng of human GluN2 cRNA subunit in a 50 nl volume, and incubated in Barth's solution at 18° C. for 2-7 d. Glass injection pipettes had tip sizes ranging from 10-20 microns, and were backfilled with mineral oil. cRNA was synthesized from linearized template cDNA for rat glutamate receptor subunits according to manufacturer specifications (Ambion).

Two electrode voltage-clamp recordings were made 2-7 days post-injection. Oocytes were placed in a dual-track plexiglass recording chamber with a single perfusion line that splits in a Y-configuration to perfuse two oocytes. Dual recordings were made at room temperature (23° C.) using two Warner OC725B two-electrode voltage clamp amplifiers, arranged as recommended by the manufacturer. Glass microelectrodes (1-10 Megaohms) were filled with 300 mM KCl (voltage electrode) or 3 M KCl (current electrode). The bath clamps communicated across silver chloride wires placed into each side of the recording chamber, both of which were assumed to be at a reference potential of 0 mV. Oocytes were perfused with a solution comprised of (in mM) 90 NaCl, 1 KCl, 10 HEPES, 10 EDTA and 0.5 $BaCl_2$; pH 7.4, adjusted by addition of NaOH. Oocytes were recorded under voltage clamp at −40 mV. Final concentrations for glutamate and glycine were 50 µM and 30 µM, respectively. Concentration-response curves for experimental compounds were obtained by applying in successive fashion maximal glutamate/glycine, followed by glutamate/glycine plus variable concentrations of experimental compounds. Dose response curves consisting of four to eight concentrations were obtained in this manner. The baseline leak current at −40 mV was measured before and after recording, and the full recording linearly corrected for any change in leak current. The level of inhibition by applied experimental compounds was expressed as a percent of the initial glutamate response, and averaged together across oocytes from multiple experiments. Results were pooled, and the average percent responses at antagonist concentrations were fit by the equation, Percent Response= $(100-\text{minimum})/(1+([\text{conc}]/IC50)^{nH})+\text{minimum}$ where minimum is the residual percent response in saturating concentration of the experimental compounds, IC50 is the concentration of antagonist that causes half of the achievable inhibition, and nH is a slope factor describing steepness of the inhibition curve. Minimum was constrained to be greater than For NMDA receptor subtype selectivity experiments human GluN1/GluN2A, GluN1/GluN2C, and GluN1/GluN2D cRNAs were expressed in *Xenopus laevis* as described above. Here, 10 µM concentrations of the antagonist was perfused with 50 µM glutamate and 30 µM glycine onto the oocyte for two min and the remaining current in the presence of the antagonist was compared to the maximal current obtained with 50 µM glutamate and 30 µM glycine alone (defined as 100%). When $IC_{50}$ determinations were made against other NMDA receptor subtypes the protocol as described above was followed. Activity is illustrated in table 1. according to the following: + 0-200 nM; ++ 201-1000 nM; +++ 1000-10000 nM; ++++ >10000 nM.

TABLE 1

| Example | hNR2B $IC_{50}$, nM | Rating |
|---------|---------------------|--------|
| 1 | 87 | + |
| 2 | >3000 | +++ |
| 3 |  | + |
| 4 |  | ++++ |
| 5 |  | ++ |
| 6 |  | +++ |
| 7 |  | + |
| 8 |  | +++ |
| 9 |  | + |
| 10 | 13 | + |
| 11 |  | + |
| 12 | 394 |  |
| 13 | 395 |  |
| 14 | 64 |  |
| 15 | >3000 |  |
| 16 | 14 |  |
| 17 | >1000 |  |
| 18 | 5 |  |
| 19 |  | + |
| 20 |  | + |
| 21 |  | ++++ |
| 22 |  | + |
| 23 |  | + |
| 24 | 90 | + |
| 25 | 97 | + |
| 26 | 139 | + |
| 27 | 62 | + |
| 28 | 101 | + |
| 29 |  | + |
| 30 |  | + |
| 31 |  | + |
| 32 |  | ++ |
| 33 |  | +++ |
| 34 |  | + |
| 35 |  | + |
| 36 |  | + |
| 37 |  | + |
| 38 |  | + |
| 39 |  | + |
| 40 |  | + |
| 41 |  | + |
| 42 |  | + |
| 43 |  | + |
| 44 |  | + |
| 45 |  | + |
| 46 |  | + |
| 47 |  | + |
| 48 |  | + |
| 49 |  | + |
| 50 |  | + |
| 51 |  | + |
| 52 |  | + |
| 53 |  | + |
| 54 |  | + |
| 55 |  | + |
| 56 |  | + |
| 57 |  | + |
| 58 |  | + |
| 59 |  | + |
| 60 |  | + |
| 61 |  | + |
| 62 |  | + |
| 63 |  | + |
| 64 |  | + |
| 65 |  | + |
| 66 |  | + |

TABLE 1-continued

| Example | hNR2B IC$_{50}$, nM | Rating |
|---|---|---|
| 67 | | + |
| 68 | | + |
| 69 | | + |
| 70 | | + |
| 71 | | + |
| 72 | | + |
| 73 | | + |
| 74 | | + |
| 75 | | + |
| 76 | | + |
| 77 | | + |
| 78 | | + |
| 79 | | + |
| 80 | | + |
| 81 | | + |
| 82 | | + |
| 83 | | + |
| 84 | | + |
| 85 | | + |
| 86 | | + |
| 87 | | + |
| 88 | | + |
| 89 | | + |
| 90 | | + |
| 91 | | + |
| 92 | | + |
| 93 | 1250 | |
| 94 | | +++ |
| 95 | 36 | |
| 96 | | + |
| 97 | | +++ |
| 98 | >3000 | |
| 99 | | +++ |
| 100 | | ++ |
| 101 | | +++ |
| 102 | 4600 | |
| 103 | 1000 | |
| 104 | 183 | |
| 105 | 2.5 | |
| 106 | | NA |
| 107 | 35 | |
| 108 | | + |
| 109 | | + |
| 110 | | + |
| 111 | | +++ |
| 112 | | ++ |
| 113 | | ++++ |
| 114 | | ++++ |
| 115 | | ++++ |
| 116 | | +++ |
| 117 | | ++++ |
| 118 | | ++++ |
| 119 | | + |
| 120 | | +++ |
| 121 | | + |
| 122 | | + |
| 123 | | + |
| 124 | | ++++ |
| 125 | | +++ |
| 126 | | + |
| 127 | | ++ |
| 128 | | + |
| 129 | | + |
| 130 | | +++ |
| 131 | | + |
| 132 | | + |
| 133 | | +++ |
| 134 | | +++ |
| 135 | | +++ |
| 136 | | +++ |
| 137 | | ++ |
| 138 | | ++++ |
| 139 | | + |
| 140 | | ++ |
| 141 | | +++ |
| 142 | | +++ |
| 143 | | + |
| 144 | | + |
| 145 | | + |
| 146 | | + |
| 147 | | +++ |
| 148 | | +++ |
| 149 | | + |
| 150 | | + |
| 151 | | ++ |
| 152 | | + |
| 153 | | + |
| 154 | | + |
| 155 | | + |
| 156 | 135 | |

Pharmaceutical Compositions and Methods of Treatment

Compounds of formula I can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment of depression, Alzheimer's disease, Parkinson's disease, or neuropathic pain, which comprises administering to a patient a therapeutically affective amount of a compound of formula I.

Another aspect of the invention is a method for the treatment of depression which comprises administering to a patient a therapeutically affective amount of a compound of formula I.

Another aspect of the invention is a method for the treatment of Alzheimer's disease which comprises administering to a patient a therapeutically affective amount of a compound of formula I.

Another aspect of the invention is a method for the treatment of neuropathic pain which comprises administering to a patient a therapeutically affective amount of a compound of formula I.

Another aspect of the invention is a method for the treatment of Parkinson's disease which comprises administering to a patient a therapeutically affective amount of a compound of formula I.

Another aspect of the invention is the use of a compound of formula I in the manufacture of a medicament for the treatment of neurological or psychiatric disorders.

Another aspect of the invention is the use of a compound of formula I in the manufacture of a medicament for the treatment of depression, Alzheimer's disease, Parkinson's disease, neuropathic pain, or Parkinson's disease.

Another aspect of the invention is the use of a compound of formula I in the manufacture of a medicament for the treatment of depression.

Another aspect of the invention is the use of a compound of formula I in the manufacture of a medicament for the treatment of Alzheimer's disease.

Another aspect of the invention is the use of a compound of formula I in the manufacture of a medicament for the treatment of Parkinson's disease.

Another aspect of the invention is the use of a compound of formula I in the manufacture of a medicament for the treatment of neuropathic pain.

"Patient" means a person suitable for therapy as understood by practitioners in the field of affective disorders and neurodegenerative disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$ (CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "L" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

The variables (e.g. numbered "R" substituents) used to describe some of the exemplified compounds are intended only to illustrate the compounds and are not to be confused with variables used in the claims or in other sections of the specification.

Synthesis of Common Intermediates 6-acetyl-8-fluoro-3,4-dihydroquinolin-2(1H)-one

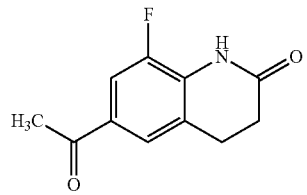

To a stirring solution of 8-fluoro-3,4-dihydroquinolin-2 (1H)-one (1.6 g, 9.69 mmol) and acetyl chloride (1.722 mL, 24.22 mmol) in carbon disulfide (20 mL, 9.69 mmol) at 0° C. was added in portions aluminum chloride (6.59 g, 49.4 mmol). The reaction mixture was stirred at 100° C. without a condensor until the solvent evaporated, then a condensor was fitted in place and stirring continued at 100° C. for 4 h. After cooling, the reaction contents were carefully poured into ice water and partitioned between DCM and water. The aqueous layer was extracted with DCM (3×150 mL). The combined organic washes were dried over MgSO$_4$ and concentrated under vacuum to a tan solid. This was purified by flash chromatography on silica gel using 1% MeOH in DCM to give 6-acetyl-8-fluoro-3,4-dihydroquinolin-2(1H)-one as a yellow solid (1.6 g, 80%). $^1$H NMR (400 MHz, CHLOROFORM-d) δ ppm 7.72 (br. s., 1H), 7.68-7.60 (m, 1H), 2.76-2.58 (m, 2H), 2.58-2.50 (m, 2H), 1.58 (s, 13H). LCMS: R.T.=1.335 min; [M+H]$^+$=208.0.

8-fluoro-2-oxo-1,2,3,4-tetrahydroquinolin-6-yl acetate

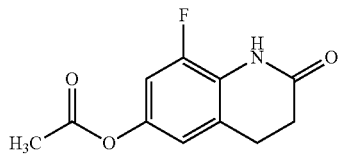

To a stirring solution of 6-acetyl-8-fluoro-3,4-dihydroquinolin-2(1H)-one (1.6 g, 7.72 mmol) in CHCl₃ (100 mL) at room temperature was added in portions m-chloroperbenzoic acid (2.077 g, 9.27 mmol). The reaction mixture was stirred at reflux for 18 h, then cooled to room temperature and quenched with saturated sodium bicarbonate solution. The reaction was extracted with DCM (3×100 mL). The combined organic layers were dried over MgSO₄ and concentrated under vacuum to a yellow oil. This was purified by column chromatography on silica gel using 1% MeOH in DCM to give 8-fluoro-2-oxo-1,2,3,4-tetrahydroquinolin-6-yl acetate as a white foam (1.3 g, 75%). $^1$H NMR (400 MHz, CHLOROFORM-d) δ ppm 7.28 (s, 1H), 6.84-6.72 (m, 1H), 2.77-2.54 (m, 2H), 2.45-2.21 (m, 2H), 1.62 (s, 3H). LCMS: R.T.=1.382 min; [M+H]⁺=224.0.

8-fluoro-6-hydroxy-3,4-dihydroquinolin-2(1H)-one

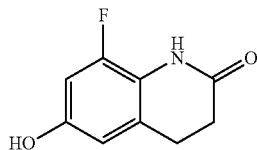

To a solution of 8-fluoro-2-oxo-1,2,3,4-tetrahydroquinolin-6-yl acetate (1.3 g, 5.82 mmol) in MeOH (50 mL) at room temperature was added 1N NaOH (11.65 mL, 11.65 mmol). The reaction mixture was stirred at room temperature overnight, then concentrated to a yellow oil. This was diluted with water and acidified with conc. HCl to pH 1. The precipitate was collected by filtration, washed with water, and recrystallized from MeOH/water to give 8-fluoro-6-hydroxy-3,4-dihydroquinolin-2(1H)-one as a white solid (0.46 g, 44%). $^1$H NMR (400 MHz, METHANOL-d₄) δ ppm 6.57-6.48 (m, 2H), 2.93 (s, 2H), 2.56 (dd, J=7.9, 6.9 Hz, 2H). LCMS: R.T.=1.125 min; [M+H]⁺=182.1.

6-bromo-1-((2-(trimethylsilyl)ethoxy)methyl)-1,8-naphthyridin-2(1H)-one

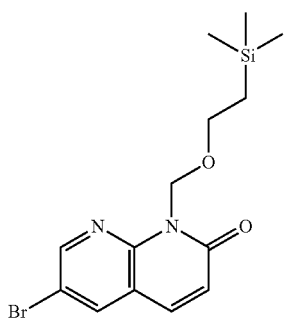 [SMILES: C[Si](C)(C)CCOCn1c(=O)ccc2cc(Br)cnc21]

To a solution of 6-bromo-1,8-naphthyridin-2(1H)-one (0.1 g, 0.444 mmol) in DMF (2 mL) was added sodium hydride (0.021 g, 0.889 mmol) at 0° C. The reaction was stirred at 0° C. for 30 min, then SEM-Cl (0.118 mL, 0.667 mmol) was added. The reaction was stirred at room temperature overnight, then diluted with ammonium chloride solution, extracted with ethyl acetate, dried over Na₂SO₄, and concentrated. The crude product was purified by flash chromatography on silica gel using 20% ethyl acetate in petroleum ether to give 6-bromo-1-((2-(trimethylsilyl)ethoxy)methyl)-1,8-naphthyridin-2(1H)-one (0.12 g, 76%). $^1$HNMR 400 MHz (CDCl₃): 0.034 (s, 9H), 0.95-0.99 (m, 2H), 3.73-3.77 (m, 2H), 5.92 (s, 2H), 6.75-6.77 (m, 1H), 7.56-7.58 (m, 1H), 7.96-7.98 (m, 1H), 8.63-8.64 (m, 1H).

Example 1

6-((6-(4-chlorobenzylamino)pyridin-3-yl)methoxy)quinolin-2(1H)-one 6-((6-chloropyridin-3-yl)methoxy)quinolin-2(1H)-one

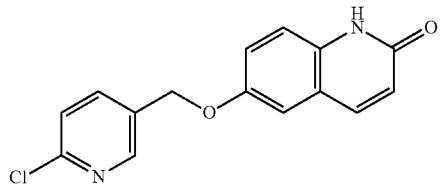 [SMILES: O=c1ccc2cc(OCc3ccc(Cl)nc3)ccc2[nH]1]

2-chloro-5-(chloromethyl)pyridine (0.995 g, 6.14 mmol) was added slowly to a well-stirred mixture of 6-hydroxyquinolin-2(1H)-one (0.9 g, 5.58 mmol), K₂CO₃ (1.158 g, 8.38 mmol) and potassium iodide (0.927 g, 5.58 mmol) in DMF (18 mL) at 40° C. The reaction mixture was stirred at 40° C. for 18 h and poured into ice/water. The suspension was filtered and the filter cake taken up in methanol/DCM and purified by flash chromatography on silica gel using 1-5% (10% ammonium hydroxide in methanol)/DCM. The desired fractions were concentrated to give 6-((6-chloropyridin-3-yl)methoxy)quinolin-2(1H)-one as a beige solid (1.0 g, 63%). $^1$H NMR (400 MHz, DMSO-d₆) δ ppm 11.69 (1H, s), 8.55 (1H, d, J=2.01 Hz), 7.98 (1H, dd, J=8.03, 2.51 Hz), 7.85 (1H, d, J=9.54 Hz), 7.58 (1H, d, J=8.03 Hz), 7.18-7.32 (2H, m), 6.51 (1H, d, J=9.54 Hz), 5.19 (2H, s). LCMS: R.T.=3.07; [M+H]⁺=287.01.

6-((6-(4-chlorobenzylamino)pyridin-3-yl)methoxy)quinolin-2(1H)-one trifluoroacetate

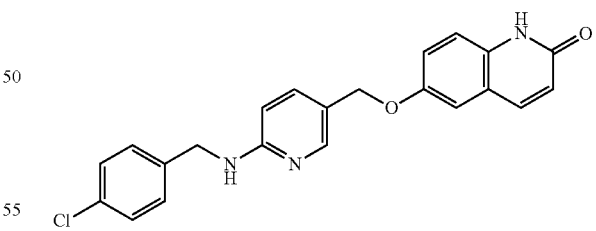

A solution of palladium(II) acetate (3.92 mg, 0.017 mmol) and (R)-1-[(S$_P$)-2-(Dicyclohexylphosphino)ferrocenyl]ethyldi-tert-butylphosphine (9.67 mg, 0.017 mmol) in DME (0.5 mL) was added to a 5 mL reaction vial containing 6-((6-chloropyridin-3-yl)methoxy)quinolin-2(1H)-one (0.1 g, 0.349 mmol) and sodium tert-butoxide (0.047 g, 0.488 mmol) in DME (1 mL). (4-chlorophenyl)methanamine (0.049 g, 0.349 mmol) was added to the mixture. The reaction mixture was heated at 90° C. for 18 h and cooled to room temperature. The resulting suspension was diluted with water, stirred for 10 min, and filtered. The filter cake was taken up in methanol/

DCM (2:1) and stirred for 30 min. The suspension was filtered and the filter cake was washed with methanol and suction dried. The filtrate was concentrated and purified by preparative HPLC on a Xterra C18 (5 µm, 30×100 mm) reversed phase column using 25-100% of mobile phase B (90% methanol/10% water/0.1% TFA) in mobile phase A (10% methanol/90% water/0.1% TFA). The desired peak was concentrated to give 6-((6-(4-chlorobenzylamino)pyridin-3-yl)methoxy)quinolin-2(1H)-one trifluoroacetate as a yellow solid (0.056 g, 30%). $^1$H NMR (500 MHz, METHANOL-$d_4$) δ ppm 7.80-8.16 (3H, m), 7.42 (4H, s), 7.23-7.38 (3H, m), 7.15 (1H, d, J=9.31 Hz), 6.64 (1H, d, J=9.46 Hz), 5.10 (2H, s), 4.62 (2H, s). $^1$H NMR (400 MHz, DMSO-$d_6$) δ ppm 11.68 (1H, s), 8.10 (1H, d, J=1.51 Hz), 7.76-7.94 (2H, m), 7.36-7.49 (4H, m), 7.33 (1H, d, J=2.51 Hz), 7.14-7.29 (2H, m), 6.94 (1H, d, J=8.78 Hz), 6.52 (1H, d, J=9.29 Hz), 5.00 (2H, s), 4.56 (2H, br. s.). LCMS: R.T.=2.89; [M+H]$^+$=392.20.

Example 2

6-((6-(3,4-dichlorobenzylamino)pyridin-3-yl)methoxy)quinolin-2(1H)-one

Methyl 6-(3,4-dichlorobenzylamino)nicotinate

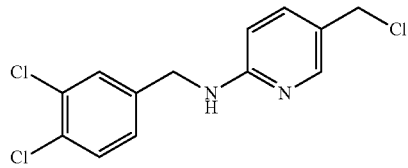

A mixture of (3,4-dichlorophenyl)methanamine (1.010 mL, 7.58 mmol), TEA (1.218 mL, 8.74 mmol), and methyl 6-chloronicotinate (1 g, 5.83 mmol) in ethanol (29 mL) was heated at 120° C. for 5 min in a microwave oven. The reaction mixture was further heated at 100° C. for 54 h, then concentrated. The residue was purified by flash chromatography on silica gel using 5-35% ethyl acetate in hexanes. The desired fractions were concentrated to give methyl 6-(3,4-dichlorobenzylamino)nicotinate as a pale yellow solid (0.55 g, 33%). $^1$H NMR (400 MHz, CHLOROFORM-d) δ ppm 8.77 (1H, s), 8.01 (1H, dd, J=8.78, 2.01 Hz), 7.33-7.52 (2H, m), 7.19 (1H, d, J=8.03 Hz), 6.37 (1H, d, J=8.78 Hz), 5.37 (1H, br. s.), 4.58 (2H, d, J=6.02 Hz), 3.88 (3H, s). LCMS: R.T.=2.81; [M+H]$^+$=311.18.

(6-(3,4-dichlorobenzylamino)pyridin-3-yl)methanol

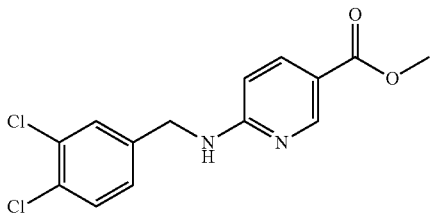 [SMILES: COC(=O)c1ccc(NCc2ccc(Cl)c(Cl)c2)nc1]

A solution of methyl 6-((3,4-dichlorobenzyl)amino)nicotinate (0.88 g, 2.83 mmol) in THF (18.9 mL) was cooled to −78° C. and a 1M solution of DIBAL-H (14.14 mL, 14.14 mmol) in toluene was added. The mixture was stirred for 1.5 h while warming to room temperature. The reaction mixture was diluted with THF (20 mL) and quenched with $Na_2SO_4 \cdot 10H_2O$ followed by a few drops of water. The mixture was stirred at room temperature for 18 h, then filtered through a pad of Celite topped with silica gel. The pad was washed with ethyl acetate and the filtrate was concentrated. The residue was purified by flash chromatography on silica gel using 45-80% ethyl acetate in hexanes. The desired fractions were concentrated to give (6-(3,4-dichlorobenzylamino)pyridin-3-yl)methanol as a white solid (0.46 g, 57%). $^1$H NMR (400 MHz, METHANOL-$d_4$) δ ppm 7.91 (1H, d, J=1.76 Hz), 7.40-7.52 (3H, m), 7.26 (1H, dd, J=8.28, 2.01 Hz), 6.51-6.59 (1H, m), 4.50 (2H, s), 4.44 (2H, s). LCMS: R.T.=2.74; [M+H]$^+$=282.99.

5-(chloromethyl)-N-(3,4-dichlorobenzyl)pyridin-2-amine

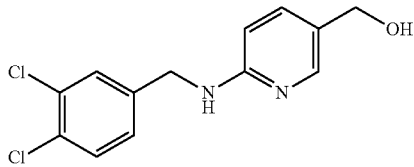 [SMILES: OCc1ccc(NCc2ccc(Cl)c(Cl)c2)nc1]

Thionyl chloride (0.103 mL, 1.413 mmol) was added to a suspension of (6-((3,4-dichlorobenzyl)amino)pyridin-3-yl)methanol (0.1 g, 0.353 mmol) in DCM (3.5 mL) cooled to 0° C. The mixture was stirred for 18 h at room temperature. The resulting white suspension was concentrated to yield 5-(chloromethyl)-N-(3,4-dichlorobenzyl)pyridin-2-amine, used in the next step without purification. $^1$H NMR (400 MHz, METHANOL-$d_4$) δ ppm 8.05 (1H, dd, J=9.29, 2.01 Hz), 7.92-8.01 (1H, m), 7.54-7.65 (2H, m), 7.36 (1H, dt, J=8.28, 1.00 Hz), 7.04-7.23 (1H, m), 4.65 (1H, s), 4.61 (2H, d, J=2.76 Hz), 4.39 (1H, s). LCMS: R.T.=2.96; [M+H]$^+$=301.02.

6-((6-(3,4-dichlorobenzylamino)pyridin-3-yl)methoxy)quinolin-2(1H)-one

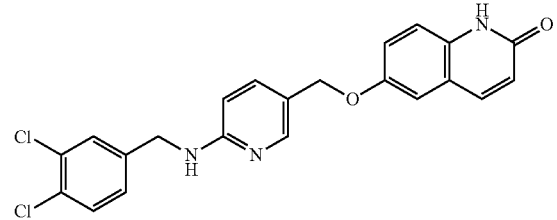 [SMILES: O=c1ccc2cc(OCc3ccc(NCc4ccc(Cl)c(Cl)c4)nc3)ccc2[nH]1]

A mixture of 5-(chloromethyl)-N-(3,4-dichlorobenzyl)pyridin-2-amine (0.1 g, 0.332 mmol), 6-hydroxyquinolin-2(1H)-one (0.048 g, 0.298 mmol) and $Cs_2CO_3$ (0.864 g, 2.65 mmol) in DMF (3.3 mL) was stirred at room temperature for 18 h. The reaction was diluted with water and the resulting suspension was filtered. The filter cake was stirred in methanol for 1 h, filtered, washed with methanol, and dried to yield 6-((6-(3,4-dichlorobenzylamino)pyridin-3-yl)methoxy)quinolin-2(1H)-one as a beige solid (0.033 g, 22%). $^1$H NMR (400 MHz, DMSO-$d_6$) δ ppm 11.65 (1H, s), 8.06 (1H, d, J=2.01 Hz), 7.85 (1H, d, J=9.54 Hz), 7.46-7.63 (3H, m), 7.08-7.37 (5H, m), 6.39-6.62 (2H, m), 4.91 (2H, s), 4.49 (2H, d, J=6.02 Hz). LCMS: R.T.=3.15; [M+H]$^+$=426.00.

The following compounds were synthesized by methods similar to that described for Example 2.

| Example Number | R₁ | R₂ | LCMS RT, min | LCMS Ion [M + H]⁺ | ¹H NMR |
|---|---|---|---|---|---|
| 3 | 4-(difluoromethoxy)phenyl-CH- | quinolin-2(1H)-on-6-yl | 2.93 | 410.16 | ¹H NMR (400 MHz, DMSO-d₆) δ 11.64 (s, 1H), 9.20 (s, 1H), 8.26 (d, J = 2.0 Hz, 1H), 7.86 (d, J = 9.5 Hz, 1H), 7.77-7.60 (m, 3H), 7.39-6.71 (m, 7H), 6.51 (d, J = 9.5 Hz, 1H), 5.02 (s, 2H) |
| 4 | 4-(difluoromethoxy)benzyl | quinolin-2(1H)-on-6-yl | 2.82 | 424.26 | ¹H NMR (400 MHz, DMSO-d₆) δ ppm 11.61 (br. s., 1H), 8.06 (d, J = 2.0 Hz, 1H), 7.84 (d, J = 9.5 Hz, 1H), 7.53-6.90 (m, 10H), 6.52 (dd, J = 17.9, 9.2 Hz, 2H), 4.91 (s, 2H), 4.48 (d, J = 6.0 Hz, 2H) |
| 5 | 3,4-difluorobenzyl | quinolin-2(1H)-on-6-yl | 2.79 | 394.20 | ¹H NMR (400 MHz, DMSO-d₆) δ ppm 11.62 (s, 1H), 8.07 (d, J = 2.3 Hz, 1H), 7.84 (d, J = 9.5 Hz, 1H), 7.51 (dd, J = 8.5, 2.3 Hz, 1H), 7.41-7.29 (m, 3H), 7.27-7.21 (m, 2H), 7.18 (dd, J = 9.0, 2.8 Hz, 2H), 6.56 (d, J = 8.5 Hz, 1H), 6.50 (d, J = 9.5 Hz, 1H), 4.91 (s, 2H), 4.48 (d, J = 6.0 Hz, 2H) |
| 6 | 4-(trifluoromethoxy)benzyl | 8-fluoro-3,4-dihydroquinolin-2(1H)-on-6-yl | 1.96 | 448.1 | ¹H NMR (400 MHz, METHANOL-d₄) δ ppm 8.00 (br. s., 1H), 7.61-7.54 (m, 2H), 7.42 (dd, J = 8.5, 2.3 Hz, 1H), 7.15 (dd, J = 9.2, 0.9 Hz, 2H), 6.73 (d, J = 8.5 Hz, 1H), 6.50-6.47 (m, 1H), 6.42 (dd, J = 14.6, 2.5 Hz, 1H), 5.12 (s, 2H), 2.86-2.78 (m, 2H), 2.67-2.60 (m, 2H) |
| 7 | 4-fluorobenzyl | quinolin-2(1H)-on-6-yl | 2.85 | 376.2 | ¹H NMR (500 MHz, DMSO-d₆) δ ppm 11.63 (s, 1H), 8.05 (d, J = 2.0 Hz, 1H), 7.84 (d, J = 9.6 Hz, 1H), 7.48 (dd, J = 8.5, 2.3 Hz, 1H), 7.40-7.28 (m, 3H), 7.26-7.03 (m, 5H), 6.51 (dd, J = 19.5, 9.0 Hz, 2H), 4.90 (s, 2H), 4.46 (d, J = 6.0 Hz, 2H). |

-continued

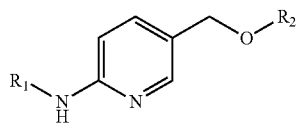

| Example Number | R₁ | R₂ | LCMS RT, min | LCMS Ion [M + H]⁺ | ¹H NMR |
|---|---|---|---|---|---|
| 8 | (3-chlorobenzyl) | (2-oxo-1,2-dihydroquinolin-6-yl) | 2.99 | 392.2 | ¹H NMR (400 MHz, DMSO-d₆) δ ppm 11.66 (s, 1H), 8.06 (d, J = 2.0 Hz, 1H), 7.85 (d, J = 9.5 Hz, 1H), 7.51 (dd, J = 8.7, 2.4 Hz, 1H), 7.42-7.12 (m, 8H), 6.60-6.38 (m, 2H), 4.91 (s, 2H), 4.50 (d, J = 6.0 Hz, 2H). |
| 9 | (4-(trifluoromethoxy)phenyl) | (2-oxo-1,2-dihydroquinolin-6-yl) | 3.18 | 428.2 | ¹H NMR (400 MHz, DMSO-d₆) δ ppm 11.67 (s, 1H), 9.38 (s, 1H), 8.28 (d, J = 2.3 Hz, 1H), 7.93-7.62 (m, 4H), 7.42-7.09 (m, 5H), 6.88 (d, J = 8.5 Hz, 1H), 6.60-6.40 (m, 1H), 5.03 (s, 2H). |
| 10 | (4-(difluoromethoxy)phenyl) | (4-hydroxyphenyl) | 2.82 | 359.2 | ¹H NMR (400 MHz, DMSO-d₆) δ ppm 9.21 (s, 1H), 8.95 (s, 1H), 8.20 (d, J = 2.3 Hz, 1H), 7.76-7.69 (m, 2H), 7.64 (dd, J = 8.5, 2.5 Hz, 1H), 7.35-6.89 (m, 3H), 6.84 (d, J = 9.0 Hz, 3H), 6.76-6.61 (m, 2H), 4.87 (s, 2H). |

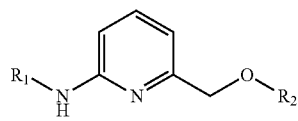

| Example Number | R₁ | R₂ | LCMS RT, min | LCMS Ion [M + H]⁺ | ¹H NMR |
|---|---|---|---|---|---|
| 11 | (4-chlorophenyl) | (2-oxo-1,2-dihydroquinolin-6-yl) | 3.46 | 378.2 | ¹H NMR (400 MHz, DMSO-d₆) δ ppm 11.68 (br. s., 1H), 9.29 (s, 1H), 7.85 (d, J = 9.5 Hz, 1H), 7.79-7.67 (m, 2H), 7.63 (dd, J = 8.2, 7.4 Hz, 1H), 7.42-7.19 (m, 5H), 6.92 (d, J = 7.3 Hz, 1H), 6.78 (d, J = 8.3 Hz, 1H), 6.50 (d, J = 9.5 Hz, 1H), 5.14 (s, 2H) |

Example 12

4-((2-(4-chlorophenylamino)pyrimidin-5-yl)methoxy)phenol

Ethyl 2-(4-chlorophenylamino)pyrimidine-5-carboxylate

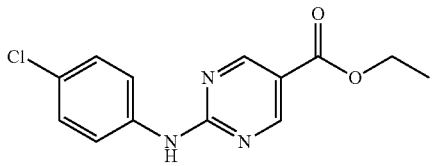 [SMILES: CCOC(=O)c1cnc(Nc2ccc(Cl)cc2)nc1]

A mixture of ethyl 2-chloropyrimidine-5-carboxylate (0.5 g, 2.68 mmol) and 4-chloroaniline (0.684 g, 5.36 mmol) in dioxane (15 mL) was heated at 100° C. for 8 h, diluted with ethyl acetate and filtered. The filtrate was concentrated and the residue was purified by flash chromatography on silica gel using 0-30% ethyl acetate in hexanes. The desired fractions were concentrated to give ethyl 2-(4-chlorophenylamino)pyrimidine-5-carboxylate as an orange solid (0.43 g, 58%). $^1$H NMR (500 MHz, CHLOROFORM-d) δ ppm 8.96 (2H, s), 7.57-7.64 (2H, m), 7.45 (1H, br. s.), 7.29-7.36 (2H, m), 4.37 (2H, q, J=7.02 Hz), 1.38 (3H, t, J=7.02 Hz). LCMS: R.T.=4.16 min; [M+H]$^+$=277.96.

(2-(4-chlorophenylamino)pyrimidin-5-yl)methanol

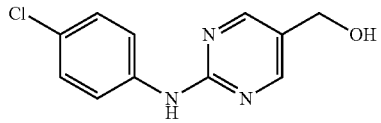 [SMILES: OCc1cnc(Nc2ccc(Cl)cc2)nc1]

A solution of ethyl 2-(4-chlorophenylamino)pyrimidine-5-carboxylate (0.43 g, 1.548 mmol) in THF (10 mL) was cooled at −78° C. and 1M solution of DIBAL-H (4.65 ml, 4.65 mmol) in toluene was added. The mixture was stirred for 1.5 h while warming to room temperature. The reaction mixture was diluted with THF (20 mL) and quenched with Na$_2$SO$_4$.10H$_2$O followed by a few drops of water. The mixture was stirred at room temperature for 18 h, then filtered through a pad of Celite topped with silica gel. The pad was washed with ethyl acetate and the filtrate was concentrated. The residue was purified by flash chromatography on silica gel using 45-80% ethyl acetate in hexanes. The desired fractions were concentrated to give (2-(4-chlorophenylamino) pyrimidin-5-yl)methanol as a white solid (0.26 g, 71%). $^1$H NMR (400 MHz, CHLOROFORM-d) δ ppm 8.46 (2H, s), 7.53-7.63 (2H, m), 7.28-7.34 (2H, m), 7.17 (1H, br. s.), 4.64 (2H, d, J=5.52 Hz). LCMS: R.T.=3.24 min; [M+H]$^+$=235.97

5-(chloromethyl)-N-(4-chlorophenyl)pyrimidin-2-amine

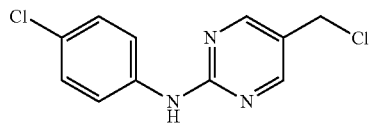

Thionyl chloride (0.427 mL, 5.86 mmol) was added to a suspension of (2-((4-chlorophenyl)amino)pyrimidin-5-yl) methanol (0.23 g, 0.976 mmol) in DCM (10 mL) cooled to 0° C. The mixture was stirred for 18 h while warming to room temperature. The reaction mixture was concentrated and the residue triturated with ether to give 5-(chloromethyl)-N-(4-chlorophenyl)pyrimidin-2-amine as a pale yellow solid (0.28 g, 99%). $^1$H NMR (400 MHz, DMSO-d$_6$) δ ppm 10.03 (s, 1H), 8.60 (s, 2H), 7.85-7.64 (m, 2H), 7.41-7.20 (m, 2H), 4.77 (s, 2H).

4-((2-(4-chlorophenylamino)pyrimidin-5-yl)methoxy)phenol trifluoroacetate

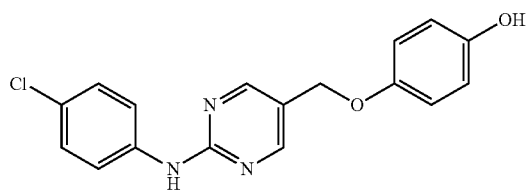 [SMILES: Oc1ccc(OCc2cnc(Nc3ccc(Cl)cc3)nc2)cc1]

A mixture of 5-(chloromethyl)-N-(4-chlorophenyl)pyrimidin-2-amine hydrochloride (0.14 g, 0.482 mmol), Cs$_2$CO$_3$ (0.628 g, 1.927 mmol) and 4-((tert-butyldimethylsilyl)oxy) phenol (0.108 g, 0.482 mmol) in DMF was stirred at room temperature for 18 h. The reaction mixture was diluted with water and filtered. The crude product was purified by preparative HPLC on a Xterra C18 (5 μm, 30×100 mm) reversed phase column using 30-100% of mobile phase B (90% methanol/10% water/0.1% TFA) in mobile phase A (10% methanol/90% water/0.1% TFA). The desired peak was concentrated to give 4-((2-(4-chlorophenylamino)pyrimidin-5-yl)methoxy) phenol trifluoroacetate as a pale yellow solid (0.059 g, 26%). $^1$H NMR (400 MHz, DMSO-d$_6$) δ ppm 9.93 (s, 1H), 8.99 (br. s., 1H), 8.58 (s, 2H), 7.82 (d, J=9.0 Hz, 2H), 7.35 (d, J=9.0 Hz, 2H), 6.86 (d, J=9.0 Hz, 2H), 6.70 (d, J=8.8 Hz, 2H), 4.91 (s, 2H). LCMS: R.T.=3.71; [M+H]$^+$=328.14

Example 13

4-((2-(3,4-dichlorophenylamino)pyrimidin-5-yl)methoxy)phenol 5-((4-(tert-butyldimethylsilyloxy)phenoxy)methyl)-N-(3,4-dichlorophenyl)pyrimidin-2-amine

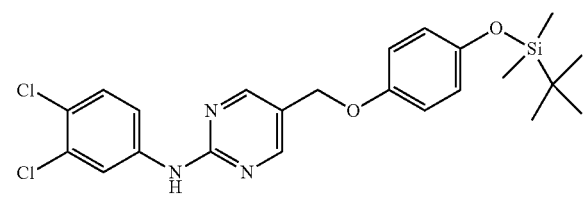 [SMILES: CC(C)(C)[Si](C)(C)Oc1ccc(OCc2cnc(Nc3ccc(Cl)c(Cl)c3)nc2)cc1]

A mixture of 4-((tert-butyldimethylsilyl)oxy)phenol (0.086 g, 0.381 mmol), Cs$_2$CO$_3$ (0.186 g, 0.572 mmol) and 5-(chloromethyl)-N-(3,4-dichlorophenyl)pyrimidin-2-amine (0.110 g, 0.381 mmol) in DMF (3.8 mL) was stirred at room temperature for 18 h. The reaction mixture was concentrated and purified by flash chromatography on silica gel using 10-50% ethyl acetate in hexanes. The desired fractions were concentrated to give 5-((4-(tert-butyldimethylsilyloxy) phenoxy)methyl)-N-(3,4-dichlorophenyl)pyrimidin-2-amine as a yellow solid (0.022 g, 12%). LCMS: R.T.=3.73 min; [M+H]$^+$=476.23

4-((2-(3,4-dichlorophenylamino)pyrimidin-5-yl)methoxy)phenol

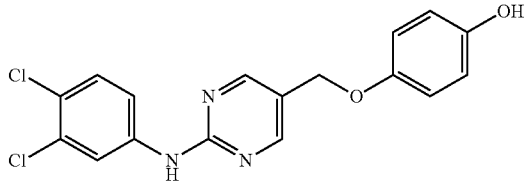 [SMILES: Oc1ccc(OCc2cnc(Nc3ccc(Cl)c(Cl)c3)nc2)cc1]

5-((4-((tert-butyldimethylsilyl)oxy)phenoxy)methyl)-N-(3,4-dichlorophenyl)pyrimidin-2-amine (0.022 g, 0.046 mmol) was dissolved in THF (4.6 mL) and TBAF (0.231 ml, 0.231 mmol) was added. The mixture was stirred at room temperature for 16 h, quenched with ammonium chloride solution and extracted with ethyl acetate. The organic extract was dried over $Na_2SO_4$ and concentrated. The residue was purified by flash chromatography on silica gel using 20-50% ethyl acetate in hexanes. The desired fractions were concentrated to give 4-((2-(3,4-dichlorophenylamino)pyrimidin-5-yl)methoxy)phenol as a white solid (0.006 g, 34%). $^1$H NMR (400 MHz, CHLOROFORM-d) δ ppm 8.52 (2H, s), 7.99 (1H, dd, J=1.88, 0.88 Hz), 7.33-7.45 (2H, m), 7.23 (1H, s), 6.82-6.90 (2H, m), 6.71-6.84 (2H, m), 4.91 (2H, s), 4.65 (1H, br. s.). LCMS: R.T.=1.04 min; [M+H]$^+$=362.04

Example 14

6-((2-(4-chlorophenylamino)pyrimidin-5-yl)methoxy)quinolin-2(1H)-one

5-(chloromethyl)-N-(4-chlorophenyl)pyrimidin-2-amine

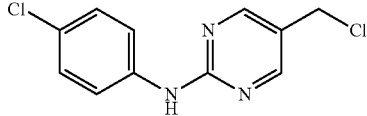 [SMILES: ClCc1cnc(Nc2ccc(Cl)cc2)nc1]

A suspension of (2-(4-chlorophenylamino)pyrimidin-5-yl)methanol (0.15 g, 0.636 mmol) and $Et_3N$ (0.177 ml, 1.273 mmol) in DCM (6.4 mL) was cooled to 0° C. and methanesulfonyl chloride (0.099 mL, 1.273 mmol) was added. The reaction was stirred for 1.5 h while warming to room temperature. The mixture was diluted with DCM and quenched with sat. $NaHCO_3$. The organic layer was isolated and dried over $Na_2SO_4$, then concentrated to give crude 5-(chloromethyl)-N-(4-chlorophenyl)pyrimidin-2-amine as a yellow solid (0.1 g, 62%). $^1$H NMR (400 MHz, CHLOROFORM-d) δ ppm 8.46 (2H, s), 7.58 (2H, d, J=8.78 Hz), 7.31 (2H, d, J=8.78 Hz), 7.25 (1H, br. s.), 4.53 (2H, s).

6-((2-(4-chlorophenylamino)pyrimidin-5-yl)methoxy)quinolin-2(1H)-one

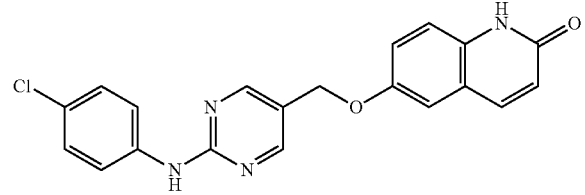 [SMILES: O=c1ccc2cc(OCc3cnc(Nc4ccc(Cl)cc4)nc3)ccc2[nH]1]

A mixture of 6-hydroxyquinolin-2(1H)-one (0.057 g, 0.354 mmol), $Cs_2CO_3$ (0.192 g, 0.590 mmol) and 5-(chloromethyl)-N-(4-chlorophenyl)pyrimidin-2-amine (0.1 g, 0.394 mmol) in DMF (2.5 mL) was stirred at room temperature for 18 h. The reaction was diluted with water and the resulting suspension filtered. The bright yellow filter cake was taken up in methanol and the mixture was stirred for 1 h. The suspension was filtered and the yellow solid was washed with methanol and dried. The solid was further stirred in DCM/MeOH for 2 days. The mixture was filtered, and the filter cake washed with methanol and dried to give 6-((2-(4-chlorophenylamino)pyrimidin-5-yl)methoxy)quinolin-2 (1H)-one as a brown solid (0.04 g, 26%). $^1$H NMR (400 MHz, DMSO-$d_6$) δ ppm 11.68 (1H, s), 9.95 (1H, s), 8.64 (2H, s), 7.72-7.92 (3H, m), 7.12-7.47 (5H, m), 6.52 (1H, d, J=9.54 Hz), 5.04 (2H, s). LCMS: R.T.=3.77 min; [M+H]$^+$=378.93.

Example 15

N-(4-(trifluoromethoxy)phenyl)-5-(((3-(trifluoromethyl)-1H-indazol-5-yl)oxy)methyl)pyrimidin-2-amine

5-bromo-1-(tetrahydro-2H-pyran-2-yl)-3-(trifluoromethyl)-1H-indazole

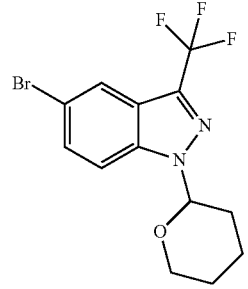 [SMILES: FC(F)(F)c1nn(C2CCCCO2)c2ccc(Br)cc12]

To a solution of 5-bromo-3-(trifluoromethyl)-1H-indazole (500 mg, 1.887 mmol) in DCM (10 mL) was added 3,4-dihydro-2h-pyran (0.517 mL, 5.66 mmol) and p-toluenesulfonic acid monohydrate (35.9 mg, 0.189 mmol). The solution was stirred for 1 h. The solution was diluted with DCM, washed with saturated $NaHCO_3$ and concentrated. The residue was purified by flash chromatography on silica gel with eluting with 10% EtOAc/Hexane to give 5-bromo-1-(tetrahydro-2H-pyran-2-yl)-3-(trifluoromethyl)-1H-indazole as a colorless oil (610 mg, 93%). $^1$NMR: 400 MHz, CDCl$_3$: δ ppm 1.69-1.75 (m, 7H), 2.12-2.17 (m, 2H), 2.48-2.51 (m, 1H), 3.61 (d, J=85.20 Hz, 3H), 3.72-3.78 (m, 2H), 3.87-3.99 (m, 3H), 4.56 (s, 1H), 5.77 (dd, J=4.00, 8.00 Hz, 1H), 7.52-7.60 (m, 2H), 7.96 (t, J=24.40 Hz, 1H).

1-(tetrahydro-2H-pyran-2-yl)-5-(4,4,5,5-tetramethyl-1,3,2-dioxaborolan-2-yl)-3-(trifluoromethyl)-1H-indazole

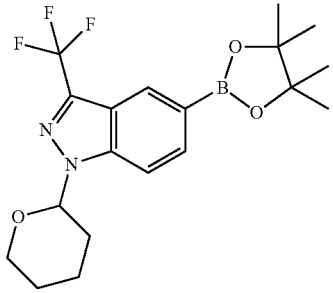 [SMILES: CC1(C)OB(c2ccc3c(c2)c(C(F)(F)F)nn3C2CCCCO2)OC1(C)C]

To a solution of 5-bromo-1-(tetrahydro-2H-pyran-2-yl)-3-(trifluoromethyl)-1H-indazole (300 mg, 0.859 mmol), potassium acetate (253 mg, 2.58 mmol), bis(pinacolato)diboron (545 mg, 2.148 mmol) in dry DMSO were added PdCl2(dppf) (7.02 mg, 8.59 μmol) under inert atmosphere. The reaction mixture was heated at 90° C. for overnight, then diluted with water and extracted with ethyl acetate. The organic layer was washed with water and brine, passed through celite and dried over Na$_2$SO$_4$. The crude product was purified by flash chromatography on silica gel using with 10% EtOAc/Hexanes to give 1-(tetrahydro-2H-pyran-2-yl)-5-(4,4,5,5-tetramethyl-1,3,2-dioxaborolan-2-yl)-3-(trifluoromethyl)-1H-indazole as a colorless oil (245 mg, 72% yield). $^1$NMR: 400 MHz, CDCl$_3$: δ ppm 1.37 (s, 13H), 1.68-1.79 (m, 5H), 2.06-2.18 (m, 2H), 2.55 (t, J=6.80 Hz, 1H), 3.72-3.78 (m, 1H), 3.98-4.03 (m, 1H), 5.79 (dd, J=2.80, 8.80 Hz, 1H), 7.64 (dd, J=0.80, 8.40 Hz, 1H), 7.86 (dd, J=0.80, 8.40 Hz, 1H), 8.33 (d, J=0.80 Hz, 1H).

1-(tetrahydro-2H-pyran-2-yl)-3-(trifluoromethyl)-1H-indazol-5-ol

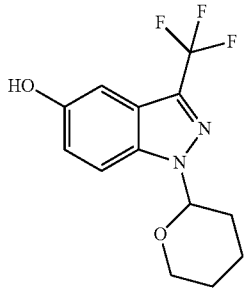 [SMILES: Oc1ccc2c(c1)c(C(F)(F)F)nn2C1CCCCO1]

To a solution of 1-(tetrahydro-2H-pyran-2-yl)-5-(4,4,5,5-tetramethyl-1,3,2-dioxaborolan-2-yl)-3-(trifluoromethyl)-1H-indazole (415 mg, 1.047 mmol) in THF (4 mL) and water (4.00 mL) was added sodium perborate tetrahydrate (483 mg, 3.14 mmol). The reaction mixture was heated at 50° C. for 2 h. The organic solvents were evaporated, extracted with EtOAc and washed with water and brine solution, then dried over Na$_2$SO$_4$ and concentrated. The crude product was purified by flash chromatography on silica gel using 50% EtOAc/Petroleum Ether to give 1-(tetrahydro-2H-pyran-2-yl)-3-(trifluoromethyl)-1H-indazol-5-ol (255 mg, 85%). $^1$HNMR 400 MHz, CDCl$_3$: δ ppm 1.68-1.75 (m, 4H), 2.05-2.17 (m, 2H), 2.46-2.52 (m, 1H), 3.71-3.77 (m, 1H), 3.98-4.01 (m, 1H), 4.89 (s, 1H), 5.74 (dd, J=2.40, 9.00 Hz, 1H), 7.08 (dd, J=2.40, 9.00 Hz, 1H), 7.13 (d, J=0.80 Hz, 1H), 7.59 (d, J=0.40 Hz, 1H).

5-(((1-(tetrahydro-2H-pyran-2-yl)-3-(trifluoromethyl)-1H-indazol-5-yl)oxy)methyl)-N-(4-(trifluoromethoxy)phenyl)pyrimidin-2-amine

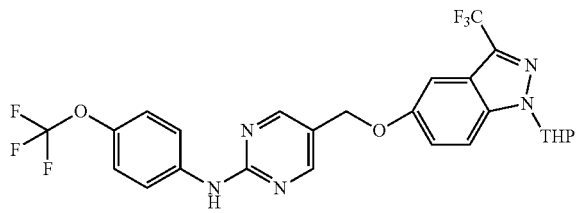

To a solution of 5-(chloromethyl)-N-(4-(trifluoromethoxy)phenyl)pyrimidin-2-amine (0.04 g, 0.132 mmol) in DMF (2 mL), 1-(tetrahydro-2H-pyran-2-yl)-3-(trifluoromethyl)-1H-indazol-5-ol (0.045 g, 0.158 mmol) and Cs$_2$CO$_3$ (0.086 g, 0.263 mmol) were added. The reaction mixture was stirred at room temperature for 18 h, then diluted in EtOAc and washed sequentially with 10% NaOH and brine. The organic layer was dried over Na$_2$SO$_4$ and concentrated to afford 5-(((1-(tetrahydro-2H-pyran-2-yl)-3-(trifluoromethyl)-1H-indazol-5-yl)oxy)methyl)-N-(4-(trifluoromethoxy)phenyl)pyrimidin-2-amine (38 mg, 52%). LCMS: RT 2.33 min; 554.0 [M+H]$^+$.

N-(4-(trifluoromethoxy)phenyl)-5-(((3-(trifluoromethyl)-1H-indazol-5-yl)oxy)methyl)pyrimidin-2-amine

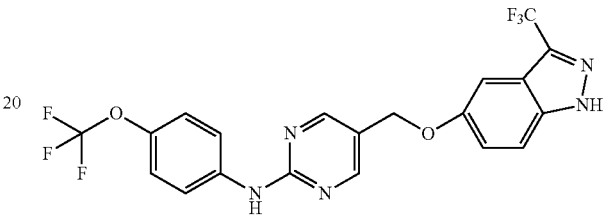

To a solution of 5-(((1-(tetrahydro-2H-pyran-2-yl)-3-(trifluoromethyl)-1H-indazol-5-yl)oxy)methyl)-N-(4-(trifluoromethoxy)phenyl)pyrimidin-2-amine (0.03 g, 0.054 mmol) in DCM (5 mL) at 0° C., TFA (2 mL, 26.0 mmol) was added. The reaction mixture was stirred at room temperature for 5 h. Solvent was removed under vacuum and the crude product was purified by preparative HPLC on an Inertsil ODS column (19×250 mm, 5μ) using 0-65% mobile phase B (ACN) in mobile phase A (0.1% TFA) over 6 min to give N-(4-(trifluoromethoxy)phenyl)-5-(((3-(trifluoromethyl)-1H-indazol-5-yl)oxy)methyl)pyrimidin-2-amine as an off-white solid (10 mg, 39%). $^1$HNMR 400 MHz, DMSO-d6: δ ppm 5.11 (s, 1H), 7.22-7.22 (m, 1H), 7.29-7.30 (m, 3H), 7.65 (d, J=9.20 Hz, 1H), 7.86-7.87 (m, 2H), 8.67 (s, 2H), 10.00 (s, 1H), 13.90-0.00 (m, 1H). LCMS: R.T.=2.13 min; [M+H]$^+$=468.0.

Example 16

6-((2-((4-(difluoromethoxy)phenyl)amino)pyrimidin-5-yl)methoxy)benzo[d]oxazol-2(3H)-one 6-hydroxy-3-((2-(trimethylsilyl)ethoxy)methyl)benzo[d]oxazol-2(3H)-one

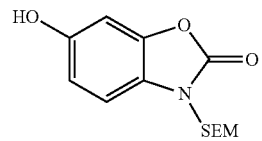 [SMILES: C[Si](C)(C)CCOCn1c(=O)oc2cc(O)ccc21]

To a solution of 6-hydroxybenzo[d]oxazol-2(3H)-one (3 g, 19.85 mmol) in dry DMF (30 mL), K$_2$CO$_3$ (5.54 g, 40.1 mmol) and SEM-Cl (4.79 mL, 27.0 mmol) were added. The reaction mixture was stirred at room temperature for 18 h. Solvent was removed under vacuum. The residue was dissolved in ethyl acetate, washed with water and brine, and dried over sodium sulfate. The organic layer was concentrated under vacuum and the crude product was purified by flash chromatography on silica gel using 10 to 50% ethyl acetate in hexane to give 6-hydroxy-3-((2-(trimethylsilyl)ethoxy)methyl)benzo[d]oxazol-2(3H)-one as an white solid (1.2 g, 21%). ¹HNMR 400 MHz, DMSO-d6: δ ppm −0.055 (s, 9H), 0.86 (t, J=8.00 Hz, 2H), 3.58 (t, J=8.00 Hz, 2H), 5.19 (s, 2H), 6.64 (dd, J=2.40, 8.40 Hz, 1H), 6.78 (d, J=2.00 Hz, 1H), 7.10 (d, J=8.40 Hz, 1H), 9.52 (s, 1H). LCMS: R.T. 1.845 min; 280.1 [M−H].

6-((2-((4-(trifluoromethoxy)phenyl)amino)pyrimidin-5-yl)methoxy)-3-((2-(trimethylsilyl)ethoxy)methyl)benzo[d]oxazol-2(3H)-one

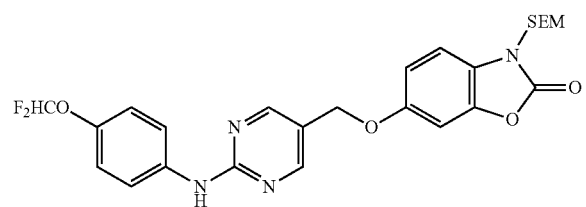 [SMILES: C[Si](C)(C)CCOCn1c(=O)oc2cc(OCc3cnc(Nc4ccc(OC(F)F)cc4)nc3)ccc21]

To a solution of 6-hydroxy-3-((2-(trimethylsilyl)ethoxy)methyl)benzo[d]oxazol-2(3H)-one (0.093 g, 0.329 mmol) in DMF (4 mL) was add cesium carbonate (0.322 g, 0.988 mmol) and 5-(chloromethyl)-N-(4-(trifluoromethoxy)phenyl)pyrimidin-2-amine (0.1 g, 0.329 mmol). The reaction mixture was stirred at room temperature for 18 h. Solvent was removed under vacuum. The residue was dissolved in ethyl acetate, and washed with 10% NaOH solution, water, and brine. The organic layer was dried over anhydrous sodium sulfate, filtered, and concentrated. The crude product was purified by flash chromatography on silica gel using 20 to 80% ethyl acetate in hexanes to give 6-((2-((4-(trifluoromethoxy)phenyl)amino)pyrimidin-5-yl)methoxy)-3-((2-(trimethylsilyl)ethoxy)methyl)benzo[d]oxazol-2(3H)-one as an white solid (0.07 g, 39%). LCMS: RT 2.216 min; 529.2 [M−H].

3-(hydroxymethyl)-6-((2-((4-(trifluoromethoxy)phenyl)amino)pyrimidin-5-yl)methoxy)benzo[d]oxazol-2(3H)-one

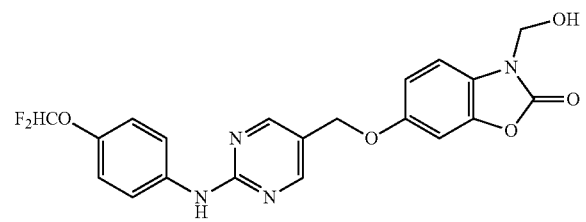 [SMILES: O=c1oc2cc(OCc3cnc(Nc4ccc(OC(F)F)cc4)nc3)ccc2n1CO]

To a solution of 6-((2-((4-(trifluoromethoxy)phenyl)amino)pyrimidin-5-yl)methoxy)-3-((2-(trimethylsilyl)ethoxy)methyl)benzo[d]oxazol-2(3H)-one (0.05 g, 0.091 mmol) in DCM (3 mL) at 0° C., TFA (0.035 mL, 0.456 mmol) was added. The reaction mixture was stirred at room temperature for 18 h. Solvent was removed under vacuum and the residue was washed with diethyl ether. The crude product was purified by preparative HPLC on an Inertsil ODS column (19×250 mm, 5μ) using 0 to 65% mobile phase B (ACN) in mobile phase A (0.1% TFA) over 6 min to give 3-(hydroxymethyl)-6-((2-((4-(trifluoromethoxy)phenyl)amino)pyrimidin-5-yl)methoxy)benzo[d]oxazol-2(3H)-one as a white solid (0.025 g, 61%). ¹H-NMR: 400 MHz, DMSO-d6 δ ppm 5.03 (s, 2H), 5.19 (s, 2H), 6.92-6.95 (m, 1H), 7.21-7.32 (m, 4H), 7.86-7.88 (m, 1H), 8.62 (s, 2H), 9.96 (s, 1H). LCMS: R.T. 2.303 min; 449 [M+H]⁺.

6-((2-((4-(difluoromethoxy)phenyl)amino)pyrimidin-5-yl)methoxy)benzo[d]oxazol-2(3H)-one

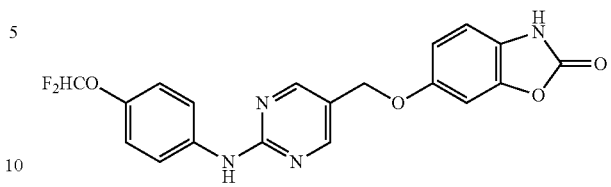

6-((2-((4-(difluoromethoxy)phenyl)amino)pyrimidin-5-yl)methoxy)-3-(hydroxymethyl)benzo[d]oxazol-2(3H)-one (0.011 g, 0.026 mmol) was dissolved in a mixture of methanol (2 mL) and water (2 mL). The reaction mixture was sonicated for 15 min. Solvent was concentrated and the residue was lyophilized to give 6-((2-((4-(difluoromethoxy)phenyl)amino)pyrimidin-5-yl)methoxy)benzo[d]oxazol-2(3H)-one as a white solid (0.009 g, 87% yield). ¹H NMR (400 MHz, DMSO-d6) δ ppm 4.99 (s, 2H) 6.82 (dd, J=8.53, 2.26 Hz, 1H) 6.94-7.32 (m, 5H) 7.79 (s, 2H) 8.59 (br. s., 2H) 9.84 (s, 1H) 11.42-11.50 (m, 1H). LCMS: R.T.=0.84 min; [M+H]⁺= 401.0.

Example 17

5-((2-aminopyrimidin-5-yloxy)methyl)-N-(4-(difluoromethoxy)phenyl)pyrimidin-2-amine

5-(benzyloxy)pyrimidin-2-amine

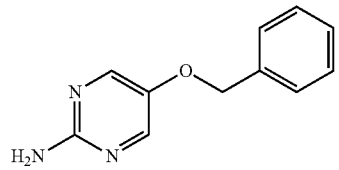 [SMILES: Nc1ncc(OCc2ccccc2)cn1]

To the solution of 2-aminopyrimidin-5-ol (0.500 g, 4.50 mmol) in dry MeOH (10 mL), K₂CO₃ (0.622 g, 4.50 mmol) and benzyl bromide (0.535 mL, 4.50 mmol) were added. The reaction mixture was stirred at room temperature for 18 h. Solvent was removed under reduced pressure. The residue was dissolved in ethyl acetate and washed with water and brine, then dried over sodium sulfate. The crude product was purified by flash chromatography on silica gel using 50% ethyl acetate in petroleum ether. The desired fractions were concentrated to give 5-(benzyloxy)pyrimidin-2-amine as an off-white solid (0.222 g 25%). ¹HNMR 400 MHz, DMSO-d6: δ ppm 5.06 (s, 2H), 6.21 (s, 2H), 7.28-7.30 (m, 5H), 7.45 (s, 2H). LCMS: RT 1.060 min; 202.2 (M+H).

di-tert-butyl (5-(benzyloxy)pyrimidin-2-yl)biscarbamate

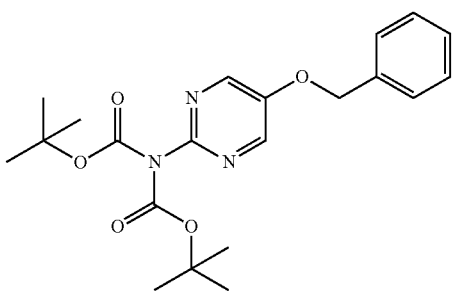 [SMILES: CC(C)(C)OC(=O)N(C(=O)OC(C)(C)C)c1ncc(OCc2ccccc2)cn1]

To the solution of 5-(benzyloxy)pyrimidin-2-amine (0.222 g, 1.103 mmol) in DCM (10 mL), BOC$_2$O (0.538 mL, 2.317 mmol) and DMAP (0.013 g, 0.110 mmol) were added. The reaction mixture was stirred at room temperature for 18 h. The reaction mixture was diluted with DCM (50 mL) and washed with water and brine, then dried over sodium sulfate and concentrated under vacuum. The crude product was purified by flash chromatography on silica gel using 30% ethyl acetate in hexane. The desired fractions were concentrated to give di-tert-butyl (5-(benzyloxy)pyrimidin-2-yl)biscarbamate as an off-white solid (0.37 g, 84%).

$^1$HNMR 300 MHz, DMSO-d6: δ 1.37 (s, 18H), 5.32 (s, 2H), 7.36-7.38 (m, 5H), 8.65 (s, 2H).

di-tert-butyl (5-hydroxypyrimidin-2-yl)biscarbamate

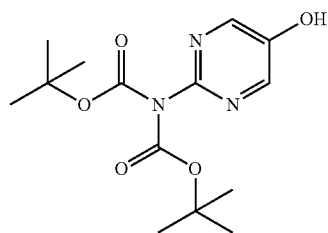 [SMILES: CC(C)(C)OC(=O)N(C(=O)OC(C)(C)C)c1ncc(O)cn1]

To a solution of di-tert-butyl (5-(benzyloxy)pyrimidin-2-yl)biscarbamate (370 mg, 0.922 mmol) in dry MeOH (10 mL), Pd/C (49.0 mg, 0.046 mmol) was added and the reaction mixture was stirred under a H$_2$ ballon for 18 h. The reaction mixture was filtered through Celite and the filtrate was concentrated under vacuum to give di-tert-butyl (5-hydroxypyrimidin-2-yl)biscarbamate as an off-white solid (0.2 g, 70%).
$^1$HNMR 400 MHz, DMSO-d6: δ 1.37 (s, 18H), 8.35 (s, 2H), 10.71 (s, 1H).

di-tert-butyl (5-((2-((4-(difluoromethoxy)phenyl)amino)pyrimidin-5-yl)methoxy)pyrimidin-2-yl)biscarbamate

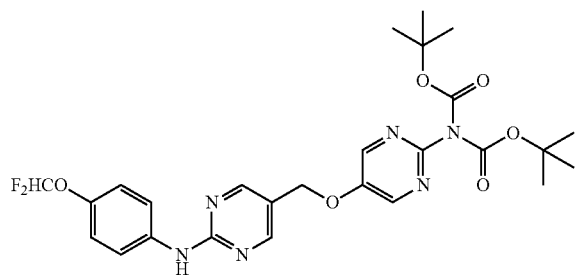 [SMILES: CC(C)(C)OC(=O)N(C(=O)OC(C)(C)C)c1ncc(OCc2cnc(Nc3ccc(OC(F)F)cc3)nc2)cn1]

To a solution of di-tert-butyl (5-hydroxypyrimidin-2-yl)biscarbamate (120 mg, 0.385 mmol) in dry DMF (10 mL), Cs$_2$CO$_3$ (251 mg, 0.771 mmol) was added. The reaction mixture was stirred at room temperature for 5 minutes, then 5-(chloromethyl)-N-(4-(difluoromethoxy)phenyl)pyrimidin-2-amine (110 mg, 0.385 mmol) was added and the reaction mixture was stirred at room temperature for 18 h. Solvent was removed under vacuum. The residue was dissolved in ethyl acetate and washed with water and brine, then dried over sodium sulfate. Solvent was removed under vacuum to give crude di-tert-butyl (5-((2-((4-(difluoromethoxy)phenyl)amino)pyrimidin-5-yl)methoxy)pyrimidin-2-yl)biscarbamate (0.08 g, 24%). LCMS: RT 2.077 min; 561.219 (M+H).

5-((2-aminopyrimidin-5-yloxy)methyl)-N-(4-(difluoromethoxy)phenyl)pyrimidin-2-amine

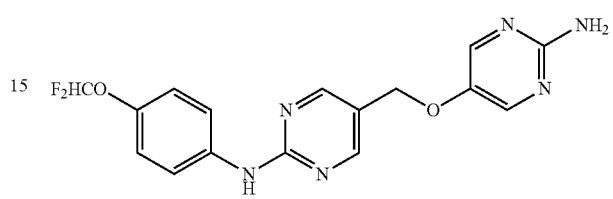

To a solution of crude di-tert-butyl (5-((2-((4-(difluoromethoxy)phenyl)amino)pyrimidin-5-yl)methoxy)pyrimidin-2-yl)biscarbamate (80 mg, 0.143 mmol) in DCM (10 mL), TFA (0.055 mL, 0.714 mmol) was added. The reaction mixture was stirred at room temperature for 2 h. Solvent was removed under vacuum. The crude product was purified by preparative HPLC on an Atlantis DC18 (250×19×10 m) C18 column using 0-100% of mobile phase B (Acetonitrile) in mobile phase A (0.1% TFA) over 23 min. The desired peak was concentrated to give 5-((2-aminopyrimidin-5-yloxy)methyl)-N-(4-(difluoromethoxy)phenyl)pyrimidin-2-amine as an off-white solid (15.2 mg, 27%). $^1$H NMR (400 MHz, DMSO-d6) δ ppm 4.87-5.00 (m, 2H) 6.23-6.53 (m, 1H) 6.92-7.33 (m, 4H) 7.70-7.84 (m, 2H) 8.11-8.20 (m, 2H) 8.45-8.62 (m, 2H) 9.79-9.79 (m, 1H). LCMS: R.T.=1.9 min; [M+H]$^+$= 361.2.

Example 18

6-((2-((4-(difluoromethoxy)phenyl)amino)-4-methoxypyrimidin-5-yl)methoxy)quinolin-2(1H)-one Mixture of methyl 4-methoxy-2-(methylthio)pyrimidine-5-carboxylate and ethyl 4-methoxy-2-(methylthio)pyrimidine-5-carboxylate

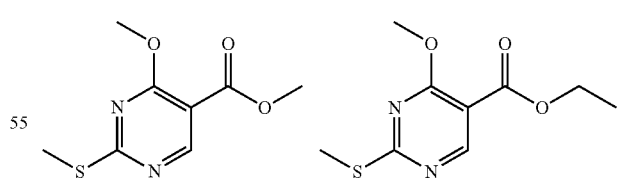

A mixture of ethyl 4-chloro-2-(methylthio)pyrimidine-5-carboxylate (2.5 g, 10.74 mmol) and sodium methoxide (2.50 mL, 13.11 mmol) in methanol (107 mL) was stirred at room temperature under nitrogen for 4 h, quenched with acetic acid (5 mL), and concentrated. The oily residue was purified by flash chromatography on silica gel using 0-40% ethyl acetate in hexanes to give methyl 4-methoxy-2-(methylthio)pyrimidine-5-carboxylate as a white solid (0.52 g, 23%) and ethyl 4-methoxy-2-(methylthio)pyrimidine-5-carboxylate as a colorless oil (0.61 g, 25%). Methyl 4-methoxy-2-(methylthio)pyrimidine-5-carboxylate: $^1$H NMR (400 MHz, CHLOROFORM-d) δ ppm 8.83 (s, 1H), 4.11 (s, 3H), 3.90 (s, 3H), 2.60 (s, 3H). LCMS: R.T.=0.92; [M+H]$^+$=229.1. Ethyl 4-methoxy-2-(methylthio)pyrimidine-5-carboxylate: $^1$H NMR (400 MHz, CHLOROFORM-d) δ 8.82 (s, 1H), 4.36 (q, J=7.0 Hz, 2H), 4.11 (s, 3H), 2.60 (s, 3H), 1.38 (t, J=7.2 Hz, 3H). LCMS: R.T.=0.92; [M+H]$^+$=229.1.

Ethyl 4-methoxy-2-(methylsulfonyl)pyrimidine-5-carboxylate

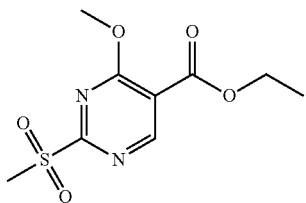 [SMILES: CCOC(=O)c1cnc(S(C)(=O)=O)nc1OC]

A mixture of ethyl 4-methoxy-2-(methylthio)pyrimidine-5-carboxylate (0.60 g, 2.63 mmol), $H_2O_2$ (1.21 mL, 11.83 mmol) and formic acid (0.20 mL, 5.26 mmol) in DCM (26 mL) was stirred at room temperature for 18 h. The reaction mixture was cooled in an ice/water bath and carefully quenched with a cold saturated solution of sodium sulfite. The mixture was extracted with DCM. The organic layer was dried over $Na_2SO_4$ and concentrated to give ethyl 4-methoxy-2-(methylsulfonyl)pyrimidine-5-carboxylate as a viscous oil (0.45 g, 66%). $^1$H NMR (500 MHz, CHLOROFORM-d) δ ppm 9.08 (s, 1H), 4.45 (q, J=7.1 Hz, 2H), 4.24 (s, 3H), 3.38 (s, 3H), 1.43 (t, J=7.2 Hz, 3H). LCMS: R.T.=0.71; [M+H]$^+$=261.1.

Ethyl 2-((4-(difluoromethoxy)phenyl)amino)-4-methoxypyrimidine-5-carboxylate

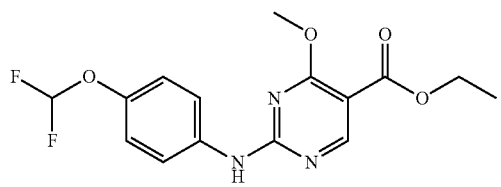 [SMILES: CCOC(=O)c1cnc(Nc2ccc(OC(F)F)cc2)nc1OC]

A mixture of 4-(difluoromethoxy)aniline (0.285 mL, 2.305 mmol) and ethyl 4-methoxy-2-(methylsulfonyl)pyrimidine-5-carboxylate (0.4 g, 1.537 mmol) in dioxane was heated in the microwave at 150° C. for 50 min. The mixture was then cooled to room temperature and concentrated. The residue was purified by flash chromatography on silica gel using 5-50% ethyl acetate in hexanes. The desired fractions were concentrated to give ethyl 2-((4-(difluoromethoxy)phenyl)amino)-4-methoxypyrimidine-5-carboxylate as an orange solid (0.37 g, 71%). $^1$H NMR (400 MHz, CHLOROFORM-d) δ ppm 8.83 (s, 1H), 7.67-7.58 (m, 2H), 7.37 (br. s., 1H), 7.20-7.09 (m, 2H), 6.74-6.12 (m, 1H), 4.35 (q, J=7.0 Hz, 2H), 4.08 (s, 3H), 1.38 (t, J=7.0 Hz, 3H). LCMS: R.T.=0.96; [M+H]$^+$=340.1.

(2-((4-(difluoromethoxy)phenyl)amino)-4-methoxypyrimidin-5-yl)methanol

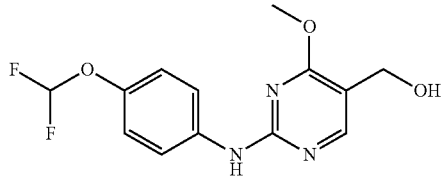 [SMILES: COc1nc(Nc2ccc(OC(F)F)cc2)ncc1CO]

A solution of ethyl 2-((4-(difluoromethoxy)phenyl)amino)-4-methoxypyrimidine-5-carboxylate (0.37 g, 1.090 mmol) in THF (11 mL) was cooled to −78° C. and DIBAL-H (4.36 mL, 4.36 mmol) was added. The cold bath was removed and mixture was stirred for 1.5 h while warming to room temperature. The reaction mixture was diluted with THF (30 mL) and quenched with $Na_2SO_4 \cdot 10H_2O$, followed by a few drops of water. After stirring at room temperature for 18 h, the mixture was filtered through a pad of celite topped with silica gel. The pad was washed several times with methanol and the filtrate was concentrated. The residue was purified by flash chromatography on silica gel using 30-100% ethyl acetate in hexanes. The desired fractions were concentrated to give (2-((4-(difluoromethoxy)phenyl)amino)-4-methoxypyrimidin-5-yl)methanol as an off-white solid (0.3 g, 93%). $^1$H NMR (400 MHz, DMSO-$d_6$) δ ppm 9.57 (s, 1H), 8.16 (s, 1H), 7.89-7.67 (m, 2H), 7.38-6.83 (m, 3H), 4.98 (t, J=5.5 Hz, 1H), 4.36 (d, J=5.5 Hz, 2H), 3.95 (s, 3H). LCMS: R.T.=0.70; [M+H]$^+$=298.2.

5-(chloromethyl)-N-(4-(difluoromethoxy)phenyl)-4-methoxypyrimidin-2-amine hydrochloride

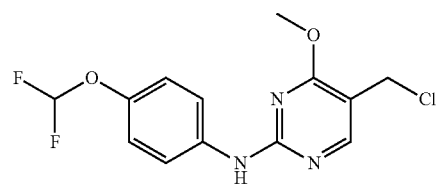 [SMILES: COc1nc(Nc2ccc(OC(F)F)cc2)ncc1CCl]

Thionyl chloride (0.295 mL, 4.04 mmol) was added to a suspension of ((2-((4-(difluoromethoxy)phenyl)amino)-4-methoxypyrimidin-5-yl)methanol (0.3 g, 1.009 mmol) in DCM (10 mL) cooled to 0° C. The mixture was stirred for 18 h while warming to room temperature. The reaction mixture was concentrated and dried under vacuum to give 5-(chloromethyl)-N-(4-(difluoromethoxy)phenyl)-4-methoxypyrimidin-2-amine hydrochloride as a beige solid (0.35 g, 97%). $^1$H NMR (400 MHz, DMSO-$d_6$) δ ppm 9.98 (s, 1H), 8.34 (s, 1H), 7.87-7.72 (m, 2H), 7.42-6.86 (m, 3H), 4.67 (s, 2H), 4.02 (s, 3H).

6-((2-((4-(difluoromethoxy)phenyl)amino)-4-methoxypyrimidin-5-yl)methoxy)quinolin-2(1H)-one

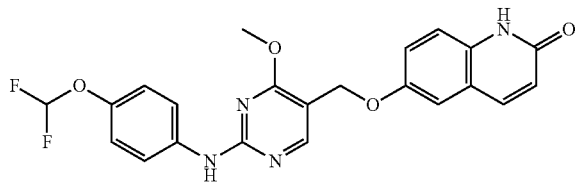 [SMILES: COc1nc(Nc2ccc(OC(F)F)cc2)ncc1COc1ccc2[nH]c(=O)ccc2c1]

A solution of 5-(chloromethyl)-N-(4-(difluoromethoxy)phenyl)-4-methoxypyrimidin-2-amine hydrochloride (0.14 g, 0.398 mmol) in DMF (1.5 mL) was added to a mixture of 6-hydroxyquinolin-2(1H)-one (0.08 g, 0.496 mmol) and $Cs_2CO_3$ (0.518 g, 1.590 mmol) in DMF (6.5 mL). The reaction mixture was stirred at room temperature for 18 h, then diluted with water and filtered. The filter cake was stirred in methanol/DCM (1:1) for 18 h, filtered, and dried to give 6-((2-((4-(difluoromethoxy)phenyl)amino)-4-methoxypyrimidin-5-yl)methoxy)quinolin-2(1H)-one as a beige solid (0.082 g, 45%). $^1$H NMR (400 MHz, DMSO-$d_6$) δ ppm 11.67 (s, 1H), 9.76 (s, 1H), 8.35 (s, 1H), 7.96-7.70 (m, 3H), 7.36-6.93 (m, 6H), 6.51 (d, J=9.5 Hz, 1H), 4.94 (s, 2H), 3.99 (s, 3H). LCMS: R.T.=0.82; [M+H]$^+$=441.1.

The following compounds were synthesized by methods similar to those described for the previous examples.

| Ex. | R$_1$ | R$_2$ | R$_3$ | LCMS RT, min | LCMS Ion [M + H]$^+$ | $^1$H NMR |
|---|---|---|---|---|---|---|
| 19 | 4-Cl-benzyl | quinolin-2(1H)-one-6-yl | H | 3.55 | 393.00 | $^1$H NMR (400 MHz, DMSO-$d_6$) δ ppm 11.67 (1H, s), 8.41 (2H, s), 7.71-7.99 (2H, m), 7.27-7.40 (5H, m), 7.13-7.28 (2H, m), 6.51 (1H, dd, J = 9.54, 1.76 Hz), 4.92 (2H, s), 4.50 (2H, d, J = 6.27 Hz) |
| 20 | 3,4-diCl-benzyl | quinolin-2(1H)-one-6-yl | H | 4.01 | 412.98 | $^1$H NMR (400 MHz, DMSO-$d_6$) δ ppm 11.69 (1H, s), 10.15 (1H, s), 8.69 (2H, s), 8.20 (1H, d, J = 2.51 Hz), 7.88 (1H, d, J = 9.54 Hz), 7.73 (1H, dd, J = 9.03, 2.51 Hz), 7.55 (1H, d, J = 8.78 Hz), 7.37 (1H, d, J = 2.01 Hz), 7.15-7.33 (2H, m), 6.52 (1H, dd, J = 9.54, 1.76 Hz), 5.06 (2H, s) |

-continued

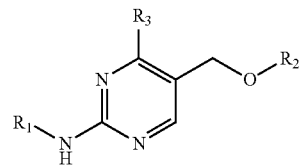

| Ex. | R₁ | R₂ | R₃ | LCMS RT, min | LCMS Ion [M + H]⁺ | ¹H NMR |
|---|---|---|---|---|---|---|
| 21 | 3,4-dichlorobenzyl | 6-(2-oxo-1,2-dihydroquinolinyl) | H | 3.75 | 427.06 | ¹H NMR (400 MHz, DMSO-d₆) δ ppm 11.67 (1H, s), 8.42 (2H, s), 7.97 (1H, t, J = 6.27 Hz), 7.86 (1H, d, J = 9.54 Hz), 7.48-7.64 (2H, m), 7.16-7.37 (4H, m), 6.51 (1H, dd, J = 9.41, 1.88 Hz), 4.92 (2H, s), 4.50 (2H, d, J = 6.27 Hz) |
| 22 | 4-(difluoromethoxy)benzyl | 6-(2-oxo-1,2-dihydroquinolinyl) | H | 3.50 | 411.2 | ¹H NMR (400 MHz, DMSO-d₆) δ ppm 11.68 (s, 1H), 9.86 (s, 1H), 8.62 (s, 2H), 7.97-7.65 (m, 3H), 7.44-6.84 (m, 6H), 6.52 (d, J = 9.5 Hz, 1H), 5.04 (s, 2H |
| 23 | 4-(trifluoromethoxy)benzyl | 6-(2-oxo-1,2-dihydroquinolinyl) | H | 3.82 | not detected | ¹H NMR (500 MHz, DMSO-d₆) δ ppm 11.66 (s, 1H), 10.21 (s, 1H), 8.69 (s, 2H), 8.00 (d, J = 8.5 Hz, 2H), 7.86 (d, J = 9.6 Hz, 1H), 7.65 (d, J = 8.7 Hz, 2H), 7.37 (d, J = 2.3 Hz, 1H), 7.30-7.16 (m, 2H), 6.51 (d, J = 9.6 Hz, 1H), 5.06 (s, 2H). |

-continued
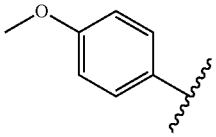 [SMILES: *c1ccc(OC)cc1]
| Ex. | R₁ | R₂ | R₃ | LCMS RT, min | LCMS Ion [M + H]⁺ | ¹H NMR |
|---|---|---|---|---|---|---|
| 24 | 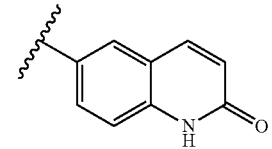 [SMILES: *c1ccc2[nH]c(=O)ccc2c1] | 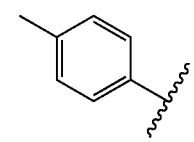 [SMILES: *c1ccc(C)cc1] | H | 3.20 | 375.2 | ¹H NMR (400 MHz, DMSO-d₆) δ ppm 11.68 (s, 1H), 9.57 (s, 1H), 8.55 (s, 2H), 7.87 (d, J = 9.5 Hz, 1H), 7.68-7.56 (m, 2H), 7.37 (d, J = 2.5 Hz, 1H), 7.30-7.17 (m, 2H), 6.98-6.72 (m, 2H), 6.52 (dd, J = 9.4, 1.6 Hz, 1H), 5.00 (s, 2H), 3.73 (s, 3H). |
| 25 | 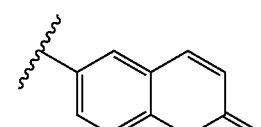 | 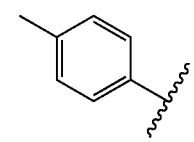 [SMILES: *c1ccc(C)cc1] | H | 3.53 | 359.2 | ¹H NMR (400 MHz, DMSO-d₆) δ ppm 11.68 (br. s., 1H), 9.67 (s, 1H), 8.59 (s, 2H), 7.88 (d, J = 9.5 Hz, 1H), 7.64 (d, J = 8.3 Hz, 2H), 7.37 (d, J = 2.3 Hz, 1H), 7.31-7.19 (m, 2H), 7.11 (d, J = 8.3 Hz, 2H), 6.52 (d, J = 9.5 Hz, 1H), 5.02 (s, 2H), 2.26 (s, 3H). |

-continued
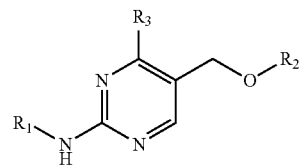
| Ex. | R₁ | R₂ | R₃ | LCMS RT, min | LCMS Ion [M + H]⁺ | ¹H NMR |
|---|---|---|---|---|---|---|
| 26 | 3,4-difluorobenzyl | (2-oxo-1,2-dihydroquinolin-6-yl)methyl | H | 3.24 | 395.2 | ¹H NMR (400 MHz, DMSO-d₆) δ ppm 11.67 (s, 1H), 8.42 (s, 2H), 7.94 (t, J = 6.4 Hz, 1H), 7.86 (d, J = 9.5 Hz, 1H), 7.43-7.30 (m, 3H), 7.28-7.10 (m, 3H), 6.51 (dd, J = 9.4, 1.9 Hz, 1H), 4.93 (s, 2H), 4.50 (d, J = 6.3 Hz, 2H) |
| 27 | 4-fluorobenzyl | (2-oxo-1,2-dihydroquinolin-6-yl)methyl | H | 3.32 | 377.2 | ¹H NMR (400 MHz, DMSO-d₆) δ ppm 11.67 (s, 1H), 8.41 (s, 2H), 7.95-7.74 (m, 2H), 7.40-7.30 (m, 3H), 7.28-7.06 (m, 4H), 6.51 (dd, J = 9.5, 2.0 Hz, 1H), 4.92 (s, 2H), 4.50 (d, J = 6.3 Hz, 2H). |

-continued
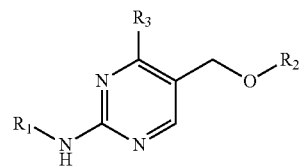
| Ex. | R₁ | R₂ | R₃ | LCMS RT, min | LCMS Ion [M + H]⁺ | ¹H NMR |
|---|---|---|---|---|---|---|
| 28 | 3-F, 4-methylphenyl | quinolin-2(1H)-on-6-yl | H | 3.75 | 377.2 | ¹H NMR (400 MHz, DMSO-d₆) δ ppm 11.69 (s, 1H), 9.92 (s, 1H), 8.64 (s, 2H), 7.88 (d, J = 9.5 Hz, 1H), 7.76 (dd, J = 12.8, 2.0 Hz, 1H), 7.47-7.34 (m, 2H), 7.30-7.11 (m, 3H), 6.52 (dd, J = 9.5, 2.0 Hz, 1H), 5.04 (s, 2H), 2.18 (s, 3H). |
| 29 | 3-F, 4-methoxyphenyl | quinolin-2(1H)-on-6-yl | H | 0.88 | 393.1 | ¹H NMR (400 MHz, DMSO-d₆) δ ppm 11.68 (s, 1H), 9.79 (s, 1H), 8.61 (s, 2H), 7.87 (d, J = 9.5 Hz, 1H), 7.78 (dd, J = 14.3, 2.5 Hz, 1H), 7.48-7.34 (m, 2H), 7.30-7.19 (m, 2H), 7.12 (t, J = 9.4 Hz, 1H), 6.52 (dd, J = 9.5, 2.0 Hz, 1H), 5.02 (s, 2H), 3.81 (s, 3H). |

-continued
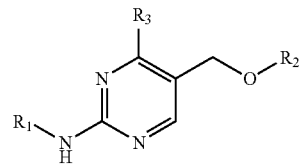
| Ex. | R₁ | R₂ | R₃ | LCMS RT, min | LCMS Ion [M + H]⁺ | ¹H NMR |
|---|---|---|---|---|---|---|
| 30 | 4-F-phenyl | 6-(2-oxo-1,2-dihydroquinolin-6-yl) | H | 0.83 | 363.1 | ¹H NMR (400 MHz, DMSO-d₆) δ ppm 11.68 (s, 1H), 9.82 (s, 1H), 8.61 (s, 2H), 7.87 (d, J = 9.5 Hz, 1H), 7.81-7.69 (m, 2H), 7.37 (d, J = 2.3 Hz, 1H), 7.30-7.20 (m, 2H), 7.19-7.08 (m, 2H), 6.52 (dd, J = 9.5, 1.8 Hz, 1H), 5.03 (s, 2H). |
| 31 | 3,4-diF-phenyl | 6-(2-oxo-1,2-dihydroquinolin-6-yl) | H | 0.88 | 381.1 | ¹H NMR (400 MHz, DMSO-d₆) δ ppm 11.69 (s, 1H), 10.03 (s, 1H), 8.66 (s, 2H), 8.00 (ddd, J = 14.0, 7.5, 2.6 Hz, 1H), 7.88 (d, J = 9.5 Hz, 1H), 7.53-7.43 (m, 1H), 7.42-7.30 (m, 2H), 7.30-7.18 (m, 2H), 6.52 (dd, J = 9.5, 2.0 Hz, 1H), 5.05 (s, 2H). |

-continued
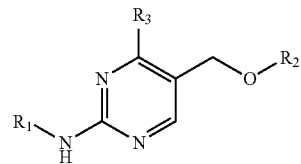
| Ex. | R₁ | R₂ | R₃ | LCMS RT, min | LCMS Ion [M + H]⁺ | ¹H NMR |
|---|---|---|---|---|---|---|
| 32 | 3-Cl, 4-F phenyl | quinolin-2(1H)-on-6-yl | H | 0.90 | 397.1 | ¹H NMR (400 MHz, DMSO-d₆) δ ppm 11.69 (s, 1H), 10.02 (s, 1H), 8.66 (s, 2H), 8.11 (dd, J = 6.9, 2.6 Hz, 1H), 7.88 (d, J = 9.8 Hz, 1H), 7.75-7.62 (m, 1H), 7.42-7.31 (m, 2H), 7.30-7.15 (m, 2H), 6.52 (dd, J = 9.7, 1.6 Hz, 1H), 5.05 (s, 2H |
| 33 | 3-OMe, 4-F phenyl | quinolin-2(1H)-on-6-yl | H | 0.83 | 393.1 | ¹H NMR (400 MHz, DMSO-d₆) δ ppm 11.69 (s, 1H), 9.77 (s, 1H), 8.62 (s, 2H), 7.87 (d, J = 9.5 Hz, 1H), 7.64 (dd, J = 8.0, 2.5 Hz, 1H), 7.39-7.31 (m, 2H), 7.30-7.19 (m, 2H), 7.13 (dd, J = 11.4, 8.9 Hz, 1H), 6.66-6.34 (m, 1H), 5.03 (s, 2H), 3.35 (s, 3H). |

-continued
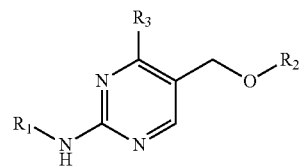
| Ex. | R₁ | R₂ | R₃ | LCMS RT, min | LCMS Ion [M + H]⁺ | ¹H NMR |
|---|---|---|---|---|---|---|
| 34 | (4-chloro-3-fluorophenyl) | (2-oxo-1,2-dihydroquinolin-6-yl)methyl | H | 0.83 | [M + ACN]⁺ 438.1 | ¹H NMR (500 MHz, DMSO-d₆) δ ppm 11.65 (s, 1H), 10.14 (s, 1H), 8.67 (s, 2H), 8.02 (dd, J = 12.6, 2.4 Hz, 1H), 7.86 (d, J = 9.6 Hz, 1H), 7.59-7.41 (m, 2H), 7.36 (d, J = 2.4 Hz, 1H), 7.30-7.20 (m, 2H), 6.51 (d, J = 9.6 Hz, 1H), 5.06 (s, 2H). |
| 35 | (3-chloro-4-(difluoromethoxy)phenyl) | (2-oxo-1,2-dihydroquinolin-6-yl)methyl | H | 0.92 | 445.1 | ¹H NMR (500 MHz, DMSO-d₆) δ ppm 11.65 (s, 1H), 10.02 (s, 1H), 8.66 (s, 2H), 8.11 (d, J = 2.6 Hz, 1H), 7.86 (d, J = 9.6 Hz, 1H), 7.70 (dd, J = 9.0, 2.6 Hz, 1H), 7.41-6.95 (m, 5H), 6.51 (d, J = 9.5 Hz, 1H), 5.05 (s, 2H). |

-continued
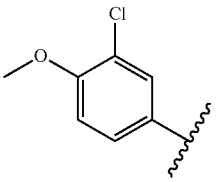 [SMILES: *c1ccc(OC)c(F)c1]
| Ex. | R₁ | R₂ | R₃ | LCMS RT, min | LCMS Ion [M + H]⁺ | ¹H NMR |
|---|---|---|---|---|---|---|
| 36 | 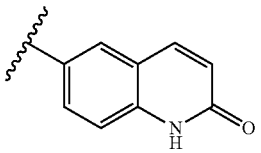 [SMILES: *c1ccc2[nH]c(=O)ccc2c1] | 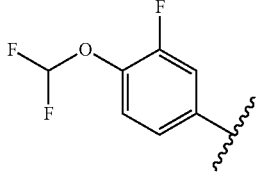 | H | 0.89 | 409.1 | ¹H NMR (400 MHz, DMSO-d₆) δ ppm 11.68 (s, 1H), 9.76 (s, 1H), 8.61 (s, 2H), 7.93 (d, J = 2.8 Hz, 1H), 7.88 (d, J = 9.5 Hz, 1H), 7.62 (dd, J = 8.9, 2.6 Hz, 1H), 7.37 (d, J = 2.3 Hz, 1H), 7.32-7.20 (m, 2H), 7.12 (d, J = 9.0 Hz, 1H), 6.52 (dd, J = 9.4, 1.9 Hz, 1H), 5.02 (s, 2H), 3.83 (s, 3H). |
| 37 | 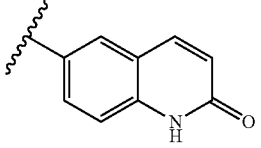 [SMILES: *c1ccc2[nH]c(=O)ccc2c1] | 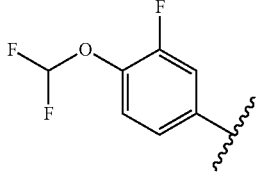 | H | 0.90 | 429.0 | ¹H NMR (400 MHz, DMSO-d₆) δ ppm 11.69 (s, 1H), 10.10 (s, 1H), 8.68 (s, 2H), 7.98 (dd, J = 13.8, 2.5 Hz, 1H), 7.88 (d, J = 9.5 Hz, 1H), 7.55-7.47 (m, 1H), 7.38 (d, J = 2.0 Hz, 1H), 7.35-6.91 (m, 4H), 6.52 (dd, J = 9.5, 2.0 Hz, 1H), 5.06 (s, 2H) |

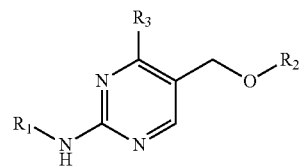
| Ex. | R$_1$ | R$_2$ | R$_3$ | LCMS RT, min | LCMS Ion [M + H]$^+$ | $^1$H NMR |
|---|---|---|---|---|---|---|
| 38 | difluoromethoxy-methylphenyl | quinolin-2(1H)-one-6-yl | H | 0.89 | 425.1 | $^1$H NMR (400 MHz, DMSO-d$_6$) δ ppm 11.68 (s, 1H), 9.78 (s, 1H), 8.61 (s, 2H), 7.88 (d, J = 9.5 Hz, 1H), 7.72-7.59 (m, 2H), 7.42-6.81 (m, 5H), 6.64-6.34 (m, 1H), 5.03 (s, 2H), 2.23 (s, 3H). |
| 39 | ethyl-fluorophenyl | quinolin-2(1H)-one-6-yl | H | 0.95 | 391.1 | $^1$H NMR (400 MHz, DMSO-d$_6$) δ ppm 11.68 (s, 1H), 9.92 (s, 1H), 8.64 (s, 2H), 7.88 (d, J = 9.5 Hz, 1H), 7.75 (dd, J = 13.3, 2.3 Hz, 1H), 7.45-7.33 (m, 2H), 7.29-7.16 (m, 3H), 6.52 (dd, J = 9.7, 1.9 Hz, 1H), 5.04 (s, 2H), 2.57 (q, J = 7.8 Hz, 2H), 1.16 (t, J = 7.5 Hz, 3H). |

-continued

| Ex. | R₁ | R₂ | R₃ | LCMS RT, min | LCMS Ion [M + H]⁺ | ¹H NMR |
|---|---|---|---|---|---|---|
| 40 | (4-methylsulfonylphenyl) | (quinolin-2(1H)-on-6-yl) | H | 0.74 | 423.0 | ¹H NMR (400 MHz, DMSO-d₆) δ ppm 11.69 (s, 1H), 10.36 (s, 1H), 8.72 (s, 2H), 8.03 (d, J = 8.8 Hz, 2H), 7.95-7.71 (m, 3H), 7.38 (d, J = 1.8 Hz, 1H), 7.34-7.18 (m, 2H), 6.52 (d, J = 9.3 Hz, 1H), 5.08 (s, 2H), 3.16 (s, 3H) |
| 41 | (3,4-dimethylphenyl) | (quinolin-2(1H)-on-6-yl) | H | 0.90 | 373.1 | ¹H NMR (400 MHz, DMSO-d₆) δ ppm 11.68 (s, 1H), 9.58 (s, 1H), 8.58 (s, 2H), 7.87 (d, J = 9.5 Hz, 1H), 7.55-7.44 (m, 2H), 7.37 (s, 1H), 7.34-7.18 (m, 2H), 7.04 (d, J = 8.8 Hz, 1H), 6.51 (d, J = 9.5 Hz, 1H), 5.01 (s, 2H), 2.20 (s, 3H), 2.17 (s, 3H). |

-continued
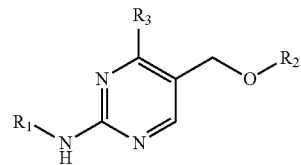
| Ex. | R₁ | R₂ | R₃ | LCMS RT, min | LCMS Ion [M + H]⁺ | ¹H NMR |
|---|---|---|---|---|---|---|
| 42 | 3-chloro-4-methylphenyl | 2-oxo-1,2-dihydroquinolin-6-yl | H | 0.95 | 393.0 | ¹H NMR (400 MHz, DMSO-d₆) δ ppm 11.68 (s, 1H), 9.90 (s, 1H), 8.65 (s, 2H), 7.98 (d, J = 2.3 Hz, 1H), 7.87 (d, J = 9.8 Hz, 1H), 7.58 (dd, J = 8.4, 2.1 Hz, 1H), 7.37 (d, J = 2.3 Hz, 1H), 7.30-7.16 (m, 3H), 6.52 (d, J = 9.5 Hz, 1H), 5.04 (s, 2H), 2.28 (s, 3H). |
| 43 | 4-propylphenyl | 2-oxo-1,2-dihydroquinolin-6-yl | H | 0.87 | 387.1 | ¹H NMR (400 MHz, DMSO-d₆) δ ppm 11.68 (s, 1H), 9.67 (s, 1H), 8.58 (s, 2H), 7.87 (d, J = 9.5 Hz, 1H), 7.65 (d, J = 8.5 Hz, 2H), 7.37 (d, J = 2.3 Hz, 1H), 7.29-7.20 (m, 2H), 7.11 (d, J = 8.5 Hz, 2H), 6.51 (dd, J = 9.7, 1.4 Hz, 1H), 5.02 (s, 2H), 1.58 (t, J = 7.4 Hz, 2H), 0.90 (t, J = 7.3 Hz, 3H). |

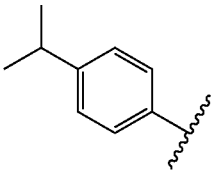 [SMILES: *c1ccc(C(C)C)cc1]
| Ex. | R₁ | R₂ | R₃ | LCMS RT, min | LCMS Ion [M + H]⁺ | ¹H NMR |
|---|---|---|---|---|---|---|
| 44 | 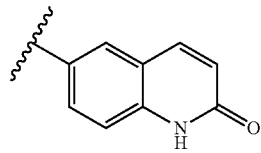 [SMILES: *c1ccc2[nH]c(=O)ccc2c1] | 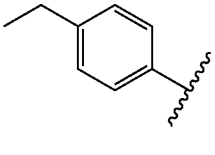 [SMILES: *c1ccc(CC)cc1] | H | 0.96 | 387.1 | ¹H NMR (400 MHz, DMSO-d₆) δ ppm 11.68 (s, 1H), 9.66 (s, 1H), 8.58 (s, 2H), 7.87 (d, J = 9.5 Hz, 1H), 7.64 (d, J = 8.5 Hz, 2H), 7.37 (d, J = 2.3 Hz, 1H), 7.30-7.21 (m, 2H), 7.17 (d, J = 8.5 Hz, 2H), 6.52 (d, J = 9.5 Hz, 1H), 5.02 (s, 2H), 2.84 (spt, J = 7.1 Hz, 1H), 1.20 (d, J = 6.8 Hz, 6H) |
| 45 | 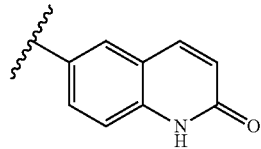 [SMILES: *c1ccc2[nH]c(=O)ccc2c1] | 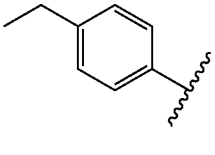 [SMILES: *c1ccc(CC)cc1] | H | 0.92 | 383.1 | ¹H NMR (400 MHz, DMSO-d₆) δ ppm 11.68 (s, 1H), 9.67 (s, 1H), 8.59 (s, 2H), 7.88 (d, J = 9.5 Hz, 1H), 7.65 (d, J = 8.5 Hz, 2H), 7.37 (d, J = 2.3 Hz, 1H), 7.30-7.21 (m, 2H), 7.13 (d, J = 8.5 Hz, 2H), 6.52 (dd, J = 9.5, 1.8 Hz, 1H), 5.02 (s, 2H), 2.60-2.54 (m, 2H), 1.18 (t, J = 7.5 Hz, 3H). |

-continued
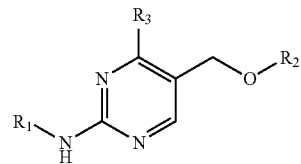
| Ex. | R₁ | R₂ | R₃ | LCMS RT, min | LCMS Ion [M + H]⁺ | ¹H NMR |
|---|---|---|---|---|---|---|
| 46 | 3-methyl-4-methoxyphenyl | 2-oxo-1,2-dihydroquinolin-6-yl | H | 0.88 | 389.1 | ¹H NMR (400 MHz, DMSO-d₆) δ ppm 11.76-11.60 (m, 1H), 9.66 (s, 1H), 8.60 (s, 2H), 7.94-7.79 (m, 1H), 7.45-7.41 (m, 1H), 7.40-7.34 (m, 1H), 7.26 (s, 2H), 7.11-6.98 (m, 1H), 6.60-6.44 (m, 1H), 5.02 (s, 2H), 3.77 (s, 3H), 2.10 (s, 3H). |
| 47 | 4-tert-butylphenyl | 2-oxo-1,2-dihydroquinolin-6-yl | H | 0.99 | 401.1 | ¹H NMR (400 MHz, DMSO-d₆) δ ppm 11.68 (s, 1H), 9.67 (s, 1H), 8.58 (s, 2H), 7.87 (d, J = 9.8 Hz, 1H), 7.65 (d, J = 8.8 Hz, 2H), 7.42-7.15 (m, 5H), 6.52 (d, J = 9.5 Hz, 1H), 5.02 (s, 2H), 1.28 (s, 9H). |

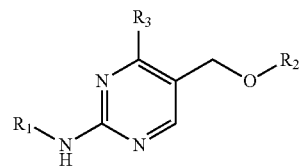
| Ex. | R₁ | R₂ | R₃ | LCMS RT, min | LCMS Ion [M + H]⁺ | ¹H NMR |
|---|---|---|---|---|---|---|
| 48 | 6-methoxypyridin-3-yl | 2-oxo-1,2-dihydroquinolin-6-yl | H | 0.69 | 376.1 | ¹H NMR (400 MHz, DMSO-d₆) δ ppm 11.68 (s, 1H), 9.68 (s, 1H), 8.58 (s, 2H), 8.47 (d, J = 2.5 Hz, 1H), 8.02 (dd, J = 9.0, 2.8 Hz, 1H), 7.87 (d, J = 9.5 Hz, 1H), 7.36 (d, J = 2.0 Hz, 1H), 7.32-7.18 (m, 2H), 6.81 (d, J = 8.8 Hz, 1H), 6.52 (d, J = 9.0 Hz, 1H), 5.02 (s, 2H), 3.83 (s, 3H) |
| 49 | 6-methoxy-5-methylpyridin-3-yl | 2-oxo-1,2-dihydroquinolin-6-yl | H | 0.80 | 390.1 | ¹H NMR (400 MHz, DMSO-d₆) δ ppm 11.68 (s, 1H), 9.60 (s, 1H), 8.57 (s, 2H), 8.30 (d, J = 2.3 Hz, 1H), 7.91-7.78 (m, 2H), 7.36 (d, J = 2.3 Hz, 1H), 7.32-7.18 (m, 2H), 6.51 (d, J = 9.8 Hz, 1H), 5.01 (s, 2H), 3.86 (s, 3H), 2.15 (s, 3H). |

-continued

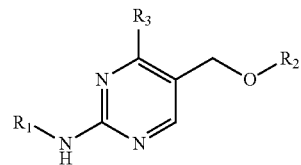

| Ex. | R₁ | R₂ | R₃ | LCMS RT, min | LCMS Ion [M + H]⁺ | ¹H NMR |
|---|---|---|---|---|---|---|
| 50 | 6-(difluoromethoxy)pyridin-3-yl | 2-oxo-1,2-dihydroquinolin-6-yl | H | 0.88 | 412.0 | ¹H NMR (400 MHz, DMSO-d₆) δ ppm 11.69 (s, 1H), 9.97 (s, 1H), 8.73-8.55 (m, 3H), 8.26 (dd, J = 8.9, 2.6 Hz, 1H), 7.94-7.43 (m, 2H), 7.37 (d, J = 2.0 Hz, 1H), 7.30-7.19 (m, 2H), 7.09 (d, J = 9.0 Hz, 1H), 6.52 (d, J = 9.5 Hz, 1H), 5.05 (s, 2H). |
| 51 | 4-chlorophenyl | 2-oxo-1,2-dihydroquinolin-6-yl | CH₃ | 3.87 | 393.2 | ¹H NMR (400 MHz, DMSO-d₆) δ ppm 11.68 (s, 1H), 9.87 (s, 1H), 8.48 (s, 1H), 7.90-7.79 (m, 3H), 7.39 (s, 1H), 7.34 (d, J = 9.0 Hz, 2H), 7.26 (s, 2H), 6.52 (dd, J = 9.7, 1.6 Hz, 1H), 5.07 (s, 2H), 2.47 (s, 3H) |
| 52 | 4-(difluoromethoxy)phenyl | 2-oxo-1,2-dihydroquinolin-6-yl | CH₃ | 0.87 | 425.0 | ¹H NMR (400 MHz, DMSO-d₆) δ ppm 11.68 (s, 1H), 9.78 (s, 1H), 8.46 (s, 1H), 7.94-7.70 (m, 3H), 7.44-6.82 (m, 6H), 6.52 (d, J = 9.8 Hz, 1H), 5.06 (s, 2H), 2.46 (s, 3H) |

-continued
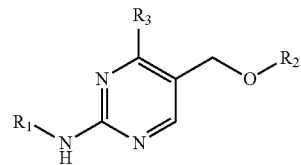
| Ex. | R₁ | R₂ | R₃ | LCMS RT, min | LCMS Ion [M + H]⁺ | ¹H NMR |
|---|---|---|---|---|---|---|
| 53 | ![F,F,O-phenyl with OCHF₂ para] | ![6-quinolin-2(1H)-one] | CF₃ | 0.96 | 478.97 | ¹H NMR (400 MHz, DMSO-d₆) δ ppm 11.70 (s, 1H), 10.41 (s, 1H), 8.94 (s, 1H), 7.88 (d, J = 9.8 Hz, 1H), 7.83-7.76 (m, 2H), 7.39 (d, J = 2.5 Hz, 1H), 7.37-6.95 (m, 5H), 6.62-6.37 (m, 1H), 5.14 (s, 2H) |
| 54 | ![4-Cl-phenyl] | ![6-quinolin-2(1H)-one] | CF₃ | 1.01 | 446.86 | ¹H NMR (400 MHz, DMSO-d₆) δ ppm 11.70 (s, 1H), 10.48 (s, 1H), 8.96 (s, 1H), 7.88 (d, J = 9.5 Hz, 1H), 7.81 (d, J = 9.0 Hz, 2H), 7.46-7.35 (m, 3H), 7.34-7.14 (m, 2H), 6.53 (d, J = 9.5 Hz, 1H), 5.15 (s, 2H) |
| 55 | ![4-OCHF₂-phenyl] | ![6-quinolin-2(1H)-one] | N(CH₃)₂ | 3.10 | 454.1 | ¹H NMR (400 MHz, DMSO-d₆) δ ppm 11.71 (br. s., 1H), 10.34 (br. s., 1H), 8.13 (s, 1H), 7.86 (d, J = 9.5 Hz, 1H), 7.65 (d, J = 9.0 Hz, 2H), 7.48-6.96 (m, 6H), 6.53 (d, J = 9.5 Hz, 1H), 5.07 (s, 2H), 3.55-3.19 (m, 6H) |

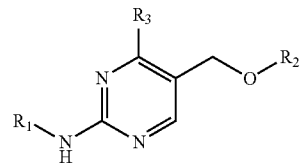
| Ex. | R₁ | R₂ | R₃ | LCMS RT, min | LCMS Ion [M + H]⁺ | ¹H NMR |
|---|---|---|---|---|---|---|
| 56 | 4-(OCF₃)phenyl | 1H-indazol-5-yl | H | 1.94 | 402.2 | 1H NMR (400 MHz, DMSO-d6) δ ppm 5.04 (s, 2H) 7.04-7.11 (m, 1H) 7.27-7.35 (m, 3H) 7.48 (s, 1 H) 7.89 (s, 2H) 7.98 (s, 1H) 8.64 (s, 2 H) 9.98 (s, 1H) |
| 57 | 4-(OCHF₂)phenyl | 1H-indazol-5-yl | H | 1.80 | 383.8 | 400 MHz, DMSO-d6: δ ppm 5.03 (s, 2H) 6.93-7.36 (m, 5H) 7.48 (s, 1 H) 7.75-7.82 (m, 2 H) 7.98 (s, 1H) 8.61 (s, 2H) 9.83 (s, 1 H) 12.95 (br. s., 1 H) |
| 58 | 4-(OCHF₂)phenyl | 2-oxo-2,4-dihydro-1H-benzo[d][1,3]oxazin-6-yl | H | 1.95 | 415 | 1H NMR (400 MHz, DMSO-d6) δ ppm 4.96 (s, 2H) 5.24 (s, 2 H) 6.78-7.31 (m, 6 H) 7.75-7.81 (m, 2 H) 8.57 (s, 2H) 9.82 (s, 1H) 10.00 (s, 1 H) |
| 59 | 4-(OCHF₂)phenyl | 6-hydroxypyridazin-3-yl | H | 1.65 | 362 | 1H NMR (400 MHz, DMSO-d6) δ ppm 5.06 (s, 2H) 6.89-7.34 (m, 5H) 7.79 (s, 2 H) 8.60 (s, 2H) 9.86 (s, 1H) |

-continued

| Ex. | R₁ | R₂ | R₃ | LCMS RT, min | LCMS Ion [M + H]⁺ | ¹H NMR |
|---|---|---|---|---|---|---|
| 60 | 4-(difluoromethoxy)phenyl | 1H-benzimidazol-5-yl | H | 1.82 | 384.2 | 1H NMR (400 MHz, DMSO-d6) δ ppm 5.12 (s, 2H) 7.13 (s, 5 H) 7.38-7.43 (m, 1 H) 7.71-7.83 (m, 3 H) 8.63 (s, 2H) 9.16-9.24 (m, 1 H) 9.81-9.88 (m, 1 H) |
| 61 | 4-(trifluoromethoxy)phenyl | 2-oxo-1,4-dihydro-2H-benzo[d][1,3]oxazin-6-yl | H | 1.915 | 433.0 | 1H NMR (400 MHz, DMSO-d6) δ ppm 4.97 (s, 1H) 5.24 (s, 1 H) 6.22-6.63 (m, 1 H) 6.79-6.86 (m, 1 H) 6.94-6.98 (m, 1 H) 7.28-7.34 (m, 1 H) 7.87 (d, J = 9.03 Hz, 1H) 8.60 (s, 1H) 9.94-10.02 (m, 1H) |
| 62 | 4-(difluoromethoxy)phenyl | 2-oxo-2,3-dihydrobenzo[d]thiazol-6-yl | H | 1.99 | 415.0 | 1H NMR (400 MHz, DMSO-d6) δ ppm 4.98 (s, 2H) 6.92-7.30 (m, 6H) 7.35 (br. s., 1H) 7.78 (d, J = 9.03 Hz, 2H) 8.57 (s, 2 H) 9.81 (s, 1H) |
| 63 | 4-(difluoromethoxy)phenyl | 1H-pyrazol-4-yl | H | 1.93 | 334.2 | 1H NMR (400 MHz, DMSO-d6) δ ppm 4.84 (s, 2H) 7.12 (s, 3 H) 7.40-7.45 (m, 2 H) 7.74-7.81 (m, 2 H) 8.55 (s, 2H) 9.78-9.83 (m, 1 H) |

-continued
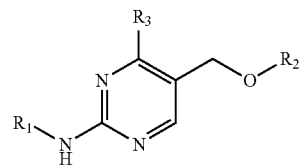
| Ex. | R₁ | R₂ | R₃ | LCMS RT, min | LCMS Ion [M + H]⁺ | ¹H NMR |
|---|---|---|---|---|---|---|
| 64 | 4-(trifluoromethoxy)phenyl | 4-chloro-1H-indazol-5-yl | H | 1.95 | 436.0 | 400 MHz, DMSO-d6: δ ppm 5.14 (s, 2H), 7.30 (d, J = 8.40 Hz, 2H), 7.45 (d, J = 9.20 Hz, 1H), 7.54 (dd, J = 0.80, 8.80 Hz, 1H), 7.84-7.85 (m, 2H), 8.04 (d, J = 0.40 Hz, 1H), 8.60 (s, 2H), 9.96 (s, 1H), 13.31 (s, 1H), . |
| 65 | 4-(difluoromethoxy)phenyl | 2-amino-benzothiazol-6-yl | H | 1.37 | 416.0 | 1H NMR (400 MHz, DMSO-d6) δ ppm 4.42 (d, J = 5.52 Hz, 2H) 6.69 (dd, J = 8.53, 2.51 Hz, 1 H) 6.90-7.30 (m, 5 H) 7.71-7.81 (m, 2 H) 8.05-8.13 (m, 1 H) 8.52 (s, 2H) 9.15 (s, 1H) 9.71 (s, 1 H) |
| 66 | 4-(difluoromethoxy)phenyl | 4-chloro-1H-indazol-5-yl | H | 1.93 | 418.2 | 1H NMR (400 MHz, DMSO-d6) δ ppm 5.13 (s, 2H) 7.10-7.15 (m, 2H) 7.46 (s, 1 H) 7.55 (d, J = 1.00 Hz, 1H) 7.74-7.80 (m, 2 H) 8.04 (s, 1H) 8.57 (s, 2H) 9.82 (s, 1 H) |

-continued
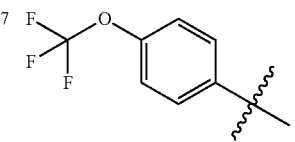
| Ex. | R₁ | R₂ | R₃ | LCMS RT, min | LCMS Ion [M + H]⁺ | ¹H NMR |
|---|---|---|---|---|---|---|
| 67 | 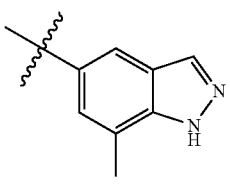 [SMILES: *c1cc(C)c2[nH]ncc2c1] | 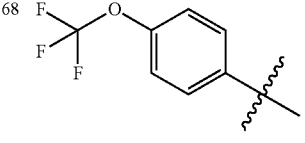 | H | 2.39 | 416.0 | 400 MHz, DMSO-d6: δ 2.50 (s, 3H), 5.02 (s, 2H), 6.88 (s, 1H), 7.14 (d, J = 2.00 Hz, 1H), 7.30 (d, J = 8.40 Hz, 3H), 7.86-7.88 (m, 2H), 7.95 (s, 1H), 8.63 (s, 2H), 9.95 (s, 1H), 13.02 (s, 1H). |
| 68 | 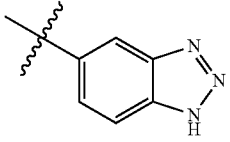 [SMILES: *c1ccc2[nH]nnc2c1] | 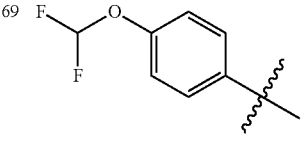 | H | 2.25 | 403.0 | 400 MHz, DMSO-d6: δ 5.13 (s, 2H), 7.05 (s, 1H), 7.31 (d, J = 8.40 Hz, 3H), 7.87-7.89 (m, 3H), 8.67 (s, 2H), 9.99 (s, 1H), 15.48 (s, 1H). |
| 69 | 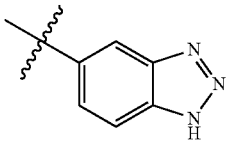 [SMILES: *c1ccc2[nH]nnc2c1] | 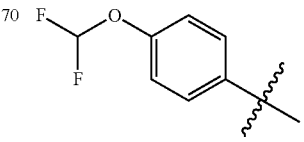 | H | 1.67 | 385.0 | 1H NMR (400 MHz, DMSO-d6) δ ppm 5.11 (s, 2H) 7.12 (s, 4 H) 7.79 (d, J = 9.29 Hz, 2H) 7.84-7.95 (m, 1 H) 8.64 (s, 2H) 9.78-9.88 (m, 1 H) |
| 70 | 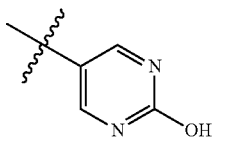 [SMILES: *c1cnc(O)nc1] |  | H | 1.7 | 362.2 | 1H NMR (400 MHz, DMSO-d6) δ ppm 4.91-4.98 (m, 2H) 6.91-7.33 (m, 3 H) 7.74-7.82 (m, 2 H) 8.16-8.30 (m, 1 H) 8.57 (s, 2H) 9.82-9.92 (m, 1 H) |

-continued
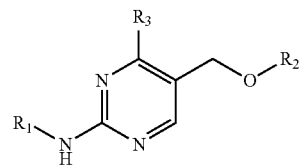
| Ex. | R₁ | R₂ | R₃ | LCMS RT, min | LCMS Ion [M + H]⁺ | ¹H NMR |
|---|---|---|---|---|---|---|
| 71 | 4-(trifluoromethoxy)phenyl | 6-benzothiazol-2(3H)-one | H | 2.4 | 435.0 | 1H NMR (400 MHz, DMSO-d6) δ ppm 5.00 (s, 2H) 6.98 (d, J = 2.76 Hz, 1H) 7.02-7.07 (m, 1H) 7.30 (d, J = 8.28 Hz, 2H) 7.37 (d, J = 2.51 Hz, 1H) 7.87 (d, J = 9.03 Hz, 2H) 8.61 (s, 2H) 9.96 (s, 1H) 11.71 (s, 1H) |
| 72 | 4-(difluoromethoxy)-3-fluorophenyl | 4-chloro-1H-indazol-5-yl | H | 2.28 | 436.0 | 1H NMR (400 MHz, DMSO-d6) ppm 5.15 (s, 2H) 6.90-7.35 (m, 3H) 7.41-7.58 (m, 4H) 7.88-8.00 (m, 1H) 8.04 (s, 1H) 8.63 (s, 2H) 10.05 (s, 1H) 13.31 (br. s., 1H) |
| 73 | 4-(difluoromethoxy)-3-methylphenyl | 4-chloro-1H-indazol-5-yl | H | 2.29 | 432.0 | 1H NMR (400 MHz, DMSO-d6) δ ppm 2.22 (s, 3H) 5.12 (s, 2H) 6.78-7.31 (m, 2H) 7.41-7.56 (m, 2H) 7.59-7.71 (m, 2H) 8.04 (d, J = 1.00 Hz, 1H) 8.57 (s, 2H) 9.74 (s, 1H) 13.32 (br. s., 1H) |

-continued

| Ex. | R₁ | R₂ | R₃ | LCMS RT, min | LCMS Ion [M + H]⁺ | ¹H NMR |
|---|---|---|---|---|---|---|
| 74 | 3-chloro-4-(difluoromethoxy)phenyl | 4-chloro-1H-indazol-5-yl | H | 2.36 | 418 | 1H NMR (400 MHz, DMSO-d6) δ ppm 5.15 (s, 2H) 6.86-7.36 (m, 2H) 7.39-7.58 (m, 2H) 7.71 (dd, J = 9.03, 2.51 Hz, 1H) 8.04 (s, 1H) 8.09 (d, J = 2.76 Hz, 1H) 8.63 (s, 2H) 10.02 (s, 1H) 13.30 (br. s., 1H) |
| 75 | 3-chloro-4-(difluoromethoxy)phenyl | 1H-indazol-5-yl | H | 2.25 | 418.0 | 1H NMR (400 MHz, DMSO-d6) δ ppm 5.05 (s, 2H) 6.91-7.37 (m, 4H) 7.47 (d, J = 9.04 Hz, 1H) 7.71 (dd, J = 9.03, 2.51 Hz, 1H) 7.98 (d, 1H) 8.06-8.15 (m, 1H) 8.60-8.74 (m, 2H) 9.96-10.06 (m, 1H) 12.96 (br. s., 1H) |
| 76 | 4-(difluoromethoxy)-3-methylphenyl | 1H-indazol-5-yl | H | 2.17 | 398.2.0 | 1H NMR (400 MHz, DMSO-d6) δ ppm 2.22 (s, 3H) 5.02 (s, 2H) 6.81-7.27 (m, 3H) 7.34 (d, J = 2.26 Hz, 1H) 7.47 (d, J = 9.04 Hz, 1H) 7.58-7.70 (m, 2H) 7.97 (d, J = 0.75 Hz, 1H) 8.60 (s, 2H) 9.73 m(s, 1H) 12.92 (s, 1H) |

-continued

| Ex. | R₁ | R₂ | R₃ | LCMS RT, min | LCMS Ion [M + H]⁺ | ¹H NMR |
|---|---|---|---|---|---|---|
| 77 | 4-(difluoromethoxy)-3-chlorophenyl | 2-oxo-1,4-dihydro-2H-benzo[d][1,3]oxazin-6-yl | H | 2.19 | 449.0 | 1H NMR (400 MHz, DMSO-d6) δ ppm 4.94 (s, 2H) 5.21 (s, 2H) 6.74-6.82 (m, 1H) 6.93-7.33 (m, 3H) 7.67 (dd, J = 8.91, 2.64 Hz, 1H) 8.07 (d, J = 2.51 Hz, 1H) 8.59 (s, 2H) 9.98 (d, J = 5.02 Hz, 2H) |
| 78 | 4-(difluoromethoxy)-3-methylphenyl | 7-fluoro-2-oxo-1,2-dihydroquinolin-6-yl | H | 2.13 | 443.0 | 1H NMR (400 MHz, DMSO-d6) δ ppm 2.22 (s, 3H) 5.08 (s, 2H) 6.49 (d, J = 9.54 Hz, 1H) 7.25 (s, 3H) 7.59-7.68 (m, 3H) 7.87 (d, J = 9.79 Hz, 1H) 8.61 (s, 2H) 9.77 (s, 1H) 11.70 (s, 1H) 11.67-11.67 (m, 1H) |
| 79 | 4-(difluoromethoxy)phenyl | 1H-pyrazolo[3,4-b]pyridin-5-yl | H | 1.95 | 385.0 | 400 MHz, DMSO-d6: δ ppm 5.09 (s, 2H), 6.93-7.12 (m, 3H), 7.78 (dd, J = 2.00, 7.00 Hz, 2H), 7.88 (d, J = 2.80 Hz, 1H), 8.06 (s, 1H), 8.34 (d, J = 2.80 Hz, 1H), 8.63 (s, 2H), 9.84 (s, 1H), 13.53 (s, 1H), |

-continued

| Ex. | R₁ | R₂ | R₃ | LCMS RT, min | LCMS Ion [M + H]⁺ | ¹H NMR |
|---|---|---|---|---|---|---|
| 80 | 4-(trifluoromethoxy)phenyl | benzoxazol-2(3H)-one-6-yl | H | 2.3 | 419.0 | 1H NMR (400 MHz, DMSO-d6) δ ppm 5.01 (s, 2H) 6.84 (d, J = 2.51 Hz, 1H) 7.01 (d, J = 8.53 Hz, 1H) 7.14 (d, J = 2.26 Hz, 1H) 7.31 (d, J = 8.28 Hz, 2H) 7.81-7.90 (m, 2H) 8.58-8.64 (m, 2H) 9.96 (s, 1H) 11.46 (s, 1H) |
| 81 | 4-(trifluoromethoxy)phenyl | 7H-pyrrolo[2,3-b]pyridin-5-yl | H | 1.94 | 400.0 | 400 MHz, MeOD: δ ppm 1.86-1.88 (m, 2H), 2.01-2.02 (m, 2H), 2.61-2.64 (m, 6H), 3.62-3.65 (m, 2H), 3.78-3.80 (m, 4H), 6.53-6.77 (m, 1H), 7.06-7.08 (m, 2H), 7.21-7.24 (m, 2H), 7.42-7.43 (m, 1H), 3768.28 (d, J = −3008576.80 Hz, 1H), 7.74 (s, 1H), 8.04 (d, J = 0.80 Hz, 1H) |

-continued

| Ex. | R₁ | R₂ | R₃ | LCMS RT, min | LCMS Ion [M + H]⁺ | ¹H NMR |
|---|---|---|---|---|---|---|
| 82 | 4-(difluoromethoxy)-3-methylphenyl | 2-oxo-1,4-dihydro-2H-benzo[d][1,3]oxazin-6-yl | H | 2.0 | 429.0 | 400 MHz, DMSO-d6: δ 2.22 (s, 3H), 4.95 (s, 2H), 5.24 (s, 2H), 6.81-6.84 (m, 1H), 7.07-7.07 (m, 4H), 7.61-7.61 (m, 2H), 8.56 (s, 2H), 9.73 (s, 1H), 10.00 (s, 1H) |
| 83 | 3-fluoro-4-methylphenyl | 2-oxo-1,4-dihydro-2H-benzo[d][1,3]oxazin-6-yl | H | 2.06 | 381.2 | 400 MHz, DMSO-d6: δ ppm 2.18 (s, 3H), 4.96 (s, 2H), 5.24 (s, 2H), 6.83 (d, J = 9.20 Hz, 1H), 6.94-6.95 (m, 2H), 7.15-7.17 (m, 1H), 7.38-7.38 (m, 1H), 7.73-7.73 (m, 1H), 8.59 (s, 2H), 9.87 (s, 1H), 10.00 (s, 1H), |
| 84 | 4-(difluoromethoxy)-3-fluorophenyl | 2-oxo-1,4-dihydro-2H-benzo[d][1,3]oxazin-6-yl | H | 2.0 | 431.0 | 400 MHz, DMSO-d6: δ ppm 4.98 (s, 2H), 5.24 (s, 2H), 6.81-6.84 (m, 5H), 7.50 (d, J = 9.20 Hz, 1H), 7.97 (d, J = 14.00 Hz, 1H), 8.62 (s, 2H), 10.00 (s, 1H), 10.05 (s, 1H), |

-continued
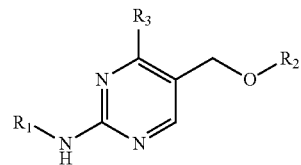
| Ex. | R₁ | R₂ | R₃ | LCMS RT, min | LCMS Ion [M + H]⁺ | ¹H NMR |
|---|---|---|---|---|---|---|
| 85 | (2-fluoro-4-(difluoromethoxy)phenyl) | (2-oxoindolin-5-yl) | H | 1.77 | 417.2 | 1H NMR (400 MHz, DMSO-d6) δ ppm 3.43-3.43 (m, 2H) 4.95-4.98 (m, 1H) 6.73 (d, J = 8.53 Hz, 1H) 6.84-6.88 (m, 1H) 7.13 (s, 1H) 7.48-7.53 (m, 1H) 7.94-7.99 (m, 1H) 8.60-8.63 (m, 1H) 10.04 (s, 1H) 10.20 (s, 1H) |
| 86 | (4-(difluoromethoxy)-3-methylphenyl) | (2-oxoindolin-5-yl) | H | 1.8 | 411.2 | 1H NMR (400 MHz, DMSO-d6) δ ppm 2.20-2.23 (m, 1H) 3.44 (s, 1H) 4.93 (s, 1H) 6.73 (s, 1H) 6.82-7.25 (m, 1H) 7.63 (s, 1H) 8.55 (s, 1H) 9.71 (s, 1H) 10.19 (s, 1H) |
| 87 | (4-(difluoromethoxy)-3-methylphenyl) | (4-(thiazol-2-ylamino)phenyl) | H | 2.22 | 456.0 | 1H NMR (400 MHz, DMSO-d6) δ ppm 2.22 (s, 2H) 4.95-4.97 (m, 1H) 6.84 (s, 1H) 6.87-7.25 (m, 4H) 7.53-7.57 (m, 1H) 7.64 (s, 1H) 8.58 (s, 1H) 9.71-9.74 (m, 1H) 10.01 (s, 1H) |

-continued
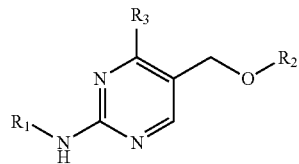
| Ex. | R₁ | R₂ | R₃ | LCMS RT, min | LCMS Ion [M + H]⁺ | ¹H NMR |
|---|---|---|---|---|---|---|
| 88 | | ![R2](7-fluoro-2-oxo-1,2-dihydroquinolin-6-yl) | H | 1.83 | 463.0 | 1H NMR (400 MHz, DMSO-d6) δ ppm 2.22 (s, 3H) 5.08 (s, 2 H) 6.49 (d, J = 9.54 Hz, 1H) 7.25 (s, 3H) 7.59-7.68 (m, 3H) 7.87 (d, J = 9.79 Hz, 1H) 8.61 (s, 2H) 9.77 (s, 1 H) 11.70 (s, 1H) 11.67-11.67 (m, 1H) |
| 89 | | ![R2](7-fluoro-2-oxo-1,2-dihydroquinolin-6-yl) | H | 1.78 | 445.0 | 1H NMR (400 MHz, DMSO-d6) δ ppm 4.34 (t, J = 5.14 Hz, 1H) 5.08-5.13 (m, 1H) 6.45-6.51 (m, 1H) 6.94-7.33 (m, 1H) 7.48-7.53 (m, 1H) 7.64 (d, J = 8.78 Hz, 1H) 7.85-7.99 (m, 1 H) 8.32 (s, 1H) 8.64-8.68 (m, 1 H) 10.08 (s, 1H) |

-continued
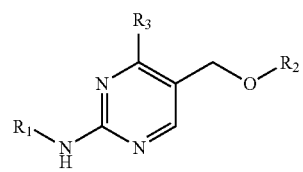
| Ex. | R₁ | R₂ | R₃ | LCMS RT, min | LCMS Ion [M + H]⁺ | ¹H NMR |
|---|---|---|---|---|---|---|
| 90 | F-CHF-O-(3-Cl-phenyl)- | 1H-pyrrolo[2,3-b]pyridin-5-yl | H | 2.47 | 418.0 | 1H NMR (400 MHz, DMSO-d6) δ ppm 5.08 (s, 2H) 6.39-6.41 (m, 1H) 6.96-7.34 (m, 2H) 7.15 (s, 1H) 7.44-7.44 (m, 1H) 7.69-7.69 (m, 2H) 8.04 (d, J = 2.76 Hz, 1H) 8.10 (d, J = 2.51 Hz, 1H) 8.66 (s, 2H) 10.02 (s, 1H) 11.53 (br. s., 1H) |
| 91 | F-CHF-O-(3-F-phenyl)- | 4-(thiazol-2-ylamino)phenyl | H | 1.97 | 460.2 | 1H NMR (400 MHz, DMSO-d6) d ppm 4.96-5.01 (m, 2H) 6.83 (d, J = 3.76 Hz, 1H) 7.00 (d, J = 9.03 Hz, 6H) 7.48-7.58 (m, 3H) 7.96 (dd, J = 13.80, 2.51 Hz, 1H) 8.61-8.65 (m, 2H) 9.99-10.06 (m, 2H) |

-continued

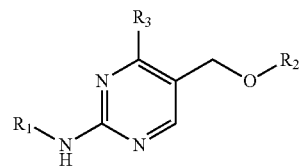

| Ex. | R₁ | R₂ | R₃ | LCMS RT, min | LCMS Ion [M + H]⁺ | ¹H NMR |
|---|---|---|---|---|---|---|
| 92 | ![R1] | ![R2] | H | 1.90 | 476.0 | 1H NMR (400 MHz, DMSO-d6) d ppm 5.00-5.22 (m, 1H) 6.82 (br. s., 1 H) 6.97-7.35 (m, 2 H) 7.70 (dd, J = 8.91, 2.64 Hz, 1 H) 8.08-8.13 (m, 1 H) 8.10 (d, J = 2.51 Hz, 1H) 8.63-8.68 (m, 1 H) 10.02-10.08 (m, 1H) |

Example 93

6-((2-(4-chlorophenylamino)pyrimidin-4-yl)methoxy)quinolin-2(1H)-one 2-ethoxyethyl 2-(4-chlorophenylamino)pyrimidine-4-carboxylate

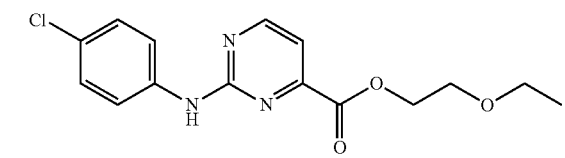 [SMILES: CCOCCOC(=O)c1ccnc(Nc2ccc(Cl)cc2)n1]

A mixture of 4-chloroaniline (0.444 g, 3.48 mmol), methyl 2-chloropyrimidine-4-carboxylate (0.3 g, 1.738 mmol) and 2 drops of concentrated HCl in 2-ethoxyethanol was heated at 100° C. for 18 h, then cooled to room temperature and concentrated.

The residue was purified by flash chromatography on silica gel using 5-60% ethyl acetate in hexanes. The desired fractions were concentrated to give 2-ethoxyethyl 2-(4-chlorophenylamino)pyrimidine-4-carboxylate as a yellow solid (0.38 g, 68%). ¹H NMR (400 MHz, CHLOROFORM-d) δ ppm 8.65 (1H, d, J=5.02 Hz), 7.59-7.67 (2H, m), 7.42 (1H, d, J=4.77 Hz), 7.37 (1H, s), 7.28-7.35 (2H, m), 4.47-4.65 (2H, m), 3.71-3.87 (2H, m), 3.61 (2H, q, J=7.03 Hz), 1.25 (3H, t, J=7.03 Hz). LCMS: R.T.=3.84; [M+H]⁺=322.0.

(2-(4-chlorophenylamino)pyrimidin-4-yl)methanol

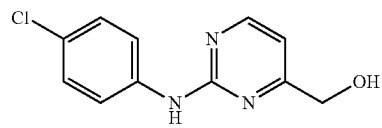 [SMILES: OCc1ccnc(Nc2ccc(Cl)cc2)n1]

A suspension of 2-ethoxyethyl 2-((4-chlorophenyl)amino) pyrimidine-4-carboxylate (0.4 g, 1.243 mmol) in THF (12 mL) was cooled to −78° C. and a 1M solution of DIBAL-H (4.97 mL, 4.97 mmol) in toluene was added. The mixture was stirred for 1.5 h at room temperature. The reaction mixture was diluted with THF (20 mL) and quenched with Na₂SO₄.10H₂O followed by a few drops of water. The mixture was stirred at room temperature for 18 h, then filtered through a pad of Celite topped with silica gel. The pad was washed with ethyl acetate and the filtrate was concentrated. The residue was purified by flash chromatography on silica gel using 75-100% ethyl acetate in hexanes. The desired fractions were concentrated to give (2-(4-chlorophenylamino)pyrimidin-4-yl)methanol as a pale yellow solid (0.224 g, 76%). ¹H NMR (400 MHz, METHANOL-d₄) δ ppm 8.41 (1H, d, J=5.02 Hz), 7.55-7.86 (2H, m), 7.19-7.40 (2H, m), 6.95 (1H, d, J=5.02 Hz), 4.57 (2H, s). LCMS: R.T.=3.10; [M+H]⁺=236.12.

6-((2-(4-chlorophenylamino)pyrimidin-4-yl)methoxy)quinolin-2(1H)-one

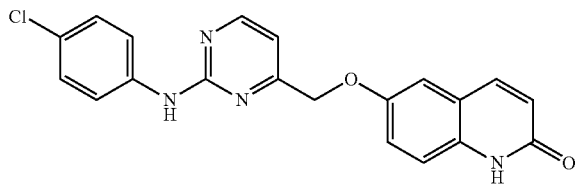 [SMILES: O=c1ccc2cc(OCc3ccnc(Nc4ccc(Cl)cc4)n3)ccc2[nH]1]

A solution of triphenylphosphine (0.145 g, 0.552 mmol) in THF (2.0 mL) was cooled to 0° C. under $N_2$ and DEAD (0.087 mL, 0.552 mmol) was added dropwise. The mixture was stirred for 10 min, then 6-hydroxyquinolin-2(1H)-one (0.068 g, 0.424 mmol) was added. After stirring for 5 min, a solution of (2-((4-chlorophenyl)amino)pyrimidin-4-yl)methanol (0.1 g, 0.424 mmol) in THF (2.0 mL) was added. The reaction was stirred for 18 h at room temperature. The mixture was diluted with water and filtered. The beige filter cake was stirred in methanol and filtered to give 6-((2-(4-chlorophenylamino)pyrimidin-4-yl)methoxy)quinolin-2(1H)-one as a beige solid (0.03 g, 18%). $^1$H NMR (400 MHz, DMSO-$d_6$) δ ppm 11.70 (s, 1H), 9.91 (s, 1H), 8.53 (d, J=4.8 Hz, 1H), 7.95-7.72 (m, 3H), 7.44-7.16 (m, 5H), 6.98 (d, J=5.0 Hz, 1H), 6.51 (d, J=9.5 Hz, 1H), 5.16 (s, 2H). LCMS: R.T.=3.74; [M+H]$^+$=379.09.

The following compound was synthesized by methods similar to that described for Example 93.

hexanes, then 10-15% methanol in ethyl acetate. The desired fractions were concentrated to give a dark brown solid which was triturated with DCM to yield N-(3,4-dichlorophenyl)-6-(methoxymethyl)pyrimidin-4-amine as a brown solid (0.66 g, 57%). $^1$H NMR (400 MHz, CHLOROFORM-d) δ ppm 8.67 (1H, d, J=1.00 Hz), 7.69 (1H, d, J=2.51 Hz), 7.44 (1H, d, J=8.53 Hz), 7.29 (1H, dd, J=8.53, 2.51 Hz), 6.95 (1H, br. s.), 6.81 (1H, d, J=1.00 Hz), 4.45 (1H, d, J=0.50 Hz), 3.50 (2H, s). LCMS: R.T.=0.77; [M+H]$^+$=283.98.

(6-(3,4-dichlorophenylamino)pyrimidin-4-yl)methanol

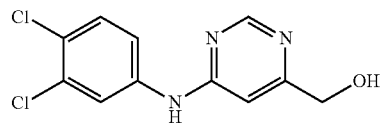

BBr$_3$ (0.399 ml, 4.22 mmol) was added dropwise to a stirred solution of N-(3,4-dichlorophenyl)-6-(methoxymethyl)pyrimidin-4-amine (0.3 g, 1.056 mmol) in DCM (4.0 mL) at 0° C. The mixture was further stirred for 30 min and poured onto ice water. The pH was adjusted to 10 using sat. Na$_2$CO$_3$ solution. The resulting suspension was extracted with ethyl acetate. The organic layer was isolated and dried over K$_2$CO$_3$ and concentrated to give (6-(3,4-dichlorophenylamino)pyrimidin-4-yl)methanol as a brown solid (0.275 g,

| Example Number | R$_1$ | R$_2$ | LCMS RT, min | LCMS Ion [M + H]$^+$ | $^1$H NMR |
|---|---|---|---|---|---|
| 94 | 4-Cl-phenyl-CH$_2$- | quinolin-2(1H)-one-6-yl | 3.43 | 395.1 | $^1$H NMR (400 MHz, DMSO-$d_6$) δ ppm 11.68 (s, 1H), 8.30 (d, J = 5.0 Hz, 1H), 7.96-7.66 (m, 2H), 7.44-7.13 (m, 7H), 6.71 (d, J = 5.0 Hz, 1H), 6.50 (d, J = 9.5 Hz, 1H), 5.01 (s, 2H), 4.50 (d, J = 6.5 Hz, 2H) |

Example 95

6-((6-(3,4-dichlorophenylamino)pyrimidin-4-yl)methoxy)quinolin-2(1H)-one trifluoroacetate

N-(3,4-dichlorophenyl)-6-(methoxymethyl)pyrimidin-4-amine

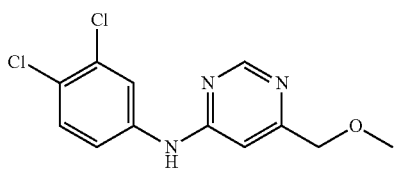 [SMILES: COCc1cc(Nc2ccc(Cl)c(Cl)c2)ncn1]

A mixture of 3,4-dichloroaniline (1.328 g, 8.20 mmol) and 4-chloro-6-(methoxymethyl)pyrimidine (0.65 g, 4.10 mmol) in dioxane (20.5 ml) was heated at 100° C. for 54 h, cooled to room temperature and concentrated onto Na$_2$SO$_4$. The residue was purified on silica gel using 50-100% ethyl acetate in 96%). $^1$H NMR (400 MHz, DMSO-$d_6$) δ ppm 11.05 (1H, br. s.), 8.92 (1H, s), 8.14 (1H, s), 7.71 (1H, d, J=8.78 Hz), 7.60 (1H, dd, J=8.78, 2.51 Hz), 7.05 (1H, s), 4.60 (2H, s). LCMS: R.T.=2.88; [M+H]$^+$=271.96.

6-(chloromethyl)-N-(3,4-dichlorophenyl)pyrimidin-4-amine

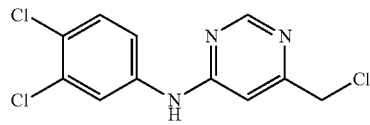 [SMILES: ClCc1cc(Nc2ccc(Cl)c(Cl)c2)ncn1]

Thionyl chloride (0.184 mL, 2.52 mmol) was added dropwise to a stirred solution of (6-((3,4-dichlorophenyl)amino)pyrimidin-4-yl)methanol (0.17 g, 0.629 mmol) in chloroform at 0° C. The mixture was allowed to warm to room temperature and further stirred for 18 h. After concentration, the crude product 6-(chloromethyl)-N-(3,4-dichlorophenyl)pyrimidin-4-amine (0.08 g, 75%) was used in the next step without purification. ¹H NMR (400 MHz, DMSO-d₆) δ ppm 10.85 (1H, br. s.), 8.81 (1H, s), 8.20 (1H, s), 7.64 (2H, s), 7.11 (1H, s), 4.76 (2H, s). LCMS: R.T.=3.48; [M+H]⁺=287.91.

6-((6-(3,4-dichlorophenylamino)pyrimidin-4-yl)methoxy)quinolin-2(1H)-one trifluoroacetate

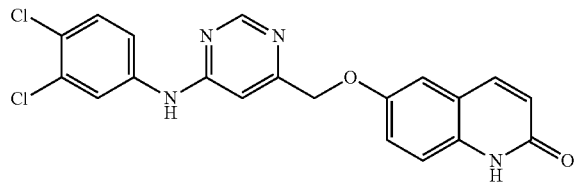 [SMILES: O=c1ccc2cc(OCc3cc(Nc4ccc(Cl)c(Cl)c4)ncn3)ccc2[nH]1]

A mixture of 6-hydroxyquinolin-2(1H)-one (0.015 g, 0.094 mmol), Cs₂CO₃ (0.051 g, 0.156 mmol) and 5-(chloromethyl)-N-(3,4-dichlorophenyl)pyrimidin-2-amine (0.03 g, 0.104 mmol) in DMF (4.9 mL) was stirred at room temperature for 18 h. The reaction was diluted with water and the resulting suspension filtered. The bright yellow filter cake was taken up in methanol and the mixture was stirred for 1 h. The suspension was filtered and the yellow solid was washed with methanol and dried. The solid was further stirred in DCM/MeOH for 2 days. The mixture was filtered, and the filter cake washed with methanol and dried to give a beige solid. The crude product was purified by reverse phase preparative HPLC (C-18) using a gradient of methanol/water/0.1% TFA as the mobile phase. 6-((6-(3,4-dichlorophenylamino)pyrimidin-4-yl)methoxy)quinolin-2(1H)-one trifluoroacetate was isolated as a beige solid (0.027 g, 10%). ¹H NMR (400 MHz, DMSO-d₆) δ ppm 11.72 (1H, br. s.), 10.18 (1H, s), 8.77 (1H, s), 8.21 (1H, s), 7.86 (1H, d, J=9.54 Hz), 7.46-7.70 (2H, m), 7.18-7.39 (3H, m), 6.95 (1H, s), 6.51 (1H, d, J=9.54 Hz), 5.16 (2H, s). LCMS: R.T.=3.51; [M+H]⁺=413.13.

The following compounds were synthesized by methods similar to that described for Example 95.

Example 98

6-((5-(3,4-dichlorophenylamino)pyrazin-2-yl)methoxy)quinolin-2(1H)-one

Methyl 5-(3,4-dichlorophenylamino)pyrazine-2-carboxylate

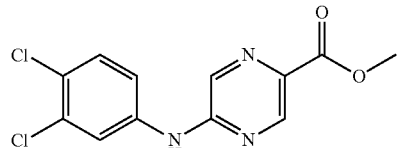

A mixture of 3,4-dichloroaniline (1.127 g, 6.95 mmol) and methyl 5-chloropyrazine-2-carboxylate (0.6 g, 3.48 mmol) in dioxane (32 mL) was heated at 100° C. for 7 days, then cooled to room temperature and concentrated. The residue was triturated with methanol and filtered. The brown filter cake was washed with methanol and dried to yield methyl 5-(3,4-dichlorophenylamino)pyrazine-2-carboxylate (0.53 g, 51%). ¹H NMR (400 MHz, DMSO-d₆) δ ppm 10.44 (1H, s), 8.81 (1H, d, J=1.26 Hz), 8.30 (1H, d, J=1.51 Hz), 8.21 (1H, d, J=2.26 Hz), 7.46-7.73 (2H, m), 3.58 (2H, s). LCMS: R.T.=4.07; [M+H]⁺=298.12.

(5-(3,4-dichlorophenylamino)pyrazin-2-yl)methanol

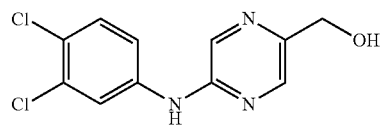 [SMILES: OCc1cnc(Nc2ccc(Cl)c(Cl)c2)cn1]

A suspension of methyl 5-((3,4-dichlorophenyl)amino)pyrazine-2-carboxylate (0.53 g, 1.778 mmol) in THF (18 mL) was cooled at −78° C. and 1M solution of DIBAL-H (5.33 ml,

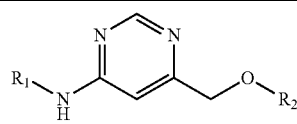

| Example Number | R₁ | R₂ | LCMS RT min | LCMS Ion [M + H]⁺ | ¹H NMR |
|---|---|---|---|---|---|
| 96 | 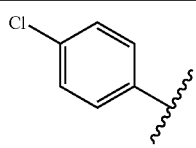 | 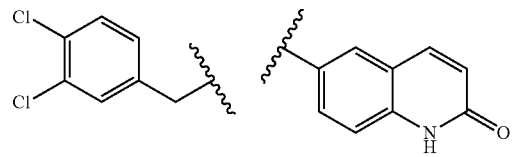 | 3.07 | 379.14 | ¹H NMR (400 MHz, DMSO-d₆) δ ppm 11.72 (br. s., 1H), 10.06 (br. s., 1H), 8.71 (s, 1H), 7.87 (d, J = 9.8 Hz, 1H), 7.73 (d, J = 9.0 Hz, 2H), 7.47-7.37 (m, 2H), 7.36-7.25 (m, 3H), 6.93 (s, 1H), 6.52 (d, J = 9.5 Hz, 1H), 5.15 (s, 2H) |
| 97 | | | 3.12 | 427.00 | ¹H NMR (400 MHz, DMSO-d₆) δ ppm 11.71 (1H, br. s.), 8.58 (2H, br. s.), 7.85 (1H, d, J = 9.54 Hz), 7.48-7.69 (2H, m), 7.15-7.39 (3H, m), 6.76 (1H, br. s.), 6.40-6.56 (1H, m), 5.08 (2H, br. s.), 4.61 (2H, br. s.). |

5.33 mmol) in toluene was added. The mixture was stirred for 1.5 h while warming to room temperature. The reaction mixture was diluted with THF (20 mL) and quenched with Na$_2$SO$_4$.10H$_2$O followed by a few drops of water. The mixture was stirred at room temperature for 18 h, then filtered through a pad of Celite topped with silica gel. The pad was washed with ethyl acetate and the filtrate concentrated. The residue was purified on silica gel using 40-100% ethyl acetate in hexanes. The desired fractions were concentrated to give (5-(3,4-dichlorophenylamino)pyrazin-2-yl)methanol as a yellow solid (0.293 g, 61%). $^1$H NMR (400 MHz, DMSO-d$_6$) δ ppm 9.80 (1H, s), 8.02-8.34 (3H, m), 7.46-7.66 (2H, m), 5.36 (1H, t, J=5.77 Hz), 4.51 (2H, d, J=5.77 Hz). LCMS: R.T.=3.65; [M+H]$^+$=269.96.

6-((5-(3,4-dichlorophenylamino)pyrazin-2-yl)methoxy)quinolin-2(1H)-one

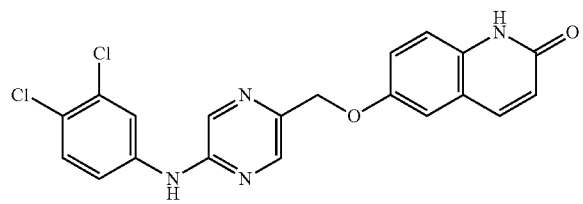 [SMILES: O=c1ccc2cc(OCc3cnc(Nc4ccc(Cl)c(Cl)c4)cn3)ccc2[nH]1]

A solution of Ph$_3$P (0.07 g, 0.267 mmol) in THF (1.7 mL) was cooled to 0° C. under N2 and DEAD (0.076 ml, 0.481 mmol) was added dropwise. The mixture was stirred for 10 min, then 6-hydroxyquinolin-2(1H)-one (0.072 g, 0.444 mmol) was added. After stirring for 5 min, a solution of (5-((3,4-dichlorophenyl)amino)pyrazin-2-yl)methanol (0.1 g, 0.370 mmol) in THF (2 mL) was added. The reaction was stirred at room temperature overnight. The mixture was concentrated and partially purified by flash chromatography on silica gel using 30-100% ethyl acetate in hexanes, then 5-10% methanol in ethyl acetate. The desired fractions were concentrated to a solid, which was redissolved in DMF. Water was added to the vigorously stirred solution until a suspension formed. After stirring 18 h, the off-white solid was filtered, washed with methanol, and dried to yield 6-((5-(3,4-dichlorophenylamino)pyrazin-2-yl)methoxy)quinolin-2(1H)-one (0.02 g, 13%). $^1$H NMR (400 MHz, DMSO-d$_6$) δ ppm 11.67 (1H, s), 9.97 (1H, s), 8.40 (1H, d, J=1.00 Hz), 8.28 (1H, d, J=1.51 Hz), 8.20 (1H, d, J=2.26 Hz), 7.86 (1H, d, J=9.79 Hz), 7.49-7.64 (2H, m), 7.37 (1H, s), 7.17-7.32 (2H, m), 6.51 (1H, dd, J=9.54, 2.01 Hz), 5.12 (2H, s). LCMS: R.T.=4.09; [M+H]$^+$=412.93.

The following compounds were synthesized by methods similar to that described for Example 98.

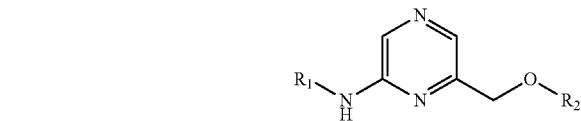

| Example Number | R$_1$ | R$_2$ | LCMS RT, min | LCMS Ion [M + H]$^+$ | $^1$H NMR |
|---|---|---|---|---|---|
| 99 | 4-chlorophenyl | quinolin-2(1H)-on-6-yl | 3.78 | 379.11 | $^1$H NMR (500 MHz, DMSO-d$_6$) δ ppm 11.65 (s, 1H), 9.76 (s, 1H), 8.41-8.14 (m, 2H), 7.85 (d, J = 9.6 Hz, 1H), 7.77-7.64 (m, 2H), 7.37-7.31 (m, 3H), 7.28-7.10 (m, 2H), 6.50 (dd, J = 9.5, 1.8 Hz, 1H), 5.09 (s, 2H) |
| 100 | 4-chlorobenzyl | quinolin-2(1H)-on-6-yl | 3.60 | 393.08 | $^1$H NMR (400 MHz, DMSO-d$_6$) δ ppm 11.66 (s, 1H), 8.11 (d, J = 1.0 Hz, 1H), 8.01 (d, J = 1.3 Hz, 1H), 7.89-7.74 (m, 2H), 7.43-7.30 (m, 5H), 7.29-7.17 (m, 2H), 6.50 (dd, J = 9.5, 1.8 Hz, 1H), 4.99 (s, 2H), 4.50 (d, J = 5.8 Hz, 2H) |
| 101 | 3,4-dichlorobenzyl | quinolin-2(1H)-on-6-yl | 3.07 | 427.17 | $^1$H NMR (400 MHz, DMSO-d$_6$) δ ppm 11.66 (1H, s), 8.12 (1H, d, J = 1.26 Hz), 8.03 (1H, d, J = 1.51 Hz), 7.79-7.89 (2H, m), 7.54-7.63 (2H, m), 7.28-7.38 (2H, m), 7.15-7.28 (2H, m), 6.50 (1H, dd, J = 9.54, 1.76 Hz), 4.99 (2H, s), 4.51 (2H, d, J = 6.02 Hz) |

Example 102

6-(6-(4-(trifluoromethoxy)benzylamino)pyridazin-3-yloxy)quinolin-2(1H)-one 6-((6-chloropyridazin-3-yl)oxy)quinolin-2(1H)-one

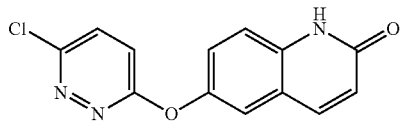 [SMILES: O=c1ccc2cc(Oc3ccc(Cl)nn3)ccc2[nH]1]

To a stirring solution of 6-hydroxyquinolin-2(1H)-one (0.5 g, 3.10 mmol) in DMF (20 mL) at room temperature was added NaH (0.124 g, 3.10 mmol). The reaction mixture was stirred for 30 min, then 3,6-dichloropyridazine (0.555 g, 3.72 mmol) was added. The reaction was stirred at 110° C. overnight. The reaction was quenched with water and extracted with EtOAc (3×25 mL). The combined organic layers were dried over MgSO$_4$ and concentrated under vacuum to a tan solid. This was purified by flash chromatography on silica gel using 1:1 EtOAc/hexane to yield a mixture of 6-hydroxyquinolin-2(1H)-one and 6-((6-chloropyridazin-3-yl)oxy)quinolin-2(1H)-one as a tan solid (0.3 g, 12%). $^1$H NMR (400 MHz, METHANOL-d$_4$) δ ppm 7.99 (d, J=9.5 Hz, 1H), 7.94-7.82 (m, 1H), 7.60 (s, 1H), 7.55-7.45-7.03 (m, 3H), 6.69 (m, 1H). LCMS: R.T.=1.418 min; [M+H]$^+$=272.2.

6-((6-((4-(trifluoromethoxy)benzyl)amino)pyridazin-3-yl)oxy)quinolin-2(1H)-one

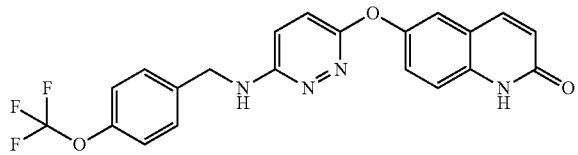 [SMILES: O=c1ccc2cc(Oc3ccc(NCc4ccc(OC(F)(F)F)cc4)nn3)ccc2[nH]1]

To a suspension of 6-((6-chloropyridazin-3-yl)oxy)quinolin-2(1H)-one (0.032 g, 0.117 mmol) in dioxane (2.0 mL) at room temperature was added 4-(trifluoromethoxy)benzylamine (0.091 mL, 0.585 mmol), (R)-(−)-1-[(S)-2-(Dicyclohexylphosphino)ferrocenyl]ethyldi-t-butylphosphine (3.28 mg, 5.85 μmol), palladium (II) acetate (1.313 mg, 5.85 μmol) and sodium-t-butoxide (0.014 mL, 0.164 mmol). The reaction mixture was stirred in a sealed tube at 110° C. overnight, then concentrated under vacuum to a yellow oil. This was purified by prep HPLC to yield 6-((6-((4-(trifluoromethoxy)benzyl)amino)pyridazin-3-yl)oxy)quinolin-2(1H)-one as a white solid (4 mg, 5%). $^1$H NMR (500 MHz, METHANOL-d$_4$) δ ppm 7.96 (d, J=9.5 Hz, 2H), 7.67-7.34 (m, 8H), 6.68 (d, J=9.6 Hz, 1H), 4.59 (s, 2H). LCMS: R.T.=1.738 min; [M+H]$^+$=429.08.

Example 103

4-(2-(1H-indazol-5-yl)ethyl)-N-(4-(trifluoromethyl)phenyl)-1,3,5-triazin-2-amine N-(4-(trifluoromethyl)phenyl)-4-vinyl-1,3,5-triazin-2-amine

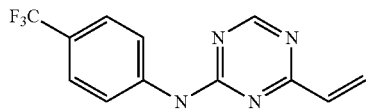

To a solution of 4-chloro-N-(4-(trifluoromethyl)phenyl)-1,3,5-triazin-2-amine (0.5 g, 1.821 mmol) in dioxane (8 mL) and water (2 mL) were added trivinylboroxin (0.588 g, 3.64 mmol), cesium carbonate (1.780 g, 5.46 mmol). The reaction mixture was flushed with nitrogen for 10 min and Tetrakis (0.210 g, 0.182 mmol) was added. The reaction mixture was heated at 90° C. for 2 h then filtered through a pad of celite and washed with ethyl acetate. The organic layer was washed with water, dried over anhydrous sodium sulfate and concentrated. The crude product was purified by flash chromatography on silica gel using 15% ethyl acetate in hexane to give N-(4-(trifluoromethyl)phenyl)-4-vinyl-1,3,5-triazin-2-amine as a white solid (0.08 g, 12.21% yield). LCMS: R.T.=1.14 min; [M+H]$^+$=267.1.

(E)-4-(2-(1-(tetrahydro-2H-pyran-2-yl)-1H-indazol-5-yl)vinyl)-N-(4-(trifluoromethyl)phenyl)-1,3,5-triazin-2-amine

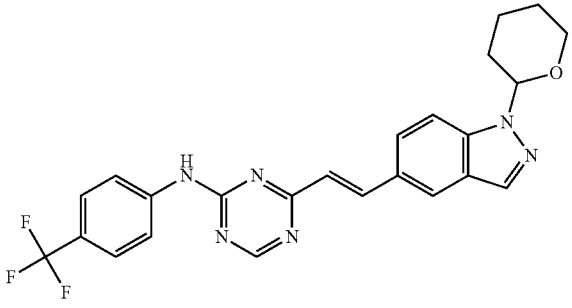 [SMILES: FC(F)(F)c1ccc(Nc2ncnc(/C=C/c3ccc4c(cnn4C4CCCCO4)c3)n2)cc1]

To a stirred solution of 5-iodo-1-(tetrahydro-2H-pyran-2-yl)-1H-indazole (0.05 g, 0.152 mmol) in ACN (5 mL) were added N-(4-(trifluoromethyl)phenyl)-4-vinyl-1,3,5-triazin-2-amine (0.041 g, 0.152 mmol), tri-o-tolylphosphine (0.019 g, 0.061 mmol) and triethylamine (0.064 mL, 0.457 mmol). Nitrogen was purged for 5 minutes. Tris(dibenzylideneacetone)dipalladium(0) (0.014 g, 0.015 mmol) was added and the reaction mixture was heated at 90° C. overnight. The reaction mixture was filtered through a pad of celite, washed with ethyl acetate, and the organic layer was concentrated. The crude product was purified by flash chromatography on silica gel using 25% ethyl acetate in hexane to give (E)-4-(2-(1-(tetrahydro-2H-pyran-2-yl)-1H-indazol-5-yl)vinyl)-N-(4-(trifluoromethyl)phenyl)-1,3,5-triazin-2-amine as a pale yellow solid (0.04 g, 42% yield). LCMS: R.T.=1.21 min; [M+H]$^+$=467.33.

4-(2-(1-(tetrahydro-2H-pyran-2-yl)-1H-indazol-5-yl)ethyl)-N-(4-(trifluoromethyl)phenyl)-1,3,5-triazin-2-amine

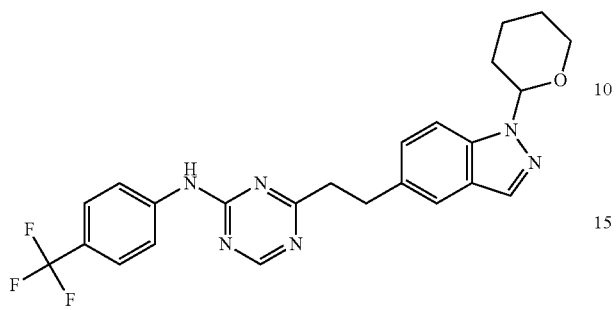

To a solution of (E)-4-(2-(1-(tetrahydro-2H-pyran-2-yl)-1H-indazol-5-yl)vinyl)-N-(4-(trifluoromethyl)phenyl)-1,3,5-triazin-2-amine (0.03 g, 0.064 mmol) in ethyl acetate (3 mL), Pd—C (0.014 g, 0.129 mmol) was added and the reaction mixture was stirred at room temperature under $H_2$ overnight. The reaction mixture was filtered through a pad of celite, washed with ethyl acetate, and concentrated to get 4-(2-(1-(tetrahydro-2H-pyran-2-yl)-1H-indazol-5-yl)ethyl)-N-(4-(trifluoromethyl)phenyl)-1,3,5-triazin-2-amine as a yellow gum (0.03 g, 75% yield). LCMS: R.T.=1.06 min; [M+H]+=469.27.

4-(2-(1H-indazol-5-yl)ethyl)-N-(4-(trifluoromethyl)phenyl)-1,3,5-triazin-2-amine

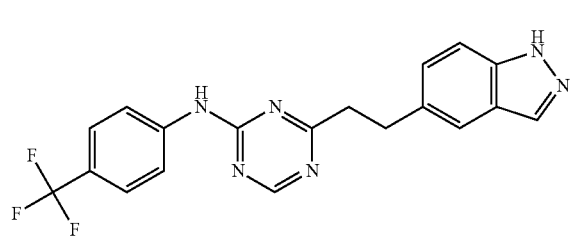 [SMILES: FC(F)(F)c1ccc(Nc2ncnc(CCc3ccc4[nH]ncc4c3)n2)cc1]

To a solution of 4-(2-(1-(tetrahydro-2H-pyran-2-yl)-1H-indazol-5-yl)ethyl)-N-(4-(trifluoromethyl)phenyl)-1,3,5-triazin-2-amine (0.03 g, 0.064 mmol) in DCM (2 mL) cooled to 0° C., TFA (0.025 mL, 0.320 mmol) was added and the reaction mixture was stirred at 23° C. overnight. The reaction mixture was concentrated, washed with diethyl ether, and purified by preparative HPLC on a SY C18 column (20×19 mm) using 0-100% mobile phase B (ACN) in mobile phase A (10 mM NH4OAc) over 17 min to give 4-(2-(1H-indazol-5-yl)ethyl)-N-(4-(trifluoromethyl)phenyl)-1,3,5-triazin-2-amine as a white solid (4 mg, 16%).

$^1$HNMR: 400 MHz, DMSO-d6: δ ppm 3.08 (t, J=6.80 Hz, 2H), 3.21 (t, J=8.00 Hz, 2H), 7.26 (dd, J=1.20, 8.60 Hz, 1H), 7.46 (d, J=8.40 Hz, 1H), 7.59 (s, 1H), 7.67 (d, J=8.80 Hz, 2H), 7.93-7.97 (m, 3H), 8.77 (s, 1H), 10.57 (s, 1H), 12.94 (s, 1H). LCMS (ES-API), m/z 385 (M+H).

Example 104

5-(2-(1H-indazol-5-yl)ethyl)-N-(3-chloro-4-(difluoromethoxy)phenyl)pyrimidin-2-amine

1-(tetrahydro-2H-pyran-2-yl)-5-vinyl-1H-indazole

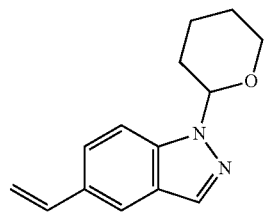 [SMILES: C=Cc1ccc2c(cnn2C2CCCCO2)c1]

To a solution of 5-bromo-1-(tetrahydro-2H-pyran-2-yl)-1H-indazole (0.5 g, 1.778 mmol) in toluene (10 mL) and water (10 mL) were added $K_2CO_3$ (0.492 g, 3.56 mmol), trivinylboroxin pyridine complex (0.514 g, 2.134 mmol), and Tetrakis (0.206 g, 0.178 mmol). The reaction mixture was heated at 110° C. for 4 h. The reaction mixture was concentrated and the residue was extracted with ethyl acetate and washed with water. The organic layer was dried over anhydrous sodium sulfate and concentrated to give 1-(tetrahydro-2H-pyran-2-yl)-5-vinyl-1H-indazole (0.3 g, 74%). LCMS (ES-API), m/z 144 (M-THP).

5-bromo-N-(3-chloro-4-(difluoromethoxy)phenyl)pyrimidin-2-amine

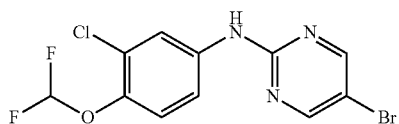 [SMILES: FC(F)Oc1ccc(Nc2ncc(Br)cn2)cc1Cl]

To a solution of 3-chloro-4-(difluoromethoxy)aniline (0.814 g, 4.20 mmol) in butan-1-ol (10 mL), were added DIPEA (2.203 mL, 12.61 mmol) and 2,5-dibromopyrimidine (1 g, 4.20 mmol). The reaction mixture was stirred at 120° C. for 12 h and concentrated. The crude product was purified by flash chromatography on silica gel using 3% ethyl acetate in petroleum ether to give 5-bromo-N-(3-chloro-4-(difluoromethoxy)phenyl)pyrimidin-2-amine (0.8 g, 64%). LCMS (ES-ES), m/z 349.98.

(E)-N-(3-chloro-4-(difluoromethoxy)phenyl)-5-(2-(1-(tetrahydro-2H-pyran-2-yl)-1H-indazol-5-yl)vinyl)pyrimidin-2-amine

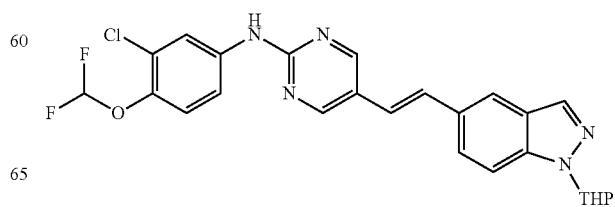

To a solution of 5-bromo-N-(3-chloro-4-(difluoromethoxy)phenyl)pyrimidin-2-amine (0.3 g, 0.856 mmol) in DMF (5 mL) were added 1-(tetrahydro-2H-pyran-2-yl)-5-vinyl-1H-indazole (0.163 g, 0.713 mmol), tetrabutylammonium chloride hydrate (0.317 g, 1.070 mmol), triethylamine (0.298 mL, 2.140 mmol), and PdOAc$_2$ (0.016 g, 0.071 mmol). The reaction mixture was heated at 120° C. for 12 h then concentrated. Ethyl acetate was added. The mixture was filtered through celite, washed with water, and the organic layer was dried over anhydrous sodium sulfate and the crude product was purified by flash chromatography on silica gel using 15% ethyl acetate in petroleum ether to give 1H-indazol-5-yl)vinyl)pyrimidin-2-amine (0.29 g, 82%). LCMS (ES-API), RT: 2.33 m/z 498.2 (M+H).

N-(3-chloro-4-(difluoromethoxy)phenyl)-5-(2-(1-(tetrahydro-2H-pyran-2-yl)-1H-indazol-5-yl)ethyl)pyrimidin-2-amine

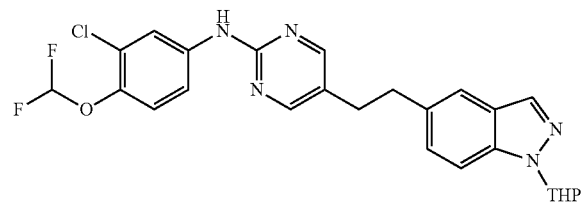

To a solution of N-(3-chloro-4-(difluoromethoxy)phenyl)-5-(2-(1-(tetrahydro-2H-pyran-2-yl)-1H-indazol-5-yl)vinyl)pyrimidin-2-amine (0.10 g, 0.201 mmol) in ethyl acetate (10 mL) was added Pd/C (0.214 g, 2.008 mmol). The reaction mixture was stirred at room temperature under hydrogen for 12 h. The reaction mixture was filtered through celite and the filtrate was concentrated to give N-(3-chloro-4-(difluoromethoxy)phenyl)-5-(2-(1-(tetrahydro-2H-pyran-2-yl)-1H-indazol-5-yl)ethyl)pyrimidin-2-amine (0.16 g, 80%). LCMS (ES-API), RT: 2.21 m/z 500.2 (M+H).

5-(2-(1H-indazol-5-yl)ethyl)-N-(3-chloro-4-(difluoromethoxy)phenyl)pyrimidin-2-amine

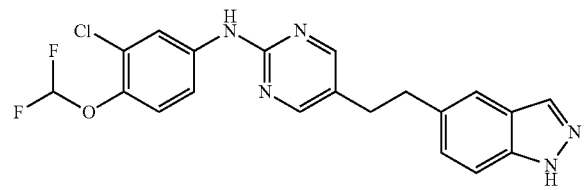 [SMILES: FC(F)Oc1ccc(Nc2ncc(CCc3ccc4[nH]ncc4c3)cn2)cc1Cl]

To N-(3-chloro-4-(difluoromethoxy)phenyl)-5-(2-(1-(tetrahydro-2H-pyran-2-yl)-1H-indazol-5-yl)ethyl)pyrimidin-2-amine (0.075 g, 0.150 mmol) in DCM (5 mL) was added TFA (0.116 mL, 1.500 mmol) and the reaction mixture was stirred at room temperature for 12 h. The reaction mixture was concentrated and the crude product purified by preparative HPLC on a Symmetry C18 column (19×300 mm, 7 µm) using 0-100% mobile phase B (ACN) in mobile phase A (10 mM ammonium acetate) to give 5-(2-(1H-indazol-5-yl)ethyl)-N-(3-chloro-4-(difluoromethoxy)phenyl)pyrimidin-2-amine as an off white solid (0.012 g, 19% yield). $^1$HNMR 400 MHz, DMSO-d6: δ 2.85 (t, J=15.60 Hz, 2H), 2.99 (t, J=14.80 Hz, 2H), 6.95-7.31 (m, 3H), 7.46 (d, J=8.40 Hz, 1H), 7.54 (s, 1H), 7.65-7.68 (m, 1H), 7.98 (s, 1H), 8.08 (d, J=2.80 Hz, 1H), 8.36 (s, 2H), 9.76 (s, 1H), 12.95 (s, 1H). LCMS (ES-API), RT: 2.15 min, m/z 414 (M−H).

Example 105

6-(2-(2-(3-chloro-4-(difluoromethoxy)phenylamino)pyrimidin-5-yl)ethyl)quinolin-2(1H)-one 1-((2-(trimethylsilyl)ethoxy)methyl)-6-vinylquinolin-2(1H)-one

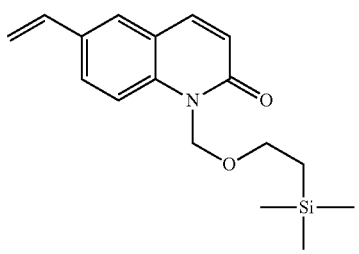 [SMILES: C=Cc1ccc2c(ccc(=O)n2COCC[Si](C)(C)C)c1]

To a solution of 6-bromo-1-((2-(trimethylsilyl)ethoxy)methyl)quinolin-2(1H)-one (1 g, 2.82 mmol) in toluene (20 mL) and water (20.00 mL) were added trivinylboraxin (0.684 g, 4.23 mmol), K2CO3 (0.780 g, 5.64 mmol). The reaction mixture was purged with N$_2$ for 15 min, then Tetrakis (0.652 g, 0.564 mmol) was added and the reaction mixture was heated to 110° C. for 12 h. The reaction mixture was concentrated and dissolved in ethyl acetate and washed with water. The organic layer was dried over anhydrous sodium sulfate, and concentrated to get the 1-((2-(trimethylsilyl)ethoxy)methyl)-6-vinylquinolin-2(1H)-one (0.8 g, 94%), used without further purification. LCMS (ES-API), RT: 2.17 m/z 302.2 (M+H).

(E)-6-(2-(2-(3-chloro-4-(difluoromethoxy)phenylamino)pyrimidin-5-yl)vinyl)-1-((2-(trimethylsilyl)ethoxy)methyl)quinolin-2(1H)-one

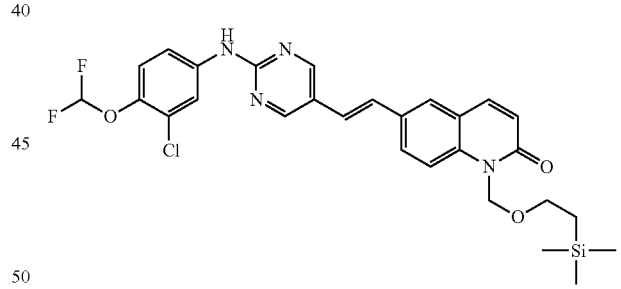

To a solution of 5-bromo-N-(3-chloro-4-(difluoromethoxy)phenyl)pyrimidin-2-amine (0.3 g, 0.856 mmol) in DMF (5 mL), were added 1-((2-(trimethylsilyl)ethoxy)methyl)-6-vinylquinolin-2(1H)-one (0.258 g, 0.856 mmol) triethylamine (0.358 mL, 2.57 mmol), tetrabutylammonium chloride, hydrate (0.380 g, 1.284 mmol) and PdOAc$_2$ (0.019 g, 0.086 mmol). The reaction mixture was heated at 120° C. for 12 h. The reaction mixture was concentrated, dissolved in ethyl acetate, filtered through celite, and washed with water. The organic layer was dried over anhydrous sodium sulfate, concentrated and purified by flash chromatography on silica gel using 15% ethyl acetate in petroleum ether to give (E)-6-(2-(2-(3-chloro-4-(difluoromethoxy)phenylamino)pyrimidin-5-yl)vinyl)-1-((2-(trimethylsilyl)ethoxy)methyl)quinolin-2(1H)-one (0.24 g, 49%). LCMS (ES-API), RT: 2.56 m/z 571.2 (M+H).

6-(2-(2-(3-chloro-4-(difluoromethoxy)phenylamino) pyrimidin-5-yl)ethyl)-1-((2-(trimethylsilyl)ethoxy) methyl)quinolin-2(1H)-one

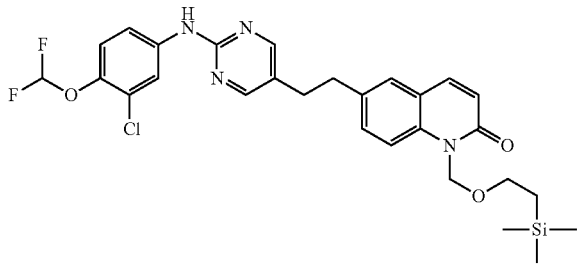 [SMILES: C[Si](C)(C)CCOCn1c(=O)ccc2cc(CCc3cnc(Nc4ccc(OC(F)F)c(Cl)c4)nc3)ccc21]

To 6-(2-(2-((3-chloro-4-(difluoromethoxy)phenyl)amino) pyrimidin-5-yl)vinyl)-1-((2-(trimethylsilyl)ethoxy)methyl) quinolin-2(1H)-one (0.1 g, 0.175 mmol) in ethyl acetate (10 mL) was added Pd/C (0.186 g, 1.751 mmol) and the reaction mixture was stirred at room temperature under an atmosphere of $H_2$ gas for 12 hours. The reaction mass was filtered through celite and the filtrate was concentrated to give 6-(2-(2-(3-chloro-4-(difluoromethoxy)phenylamino)pyrimidin-5-yl) ethyl)-1-((2-(trimethylsilyl)ethoxy)methyl)quinolin-2(1H)-one (0.075 g, 74%). LCMS (ES-API), RT: 2.56 m/z 575.2 (M+H).

6-(2-(2-(3-chloro-4-(difluoromethoxy)phenylamino) pyrimidin-5-yl)ethyl)quinolin-2(1H)-one

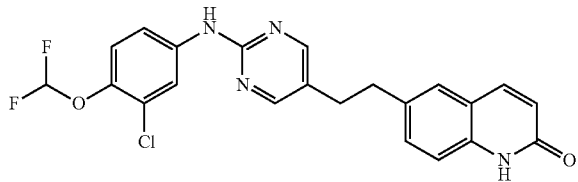 [SMILES: O=c1ccc2cc(CCc3cnc(Nc4ccc(OC(F)F)c(Cl)c4)nc3)ccc2[nH]1]

To a solution of 6-(2-(2-((3-chloro-4-(difluoromethoxy) phenyl)amino)pyrimidin-5-yl)ethyl)-1-((2-(trimethylsilyl) ethoxy)methyl)quinolin-2(1H)-one (0.05 g, 0.087 mmol) in DCM (5 mL) was added TFA (0.067 mL, 0.872 mmol) and stirred at room temperature for 12 h. The reaction mixture was concentrated and purified by preparative HPLC on a Symmetry C8 column (19×250 mm, 7 μm) using 0-100% mobile phase B (ACN) in mobile phase A (10 mM ammonium acetate) to give 6-(2-(2-((3-chloro-4-(difluoromethoxy)phenyl)amino)pyrimidin-5-yl)ethyl)quinolin-2(1H)-one as an off white solid (0.017 g, 44% yield). 1HNMR 400 MHz, DMSO-d6: δ 2.83 (t, J=14.80 Hz, 2H), 2.93 (t, J=14.80 Hz, 2H), 6.46-6.49 (m, 1H), 6.95-7.39 (m, 4H), 7.48 (s, 1H), 7.65-7.68 (m, 1H), 7.84 (d, J=9.60 Hz, 1H), 8.09 (d, J=2.40 Hz, 1H), 8.37 (s, 2H), 9.78 (s, 1H), 11.68 (s, 1H). LCMS (ES-API), RT: 2.95 min, m/z 441.0 (M−H)−.

Example 106

6-(2-(2-((4-(difluoromethoxy)phenyl)amino)pyrimidin-5-yl)cyclopropyl)-1-((2-(trimethylsilyl)ethoxy) methyl)quinolin-2(1H)-one

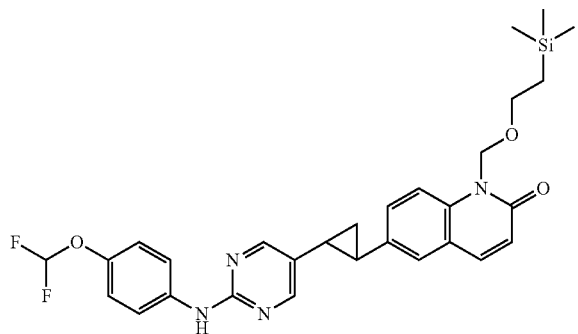 [SMILES: C[Si](C)(C)CCOCn1c(=O)ccc2cc(C3CC3c3cnc(Nc4ccc(OC(F)F)cc4)nc3)ccc21]

To a stirred solution of (E)-6-(2-(2-((4-(difluoromethoxy) phenyl)amino)pyrimidin-5-yl)vinyl)-1-((2-(trimethylsilyl) ethoxy)methyl)quinolin-2(1H)-one (0.15 g, 0.280 mmol) in diethyl ether (10 mL) was added $PdOAc_2$ (6.28 mg, 0.028 mmol). The reaction mixture was cooled to −10° C., and a cold solution of diazomethane in ether (generated from aqueous KOH (0.45 g) and NMU (0.6 g) at −15° C.) was added. The reaction mixture was stirred at room temperature for 12 h. The reaction mixture was filtered through celite, diluted with diethyl ether, and washed with water and saturated NaCl solution. The organic layer was dried over sodium sulfate, concentrated, and purified by flash chromatography on silica gel column using 15% ethyl acetate in hexane to give 6-(2-(2-((4-(difluoromethoxy)phenyl)amino)pyrimidin-5-yl)cyclopropyl)-1-((2-(trimethylsilyl)ethoxy)methyl)quinolin-2 (1H)-one as a yellow gum (0.075 g, 49%). LCMS: RT 2.317 min, (M+H) 551.

Example 107

4-(2-(2-((4-(difluoromethoxy)phenyl)amino)pyrimidin-5-yl)ethyl)phenol

(E)-5-(4-(benzyloxy)styryl)-N-(4-(difluoromethoxy) phenyl)pyrimidin-2-amine

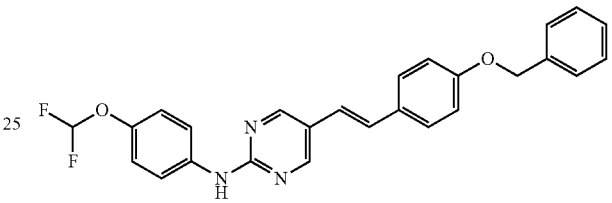

To a solution of N-(4-(difluoromethoxy)phenyl)-5-vinylpyrimidin-2-amine (0.102 g, 0.387 mmol) in ACN (3 mL) were added 1-(benzyloxy)-4-iodobenzene (0.1 g, 0.322 mmol), tris(dibenzylideneacetone)dipalladium(0) chloroform adduct (0.033 g, 0.032 mmol), tri-o-tolylphosphine (0.039 g, 0.129 mmol), and TEA (0.135 mL, 0.967 mmol). The reaction mixture was flushed with $N_2$ and heated at 90° C. overnight. Solvent was evaporated, and the residue was dissolved in ethyl acetate, filtered through celite and concentrated. The crude product was purified by flash chromatography on silica gel using 30% ethyl acetate in hexanes to give (E)-5-(4-(benzyloxy)styryl)-N-(4-(difluoromethoxy)phenyl)pyrimidin-2-amine (0.1 g, 70%). 1H NMR (400 MHz, DMSO-d6) δ ppm 5.14 (s, 2H), 6.93-7.30 (m, 7H), 7.34-7.52 (m, 2H), 7.78-7.80 (m, 2H), 8.71 (s, 2H), 9.82 (s, 1H). LCMS: RT 1.18 min, (M+H)+446.6.

4-(2-(2-((4-(difluoromethoxy)phenyl)amino)pyrimidin-5-yl)ethyl)phenol

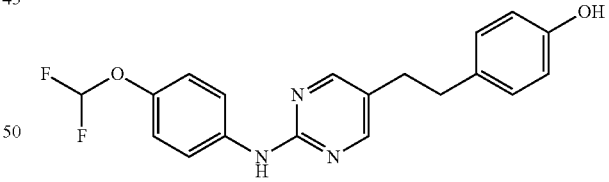

To a solution of (E)-5-(4-(benzyloxy)styryl)-N-(4-(difluoromethoxy)phenyl)pyrimidin-2-amine (0.04 g, 0.090 mmol) in methanol (5 mL) was added Pd/C (0.03 g, 0.282 mmol) and stirred at room temperature under $H_2$ (1 atom) for 3 h. The reaction mass was filtered through Celite, concentrated and purified by preparative HPLC on a Waters Xbridge C18 column (19×150 mm, 5 μm) using 0-100% mobile phase B (95:5 Acetonitrile:water with 10 mM $NH_4OAc$) in mobile phase A (5:95 Acetonitrile:water with 10 mM $NH_4OAc$) to give 4-(2-(2-((4-(difluoromethoxy)phenyl)amino)pyrimidin-5-yl) ethyl)phenol (0.013 g, 42%). 1H NMR (300 MHz, DMSO-d6) δ ppm 2.73 (s, 4H), 6.66 (d, J=8.40 Hz, 2H), 6.83-7.35 (m, 5H), 7.71-7.79 (m, 2H), 8.26 (s, 2H), 9.15 (br. s., 1H), 9.55 (s, 1H). LCMS: RT 2.14 min, (M+H)+358.1.

The following compounds were synthesized by methods similar to those described for the previous examples.

| Ex. | R₁ | R₂ | Linker | LCMS RT, min | LCMS Ion [M + H]⁺ | ¹H NMR |
|---|---|---|---|---|---|---|
| 108 | 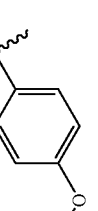 | 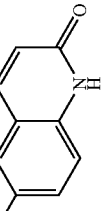 |  | 1.97 | 427.2 | 400 MHz, DMSO-d6: δ ppm 2.83 (t, J = 14.40 Hz, 2H), 2.93 (t, J = 14.40 Hz, 2H), 6.46-6.49 (m, 1H), 7.23-7.28 (m, 3H), 7.37-7.39 (m, 1H), 7.48 (s, 1H), 7.82-7.85 (m, 3H), 8.33 (s, 2H), 9.71 (s, 1H), 11.68 (s, 1H) |
| 109 | 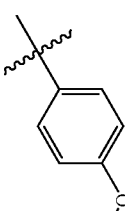 | 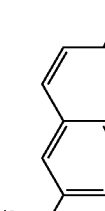 | 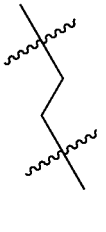 | 1.89 | 409.2 | 400 MHz, DMSO-d6: δ ppm 2.82 (t, J = 14.80 Hz, 2H), 2.92 (t, J = 14.80 Hz, 2H), 6.46-6.49 (m, 1H), 6.91-7.28 (m, 4H), 7.37-7.39 (m, 1H), 7.48 (s, 1H), 7.75 (d, J = 8.80 Hz, 1H), 7.84 (d, J = 9.60 Hz, 1H), 8.32 (d, J = 6.40 Hz, 2H), 9.56 (s, 1H), 11.68 (s, 1H) |
| 110 | 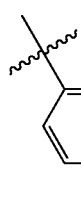 | 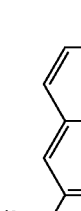 |  | 1.93 | 420.8 | 400 MHz, DMSO-d6: δ ppm 1.47-1.53 (m, 2H), 2.09-2.14 (m, 1H), 2.30-2.35 (m, 1H), 6.47-6.50 (m, 1H), 6.91-7.29 (m, 4H), 7.36-7.38 (m, 1H), 7.48 (d, J = 1.60 Hz, 1H), 7.76-7.78 (m, 1H), 7.84 (d, J = 9.60 Hz, 1H), 8.38 (s, 1H), 9.61 (s, 1H), 11.67 (s, 1H) |

| Ex. | R₁ | R₂ | Linker | LCMS RT, min | LCMS Ion [M + H]⁺ | ¹H NMR |
|---|---|---|---|---|---|---|
| 111 | 4-(difluoromethoxy)phenyl | 1H-indazol-4-yl | butylene | 2.05 | 381.7 | 400 MHz, DMSO-d6: δ ppm 2.91 (t, J = 15.60 Hz, 2H), 3.19 (t, J = 15.60 Hz, 2H), 6.90-7.29 (m, 5H), 7.37 (d, J = 8.40 Hz, 1H), 7.74-7.76 (m, 2H), 8.21 (s, 1H), 8.33 (s, 2H), 9.58 (s, 1H), 13.03 (s, 1H) |
| 112 | 4-(difluoromethoxy)phenyl | 1H-indazol-5-yl | butylene | 1.93 | 382.2 | 400 MHz, DMSO-d6: δ ppm 2.84 (t, J = 15.20 Hz, 2H), 2.98 (t, J = 14.80 Hz, 2H), 6.91-7.28 (m, 4H), 7.45-7.54 (m, 2H), 7.74-7.76 (m, 2H), 7.98 (s, 1H), 8.29 (s, 2H), 9.55 (s, 1H), 12.95 (s, 1H) |
| 113 | 4-(difluoromethoxy)phenyl | 1H-indazol-6-yl | butylene | 1.94 | 382.2 | 400 MHz, DMSO-d6: δ ppm 2.85 (t, J = 15.20 Hz, 2H), 3.01 (t, J = 15.20 Hz, 2H), 6.91-7.30 (m, 5H), 7.67 (d, J = 8.00 Hz, 1H), 7.73-7.77 (m, 2H), 7.99 (s, 1H), 8.31 (s, 2H), 9.55 (s, 1H), 12.90 (s, 1H) |
| 114 | 4-(difluoromethoxy)phenyl | pyridin-2-ylamino | butylene | 1.86 | 373.2 | 400 MHz, DMSO-d6: δ ppm 1.79-1.83 (m, 2H), 2.50-2.54 (m, 2H), 3.30 (t, J = 20.00 Hz, 2H), 6.54 (t, J = 9.20 Hz, 1H), 6.92-7.29 (m, 4H), 7.76-7.78 (m, 2H), 8.26 (d, J = 4.40 Hz, 2H), 8.38 (s, 2H), 9.57 (s, 1H) |

-continued
| Ex. | R₁ | R₂ | Linker | LCMS RT, min | LCMS Ion [M + H]⁺ | ¹H NMR |
|---|---|---|---|---|---|---|
| 115 | 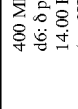 | 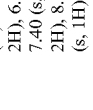 |  | 1.81 | 413.2 | 400 MHz, DMSO-d6: δ ppm 1.82 (t, J = 14.00 Hz, 2H), 2.48-2.52 (m, 2H), 3.37-3.41 (m, 2H), 6.92-7.29 (m, 5H), 7.40 (s, 1H), 7.76-7.78 (m, 2H), 8.01 (s, 1H), 8.37 (s, 1H), 9.58 (s, 1H) |
| 116 |  |  | 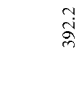 | 2.11 | 392.2 | 400 MHz, DMSO-d6: δ ppm 1.52 (t, J = 10.80 Hz, 2H), 2.11-2.16 (m, 1H), 2.33-2.39 (m, 2H), 6.92-7.29 (m, 4H), 7.47 (d, J = 8.40 Hz, 1H), 7.57 (s, 1H), 7.76-7.79 (m, 2H), 7.99 (d, J = 0.80 Hz, 1H), 8.40 (s, 2H), 9.61 (s, 1H), 12.97 (bs, 1H) |
| 117 | 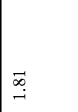 |  |  | 1.93 | 394.2 | 400 MHz, DMSO-d6: δ ppm 1.60-1.65 (m, 2H), 2.31-2.35 (m, 1H), 2.68-2.70 (m, 1H), 6.81-7.37 (m, 6H), 7.78-7.80 (m, 2H), 8.24 (s, 1H), 8.45 (s, 2H), 9.65 (s, 1H), 13.09 (bs, 1H) |
| 118 |  |  |  | 2.02 | 414 | 400 MHz, DMSO-d6: δ ppm 2.86 (t, J = 24.80 Hz, 2H), 3.01 (t, J = 15.60 Hz, 2H), 6.91-7.29 (m, 3H), 7.35-7.37 (m, 1H), 7.49 (t, J = 18.40 Hz, 2H), 7.74-7.77 (m, 2H), 8.33 (s, 2H), 9.56 (s, 1H), 13.19 (s, 1H) |

-continued

| Ex. | R₁ | R₂ | Linker | LCMS RT, min | LCMS Ion [M + H]⁺ | ¹H NMR |
|---|---|---|---|---|---|---|
| 119 | 4-(OCHF₂)-3-Cl-phenyl | quinolin-2(1H)-one-6-yl | -CH₂CH₂CH(CH₃)- | 2.1 | 441.0 | 400 MHz, DMSO-d6: δ ppm 2.83 (t, J = 14.80 Hz, 2H), 2.93 (t, J = 14.80 Hz, 2H), 6.46-6.49 (m, 1H), 6.95-7.39 (m, 4H), 7.48 (s, 1H), 7.65-7.68 (m, 1H), 7.84 (d, J = 9.60 Hz, 1H), 8.09 (d, J = 2.40 Hz, 1H), 8.37 (s, 2H), 9.78 (s, 1H), 11.68 (s, 1H) |
| 120 | 3-F-4-Me-phenyl | 1H-indazol-5-yl | -CH₂CH₂CH(CH₃)- | 2.03 | 346.2 | 400 MHz, DMSO-d6: δ ppm 2.16 (s, 3H), 2.84 (t, J = 15.20 Hz, 2H), 2.98 (t, J = 15.20 Hz, 2H), 7.13 (t, J = 17.60 Hz, 1H), 7.23 (d, J = 1.60 Hz, 1H), 7.25 (d, J = 1.20 Hz, 1H), 7.34-7.36 (m, 1H), 7.45-7.54 (m, 1H), 7.70-7.73 (m, 1H), 7.98 (s, 1H), 8.32 (s, 1H), 9.60 (s, 1H), 12.95 (s, 1H) |
| 121 | 3-F-4-Me-phenyl | quinolin-2(1H)-one-6-yl | -CH₂CH₂CH(CH₃)- | 1.91 | 373.2 | 400 MHz, DMSO-d6: δ ppm 2.16 (s, 3H), 2.83 (t, J = 8.00 Hz, 2H), 2.91 (t, J = 8.00 Hz, 2H), 6.46-6.49 (m, 1H), 7.09-7.16 (m, 1H), 7.23 (t, J = 11.60 Hz, 1H), 7.34-7.39 (m, 2H), 7.48 (s, 1H), 7.70 (d, J = 2.40 Hz, 1H), 7.73-7.85 (m, 1H), 8.33 (s, 2H), 9.61 (s, 1H), 11.68 (s, 1H) |

| Ex. | R₁ | R₂ | Linker | LCMS RT, min | LCMS Ion [M + H]⁺ | ¹H NMR |
|---|---|---|---|---|---|---|
| 122 | 4-(difluoromethoxy)phenyl | quinolin-2(1H)-one-6-yl | -CH₂CH(CH₃)CH₂- | 1.86 | 423.2 | 400 MHz, DMSO-d6: δ ppm 1.26 (d, J = 6.80 Hz, 3H), 2.78 (d, J = 7.60 Hz, 2H), 3.03-3.09 (m, 1H), 6.45-6.48 (m, 1H), 6.90-7.28 (m, 4H), 7.38-7.41 (m, 1H), 7.47 (d, J = 1.60 Hz, 1H), 7.70-7.74 (m, 2H), 7.84 (d, J = 9.60 Hz, 1H), 8.17 (s, 2H), 9.51 (s, 1H), 11.65 (s, 1H) |
| 123 | 4-(difluoromethoxy)phenyl | benzo[d]oxazol-2(3H)-one-5-yl | -CH₂CH₂CH₂- | 1.96 | 397.2 | 400 MHz, DMSO-d6: δ ppm 2.79 (t, J = 15.60 Hz, 2H), 2.89 (t, J = 14.80 Hz, 2H), 6.91-7.29 (m, 6H), 7.74-7.77 (m, 2H), 8.31 (d, J = 7.20 Hz, 2H), 9.56 (s, 1H), 11.50 (bs, 1H) |
| 124 | 4-(difluoromethoxy)phenyl | 3-cyano-1H-indazol-5-yl | -CH₂CH₂CH₂- | 1.96 | 407.2 | 400 MHz, DMSO-d6: δ ppm 2.86 (t, J = 15.60 Hz, 2H), 3.05 (t, J = 15.60 Hz, 2H), 6.91-7.29 (m, 3H), 7.42-7.45 (m, 1H), 7.68-7.76 (m, 4H), 8.34 (d, J = Hz, 2H), 9.56 (s, 1H), 14.14 (bs, 1H) |

| Ex. | R₁ | R₂ | Linker | LCMS RT, min | LCMS Ion [M + H]⁺ | ¹H NMR |
|---|---|---|---|---|---|---|
| 125 | 3-fluoro-4-ethylphenyl | 1H-indazol-5-yl | -CH₂CH₂C(CH₃)₂- | 2.01 | 362.2 | 400 MHz, DMSO-d6: δ ppm 1.15 (t, J = 15.20 Hz, 3H), 2.52-2.58 (m, 2H), 2.84 (t, J = 15.20 Hz, 2H), 2.98 (t, J = 14.80 Hz, 2H), 7.15 (t, J = 17.60 Hz, 1H), 7.23-7.26 (m, 1H), 7.36-7.38 (m, 1H), 7.47 (d, J = 8.80 Hz, 1H), 7.54 (s, 1H), 7.68-7.72 (m, 1H), 7.80 (s, 1H), 8.32 (s, 2H), 9.60 (s, 1H), 12.95 (bs, 1H) |
| 126 | 3-fluoro-4-ethylphenyl | quinolin-2(1H)-on-6-yl | -CH₂CH₂C(CH₃)₂- | 1.94 | 389.2 | 400 MHz, DMSO-d6: δ ppm 1.15 (t, J = 15.20 Hz, 3H), 2.50-2.52 (m, 2H), 2.83 (t, J = 8.00 Hz, 2H), 2.92 (t, J = 8.00 Hz, 2H), 6.46-6.49 (m, 1H), 7.13-7.25 (m, 2H), 7.36-7.39 (m, 2H), 7.48 (s, 1H), 7.69 (d, J = 2.40 Hz, 1H), 7.72-7.85 (m, 1H), 8.33 (s, 2H), 9.61 (s, 1H), 11.67 (bs, 1H) |
| 127 | 4-ethylphenyl | 1H-indazol-5-yl | -CH₂CH₂C(CH₃)₂- | 2.05 | 344.2 | 400 MHz, DMSO-d6: δ ppm 1.16 (t, J = 15.20 Hz, 3H), 2.53 (q, J = 13.60 Hz, 2H), 2.82 (t, J = 15.60 Hz, 2H), 2.97 (t, J = 14.80 Hz, 2H), 7.09 (d, J = 8.40 Hz, 2H), 7.23-7.25 (m, 1H), 7.46 (d, J = 8.40 Hz, 1H), 7.54 (s, 1H), 7.60-7.62 (m, 2H), 7.98 (s, 1H), 8.26 (s, 2H), 9.34 (s, 1H), 12.94 (s, 1H) |

| Ex. | R₁ | R₂ | Linker | LCMS RT, min | LCMS Ion [M + H]⁺ | ¹H NMR |
|---|---|---|---|---|---|---|
| 128 | 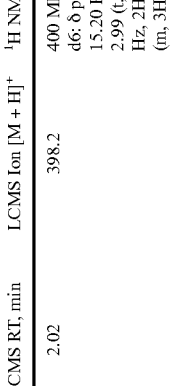 |  |  | 2.02 | 398.2 | 400 MHz, DMSO-d6: δ ppm 2.86 (t, J = 15.20 Hz, 2H), 2.99 (t, J = 14.80 Hz, 2H), 6.93-7.29 (m, 3H), 7.47 (d, J = 8.80 Hz, 2H), 7.54 (s, 1H), 7.93 (dd, J = 16.40, Hz, 1H), 7.98 (s, 1H), 8.35 (s, 2H), 9.80 (s, 1H), 12.95 (s, 1H) |
| 129 | 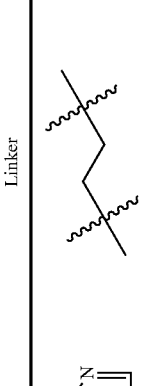 |  | 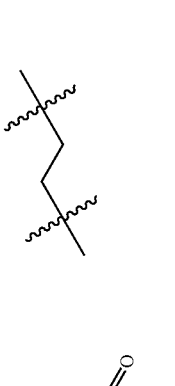 | 1.94 | 425.2 | 400 MHz, DMSO-d6: δ ppm 2.84 (t, J = 14.40 Hz, 2H), 2.93 (t, J = 14.40 Hz, 2H), 6.47 (d, J = 9.60 Hz, 1H), 7.11-7.30 (m, 3H), 7.37-7.39 (m, 1H), 7.45-7.48 (m, 2H), 7.84 (d, J = 9.60 Hz, 1H), 7.94 (dd, J = 16.40, Hz, 1H), 8.37 (s, 2H), 9.81 (s, 1H), 11.68 (s, 1H) |
| 130 | 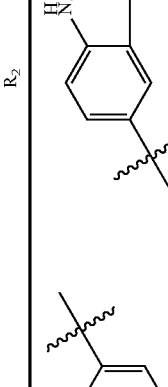 | 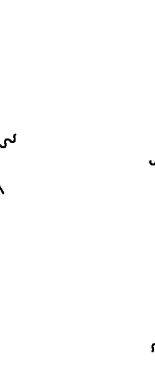 | 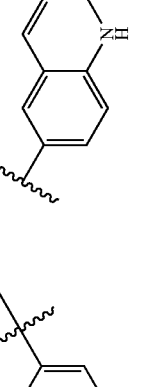 | 1.96 | 396.2 | 400 MHz, DMSO-d6: δ ppm 1.25 (d, J = 6.80 Hz, 3H), 2.96 (d, J = 6.40 Hz, 2H), 2.99-3.03 (m, 1H), 6.91-7.28 (m, 4H), 7.41-7.47 (m, 2H), 7.74 (dd, J = 9.20, Hz, 2H), 7.96 (s, 1H), 8.32 (s, 2H), 9.54 (s, 1H), 12.94 (s, 1H) |

| Ex. | R₁ | R₂ | Linker | LCMS RT, min | LCMS Ion [M + H]⁺ | ¹H NMR |
|---|---|---|---|---|---|---|
| 131 | 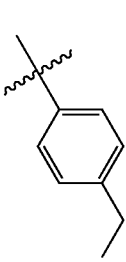 | 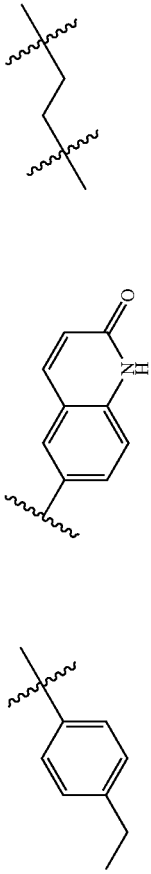 |  | 1.9 | 371.2 | 400 MHz, DMSO-d6: δ ppm 1.16 (t, J = 15.20 Hz, 3H), 2.55 (q, J = 15.20 Hz, 2H), 2.80 (t, J = 15.20 Hz, 2H), 2.91 (t, J = 14.80 Hz, 2H), 6.48 (d, J = 20.00 Hz, 1H), 7.10 (d, J = 8.40 Hz, 2H), 7.24 (d, J = 8.40 Hz, 2H), 7.38 (dd, J = 10.40 Hz, 1H), 7.48 (s, 1H), 7.61 (d, J = 8.40 Hz, 2H), 7.84 (d, J = 9.60 Hz, 1H), 8.28 (s, 2H), 9.36 (s, 1H), 11.68 (s, 1H) |
| 132 |  |  |  | 1.84 | 387.2 | 400 MHz, DMSO-d6: δ ppm 1.71 (s, 3H), 2.79 (t, J = 14.80 Hz, 2H), 2.90 (t, J = 14.80 Hz, 2H), 3.74 (s, 3H), 6.47 (d, J = 9.60 Hz, 1H), 6.84 (d, J = 8.80 Hz, 1H), 7.24 (d, J = 8.40 Hz, 1H), 7.36-7.39 (m, 2H), 7.48-7.50 (m, 2H), 7.84 (d, J = 9.60 Hz, 1H), 8.24 (s, 2H), 9.15 (s, 1H),11.68 (bs, 1H) |
| 133 | 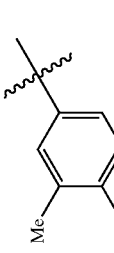 | 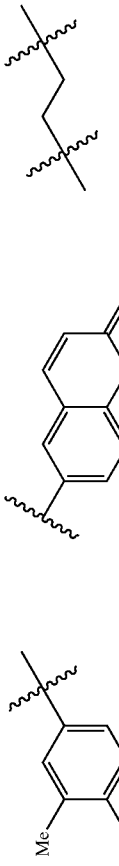 |  | 1.89 | 396 | 400 MHz, DMSO-d6: δ ppm 2.85 (t, J = 8.00 Hz, 2H), 2.97 (t, J = 8.00 Hz, 2H), 7.23-7.31 (m, 2H), 7.39-7.41 (m, 1H), 7.46 (d, J = 8.40 Hz, 1H), 7.54 (s, 1H), 7.94-7.98 (m, 2H), 8.33 (s, 2H), 9.71 (s, 1H), 12.95 (bs, 1H) |

-continued
| Ex. | R₁ | R₂ | Linker | LCMS RT, min | LCMS Ion [M + H]⁺ | ¹H NMR |
|---|---|---|---|---|---|---|
| 134 | 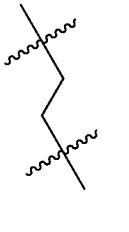 | 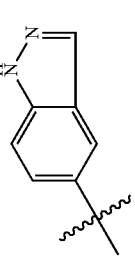 |  | 2.04 | 378.2 | 400 MHz, DMSO-d6: δ ppm 1.15 (t, J = 15.20 Hz, 3H), 2.64 (q, J = 12.00 Hz, 2H), 2.85 (t, J = 8.40 Hz, 2H), 2.97 (t, J = 8.00 Hz, 2H), 7.21-7.26 (m, 2H), 7.47 (d, J = 8.40 Hz, 1H), 7.54-7.57 (m, 2H), 7.93 (d, J = 2.40 Hz, 1H), 7.98 (s, 1H), 8.33 (s, 2H), 9.61 (s, 1H), 12.96 (s, 1H) |
| 135 | 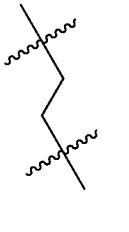 | 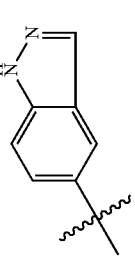 |  | 1.97 | 405.2 | 400 MHz, DMSO-d6: δ ppm 1.15 (t, J = 14.80 Hz, 3H), 2.63 (q, J = 22.40 Hz, 2H), 2.82 (t, J = 14.80 Hz, 2H), 2.92 (t, J = 15.20 Hz, 2H), 6.47 (dd, J = 11.20, Hz, 1H), 7.21-7.25 (m, 2H), 7.38 (dd, J = 10.40, Hz, 1H), 7.48 (d, J = 1.60 Hz, 1H), 7.56 (dd, J = 10.80, Hz, 1H), 7.84 (d, J = 9.60 Hz, 1H), 7.94 (d, J = 2.40 Hz, 1H), 8.34 (s, 2H), 9.62 (s, 1H), 11.70 (s, 1H) |
| 136 | 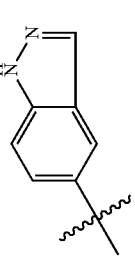 |  |  | 1.93 | 411.2 | 400 MHz, DMSO-d6: δ ppm 1.22 (d, J = 7.20 Hz, 3H), 2.85-2.87 (m, 1H), 2.96-2.98 (m, 2H), 6.83-7.29 (m, 6H), 7.75 (d, J = 9.20 Hz, 2H), 8.32 (s, 2H), 9.57 (s, 1H) |

| Ex. | R₁ | R₂ | Linker | LCMS RT, min | LCMS Ion [M + H]⁺ | ¹H NMR |
|---|---|---|---|---|---|---|
| 137 | 4-(difluoromethoxy)phenyl | quinolin-2(1H)-one-6-yl | isobutylene linker | 1.97 | 423.2 | 400 MHz, DMSO-d6: δ ppm 1.25 (d, J = 6.80 Hz, 3H), 2.91 (d, J = 7.60 Hz, 2H), 2.99-3.03 (m, 1H), 6.45 (d, J = 9.60 Hz, 1H), 6.91-7.10 (m, 3H), 7.19 (d, J = 8.40 Hz, 1H), 7.27-7.30 (m, 1H), 7.40 (s, 1H), 7.65 (dd, J = −69.20, Hz, 2H), 7.81 (d, J = 9.60 Hz, 1H), 8.32 (s, 2H), 9.55 (s, 1H), 11.65 (s, 1H) |
| 138 | 4-(difluoromethoxy)phenyl | 4,4-dimethyl-2-oxo-benzoxazine | propyl linker | 2.2 | 441.2 | 400 MHz, DMSO-d6: δ ppm 1.56 (s, 6H), 2.77-2.82 (m, 4H), 6.80 (d, J = 8.00 Hz, 1H), 6.91-7.29 (m, 5H), 7.75 (d, J = 8.80 Hz, 2H), 8.27 (s, 2H), 9.56 (s, 1H), 10.10 (s, 1H) |
| 139 | 4-(difluoromethoxy)phenyl | 2-oxo-benzoxazine | propyl linker | 2.01 | 413.2 | 400 MHz, DMSO-d6: δ ppm 2.76-2.82 (m, 4H), 5.25 (s, 2H), 6.80 (d, J = 7.60 Hz, 1H), 6.91-7.29 (m, 5H), 7.76 (d, J = 9.20 Hz, 2H), 8.30 (s, 2H), 9.56 (s, 1H), 10.08 (s, 1H) |
| 140 | 3-chloro-4-(difluoromethoxy)phenyl | 4,4-dimethyl-2-oxo-benzoxazine | propyl linker | 2.2 | 475.0 | 400 MHz, DMSO-d6: δ ppm 1.56 (s, 6H), 2.78-2.83 (m, 4H), 6.79 (d, J = 8.00 Hz, 1H), 7.32 (m, 4H), 7.65-7.68 (m, 1H), 8.08 (d, J = 2.80 Hz, 1H), 8.32 (s, 2H), 9.78 (s, 1H), 10.10 (s, 1H) |

| Ex. | R₁ | R₂ | Linker | LCMS RT, min | LCMS Ion [M + H]⁺ | ¹H NMR |
|---|---|---|---|---|---|---|
| 141 | 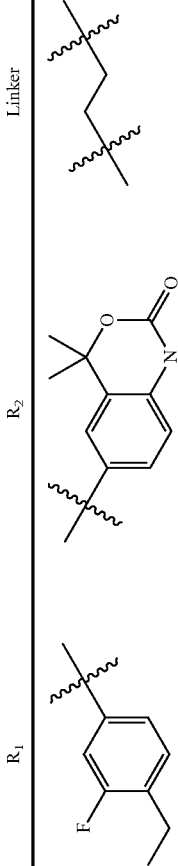 | 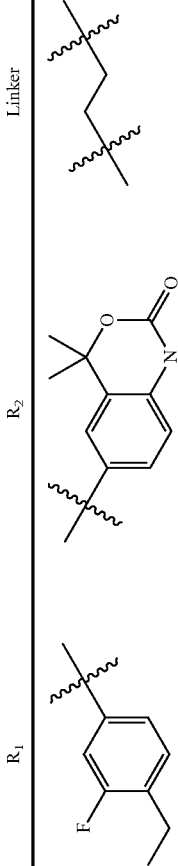 | 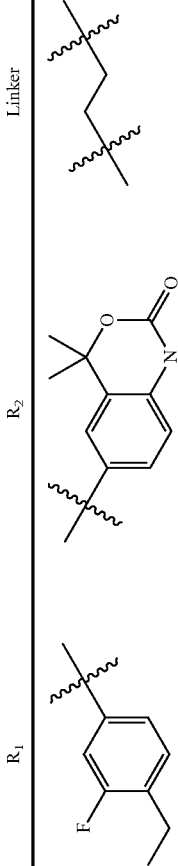 | 2.27 | 421.2 | 400 MHz, DMSO-d6: δ ppm 1.15 (t, J = 14.80 Hz, 3H), 1.56 (s, 6H), 2.50-2.58 (m, 2H), 2.77-2.82 (m, 4H), 6.79 (d, J = 8.00 Hz, 1H), 7.06-7.18 (m, 3H), 7.36-7.38 (m, 1H), 7.68-7.72 (m, 1H), 8.29 (s, 2H), 9.61 (s, 1H), 10.10 (s, 1H) |
| 142 | 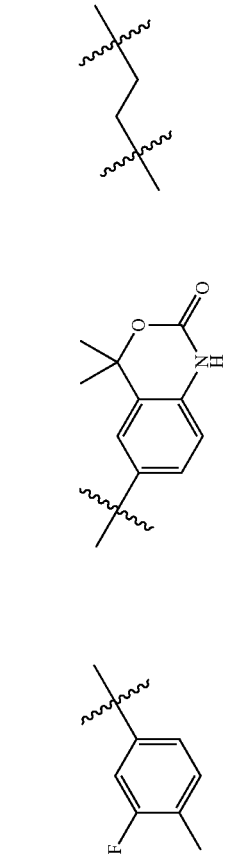 | 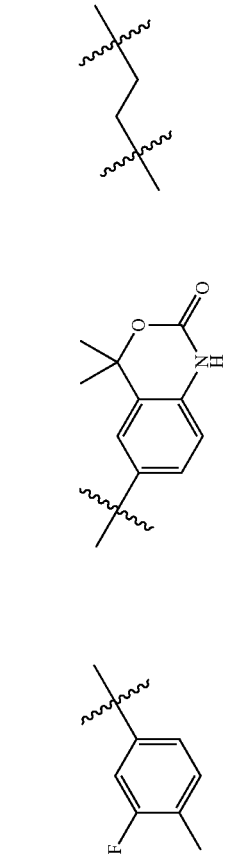 | 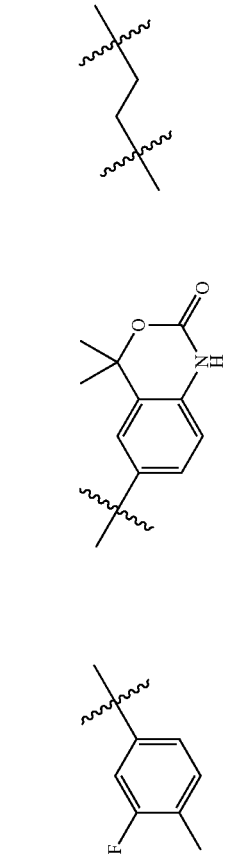 | 2.2 | 407.2 | 400 MHz, DMSO-d6: δ ppm 1.56 (s, 6H), 2.16 (s, 3H), 2.77-2.82 (m, 4H), 6.79 (d, J = 7.60 Hz, 1H), 7.06-7.16 (m, 3H), 7.35 (d, J = 8.00 Hz, 1H), 7.72 (d, J = 13.20 Hz, 1H), 8.29 (s, 2H), 9.61 (s, 1H), 10.10 (s, 1H) |
| 143 |  |  |  | 2.13 | 447 | 400 MHz, DMSO-d6: δ ppm 2.77-2.83 (m, 4H), 5.24 (s, 2H), 6.79 (d, J = 7.60 Hz, 2H), 6.95-7.13 (m, 4H), 7.67 (d, J = 9.20 Hz, 1H), 8.09 (s, 1H), 8.36 (s, 2H), 9.78 (s, 1H), 10.07 (s, 1H) |

| Ex. | R₁ | R₂ | Linker | LCMS RT, min | LCMS Ion [M + H]⁺ | ¹H NMR |
|---|---|---|---|---|---|---|
| 144 | (3-fluoro-4-ethylphenyl) | 4H-benzo[d][1,3]oxazin-2(1H)-one | | 1.94 | 393.2 | ¹H NMR (400 MHz, DMSO-d6) δ ppm 1.15 (s, 3H) 2.54-2.56 (m, 2H) 2.72-2.86 (m, 4H) 5.24 (s, 2H) 6.25-6.32 (m, 3H) 6.49-6.64 (m, 3H) 6.77-6.82 (m, 1H) 7.12 (tdd, J = 12.30, 12.30, 4.27, 2.26 Hz, 3H) 7.29-7.44 (m, 1H) 7.66-7.79 (m, 1H) 8.33 (s, 2H) 9.52-9.70 (m, 1H) 9.94-10.22 (m, 1H) |
| 145 | (3-methyl-4-difluoromethoxyphenyl) | 4H-benzo[d][1,3]oxazin-2(1H)-one | | 2.1 | 427.2 | ¹H NMR (400 MHz, DMSO-d6) δ ppm 2.20 (s, 3H) 2.64-2.92 (m, 4H) 5.24 (s, 2H) 6.73-6.80 (m, 1H) 7.03-7.22 (m, 4H) 7.56-7.66 (m, 2H) 8.25-8.33 (m, 2H) 9.44-9.52 (m, 1H) 10.07 (br. s., 1H) |
| 146 | (3-methyl-4-difluoromethoxyphenyl) | 4H-benzo[d][1,3]oxazin-2(1H)-one | | 2.1 | 431.2 | ¹H NMR (400 MHz, DMSO-d6) δ ppm 2.71-2.87 (m, 4H) 5.24 (s, 2H) 6.79 (d, J = 7.78 Hz, 1H) 6.92-7.33 (m, 4H) 7.48 (s, 1H) 7.88-7.98 (m, 1H) 8.36 (s, 2H) 9.81 (s, 1H) 10.07 (s, 1H) |
| 147 | (3-methyl-4-difluoromethoxyphenyl) | 4,4-dimethyl-4H-benzo[d][1,3]oxazin-2(1H)-one | | 2.16 | 455.2 | ¹H NMR (400 MHz, DMSO-d6) δ ppm 1.56 (s, 6H) 2.20 (s, 3H) 2.78 (dd, J = 18.20, 6.90 Hz, 4H) 6.78 (s, 1H) 6.86-7.25 (m, 4H) 7.52-7.65 (m, 2H) 8.26 (s, 2H) 9.47 (s, 1H) 10.10 (s, 1H) |

| Ex. | R₁ | R₂ | Linker | LCMS RT, min | LCMS Ion [M + H]⁺ | ¹H NMR |
|---|---|---|---|---|---|---|
| 148 | 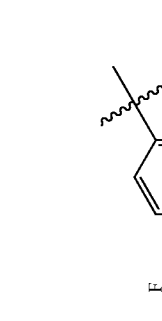 | 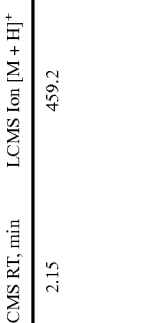 |  | 2.15 | 459.2 | 1H NMR (400 MHz, DMSO-d6) δ ppm 1.55 (s, 6H) 2.79 (dd, J=11.54, 4.77 Hz, 4H) 6.78 (d, J = 8.03 Hz, 1H) 6.89-7.30 (m, 4H) 7.45 (d, J = 9.03 Hz, 1H) 7.92 (dd, J = 13.80, 2.51 Hz, 1H) 8.31 (s, 2H) 9.80 (s, 1H) 10.09 (s, 1H) |
| 149 | 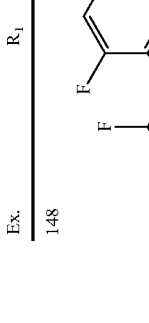 |  |  | 2.42 | 379.0 | 1H NMR (400 MHz, DMSO-d6) δ ppm 2.161 (s, 3H) 2.63-2.88 (m, 4H) 2.71-2.88 (m, 3H) 5.242 (s, 2H) 6.75-6.83 (m, 1H) 7.06-7.17 (m, 2H) 7.16-7.27 (m, 1H) 7.33-7.38 (m, 1H) 7.69-7.75 (m, 1H) 8.31-8.326 (s, 2H) 9.613 (s, 1H) 10.071 (s, 1H) |
| 150 | 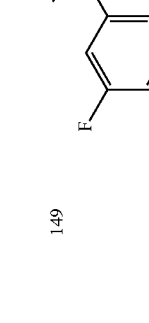 |  | 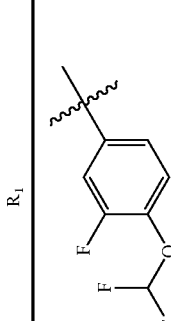 | 2.14 | 358.1 | 1H NMR (300 MHz, DMSO-d6) δ ppm 2.73 (s, 4H) 6.66 (d, J = 8.40 Hz, 2H) 6.83-7.35 (m, 5H) 7.71-7.79 (m, 2H) 8.26 (s, 2H) 9.15 (br. s., 1H) 9.55 (s, 1H) |
| 151 | 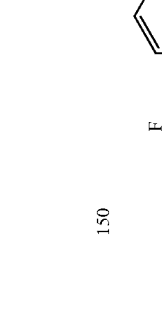 | 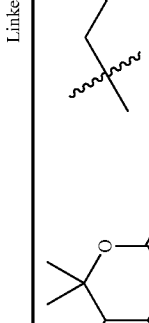 | 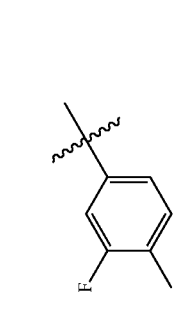 | 2.13 | 363.2 | 300 MHz, DMSO-d6: δ ppm 1.14 (t, J = 10.40 Hz, 3H), 2.52 (q, J = 2.40 Hz, 2H), 2.86 (d, J = 10.80 Hz, 2H), 3.01 (d, J = 10.40 Hz, 2H), 7.13 (d, J = 11.20 Hz, 1H), 7.35 (d, J = 2.80 Hz, 1H), 7.67 (d, J = 2.80 Hz, 1H), 8.03 (d, J = 3.60 Hz, 2H), 8.34 (s, 2H), 8.39 (d, J = 2.80 Hz, 1H), 9.63 (s, 1H) |

| Ex. | R₁ | R₂ | Linker | LCMS RT, min | LCMS Ion [M + H]⁺ | ¹H NMR |
|---|---|---|---|---|---|---|
| 152 | 4-(difluoromethoxy)-3-fluorophenyl | 1H-pyrazolo[3,4-b]pyridin-5-yl | propylene (branched) | 1.91 | 401.0 | 1H NMR (300 MHz, DMSO-d6) δ ppm 2.82-2.90 (m, 2H) 2.98-3.06 (m, 2H) 6.84-7.37 (m, 2H) 7.46 (dt, J = 9.06, 1.27 Hz, 1H) 7.93 (dd, J = 13.88, 2.55 Hz, 1H) 8.01-8.10 (m, 2H) 8.35-8.42 (m, 3H) 9.82 (s, 1H) 13.53 (br. s., 1H) |
| 153 | 4-(difluoromethoxy)-3-methylphenyl | 1H-pyrazolo[3,4-b]pyridin-5-yl | propylene (branched) | 1.95 | 397.2 | 1H NMR (300 MHz, DMSO-d6) δ ppm 2.20 (s, 3H) 2.80-2.89 (m, 2H) 2.98-3.06 (m, 2H) 6.77-7.29 (m, 2H) 7.55-7.63 (m, 2H) 8.00-8.08 (m, 2H) 8.31 (s, 2H) 8.39 (d, J = 2.08 Hz, 1H) 9.49 (s, 1H) 13.52 (s, 1H) |
| 154 | 4-(difluoromethoxy)phenyl | 1H-pyrazolo[3,4-b]pyridin-5-yl | propylene (branched) | 1.8 | 383.1 | 1H NMR (300 MHz, DMSO-d6) δ ppm 2.80-2.88 (m, 2H) 2.96-3.06 (m, 2H) 6.82-7.35 (m, 3H) 7.71-7.78 (m, 2H) 8.05 (d, J = 10.39 Hz, 2H) 8.31 (s, 2H) 8.39 (d, J = 2.08 Hz, 1H) 9.57 (s, 1H) 13.52 (br. s., 1H) |
| 155 | 4-(difluoromethoxy)phenyl | 2-oxo-1,2-dihydro-1,8-naphthyridin-6-yl | propylene (branched) | 1.72 | 410 | 1H NMR (400 MHz, DMSO-d6) δ ppm 2.85 (d, J = 8.41 Hz, 2H) 2.95 (d, J = 8.03 Hz, 2H) 6.48-6.60 (m, 1H) 6.85-7.32 (m, 3H) 7.74-7.76 (m, 2H) 7.86-7.89 (m, 1H) 7.97-7.98 (m, 1H) 8.32 (s, 2H), 8.36-8.37 (m, 1H), 9.58 (s, 1H) 12.06 (s, 1H) |

Example 156

6-(2-(1H-indazol-5-yl)ethyl)-N-(4-(difluoromethoxy)phenyl)pyridazin-3-amine

N-(4-(difluoromethoxy)phenyl)-6-vinylpyridazin-3-amine

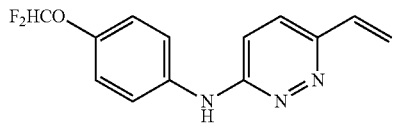 [SMILES: C=Cc1ccc(Nc2ccc(OC(F)F)cc2)nn1]

To a solution of 6-chloro-N-(4-(difluoromethoxy)phenyl)pyridazin-3-amine (0.2 g, 0.736 mmol) in dioxane and water mixture were added vinylboronic acid pinacol ester (0.146 mL, 1.104 mmol), and $K_2CO_3$ (0.305 g, 2.209 mmol). The mixture was flushed for 15 min with nitrogen. $PdCl_2$ (dppf)-$CH_2Cl_2$ adduct (0.060 g, 0.074 mmol) was then added and the reaction mixture heated at 80° C. for 18 h. The reaction mixture was filtered through a pad of celite, washed with ethyl acetate and purified by flash chromatography on silica gel using ethyl acetate in hexane to give N-(4-(difluoromethoxy)phenyl)-6-vinylpyridazin-3-amine as a white solid (0.12 g, 59%). $^1$HNMR 400 MHz, DMSO-d6: δ ppm 5.47 (d, J=1.20 Hz, 1H), 6.06 (dd, J=0.80, 23.80 Hz, 1H), 6.84-7.38 (m, 5H), 7.75-7.82 (m, 3H), 9.42 (s, 1H).

(E)-N-(4-(difluoromethoxy)phenyl)-6-(2-(1-(tetrahydro-2H-pyran-2-yl)-1H-indazol-5-yl)vinyl)pyridazin-3-amine

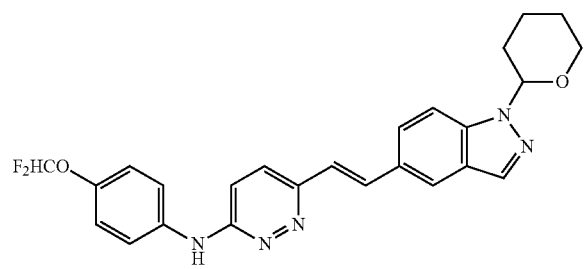 [SMILES: FC(F)Oc1ccc(Nc2ccc(/C=C/c3ccc4c(cnn4C4CCCCO4)c3)nn2)cc1]

To a solution of 5-iodo-1-(tetrahydro-2H-pyran-2-yl)-1H-indazole (0.1 g, 0.305 mmol) in ACN (5 mL) were added N-(4-(difluoromethoxy)phenyl)-6-vinylpyridazin-3-amine (0.080 g, 0.305 mmol), tri-o-tolylphosphine (0.037 g, 0.122 mmol), and triethylamine (0.127 mL, 0.914 mmol). The reaction mixture was purged with nitrogen for 5 min. Tris(dibenzylideneacetone)dipalladium(0) chloroform adduct (0.032 g, 0.030 mmol) was added and the reaction mixture was heated at 90° C. for 18 h. The reaction mixture was filtered through a pad of celite and rinsed with ethyl acetate. The organic layer was concentrated and purified by flash chromatography on silica gel using ethyl acetate/hexane to give (E)-N-(4-(difluoromethoxy)phenyl)-6-(2-(1-(tetrahydro-2H-pyran-2-yl)-1H-indazol-5-yl)vinyl)pyridazin-3-amine as a pale yellow solid (0.13 g, 87%). LCMS (ES-API), m/z 464.6 (M+H).

N-(4-(difluoromethoxy)phenyl)-6-(2-(1-(tetrahydro-2H-pyran-2-yl)-1H-indazol-5-yl)ethyl)pyridazin-3-amine

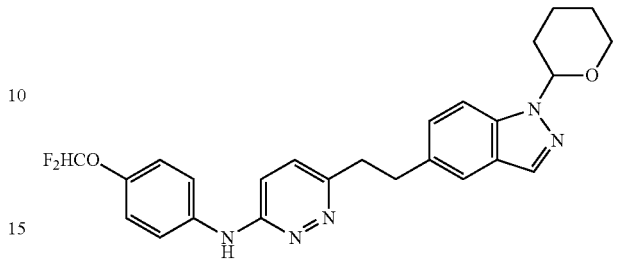

To a solution of (E)-N-(4-(difluoromethoxy)phenyl)-6-(2-(1-(tetrahydro-2H-pyran-2-yl)-1H-indazol-5-yl)vinyl)pyridazin-3-amine (0.14 g, 0.302 mmol) in ethyl acetate (5 mL) was added Pd—C (0.064 g, 0.604 mmol and the reaction mixture was stirred at room temperature under $H_2$ for 3 h. The reaction mixture was filtered through pad of celite, washed with ethyl acetate, and the filtrate was concentrated to give N-(4-(difluoromethoxy)phenyl)-6-(2-(1-(tetrahydro-2H-pyran-2-yl)-1H-indazol-5-yl)ethyl)pyridazin-3-amine as a yellow solid (0.13 g, 80%). LCMS (ES-API), m/z 466.6 (M+H).

6-(2-(1H-indazol-5-yl)ethyl)-N-(4-(difluoromethoxy)phenyl)pyridazin-3-amine

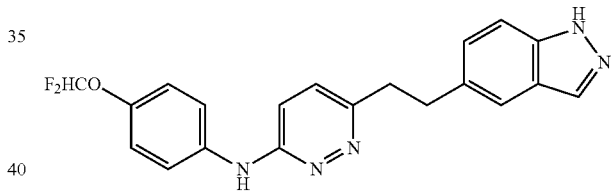

To a stirred solution of N-(4-(difluoromethoxy)phenyl)-6-(2-(1-(tetrahydro-2H-pyran-2-yl)-1H-indazol-5-yl)ethyl)pyridazin-3-amine (0.12 g, 0.258 mmol) in DCM (10 mL) was added TFA (1 mL, 12.98 mmol) and the reaction mixture was stirred at room temperature for 3 h. The reaction mixture was concentrated and washed with diethyl ether. The crude product was purified by preparative LCMS on a Waters Xbridge C18 column (19×150 mm, 5 μm) using 0-100% mobile phase B (95:5 Methanol:water with 10 mM $NH_4OAc$) in mobile phase A (5:95 Methanol:water with 10 mM $NH_4OAc$) to give 6-(2-(1H-indazol-5-yl)ethyl)-N-(4-(difluoromethoxy)phenyl)pyridazin-3-amine. $^1$H-NMR (300 MHz, DMSO-d6) δ ppm 3.07-3.14 (m, 4H) 6.28 (s, 1H) 7.00-7.37 (m, 6H) 7.46 (s, 1H) 7.56 (s, 1H) 7.78 (s, 3H) 7.97 (s, 1H) 9.19 (s, 1H) 12.93 (br. s., 1H).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

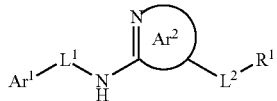

where:
R¹ is selected from the group consisting of

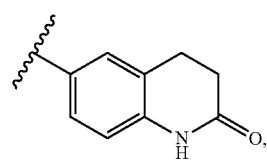 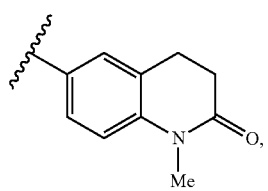
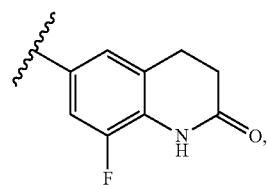 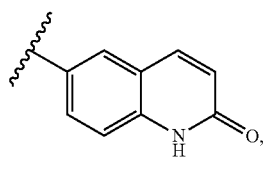
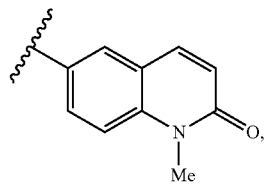 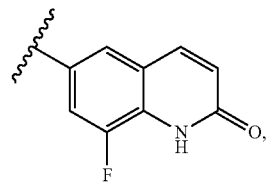
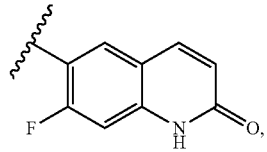 
 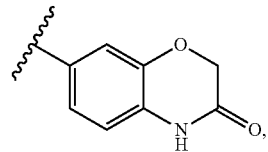
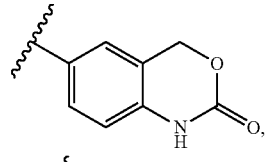 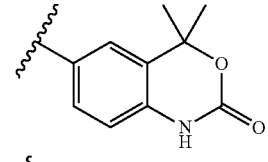
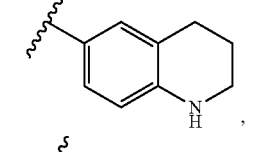 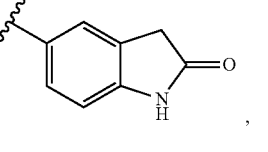
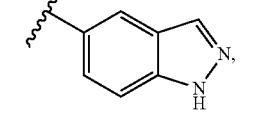 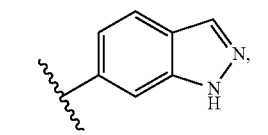

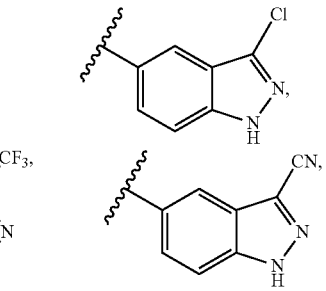
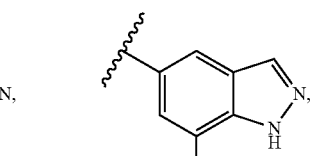
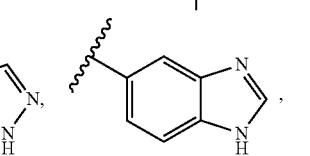
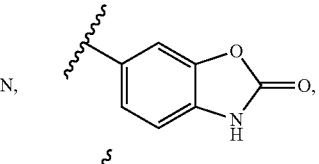
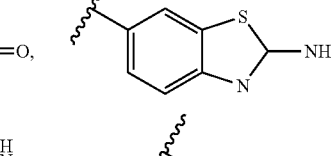
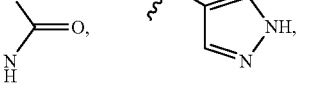
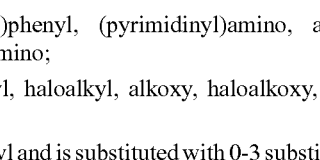

Ar³, ((thiazolyl)amino)phenyl, (pyrimidinyl)amino, and (pyrazolopyrimidinyl)amino;

R² is hydrogen, alkyl, haloalkyl, alkoxy, haloalkoxy, or alkylSO₂;

Ar¹ phenyl or pyridinyl and is substituted with 0-3 substituents selected from halo, alkyl, haloalkyl, alkoxy, haloalkoxy, dialkylamino, and alkylSO₂;

Ar² is

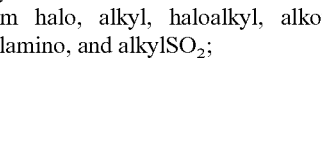
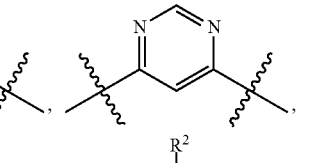
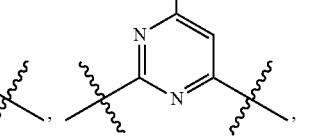

151
-continued

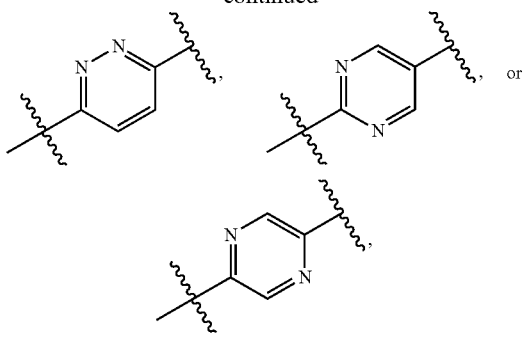

and where Ar² is substituted with 0-1 substituents selected from the group consisting of hydroxy, cyano, halo, alkyl, alkoxy, and haloalkoxy;

Ar³ is phenyl, pyridinyl, pyrazinyl, pyrimidinyl, or pyridazinyl, and is substituted with 1 substituent selected from hydroxy, NH₂—, NHCO₂alkyl, or NHSO₂alkyl, and is also substituted with 0-3 substituents selected from halo, alkyl, and haloalkyl;

L¹ is a direct bond, —CH₂—, or —CH₂CH₂—; and
L² is —O—, —CH₂O—, —OCH₂—, —CH₂—, —CH₂CH₂—, —CH(CH₃)CH₂—, —CH₂CH(CH₃)—, —CH₂CH₂CH₂—, or cyclopropdiyl;

or a pharmaceutically acceptable salt thereof.

2. A compound of claim 1 where
R¹ is selected from the group consisting of

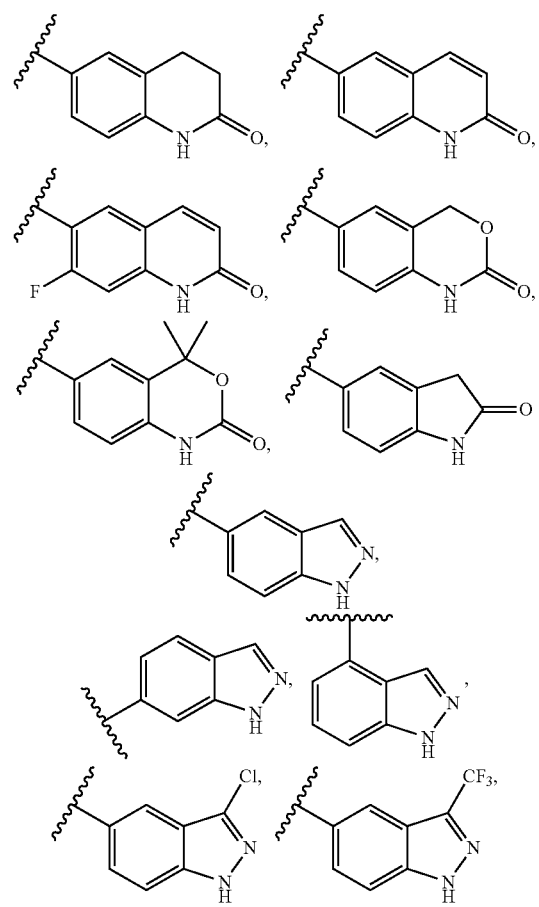

152
-continued

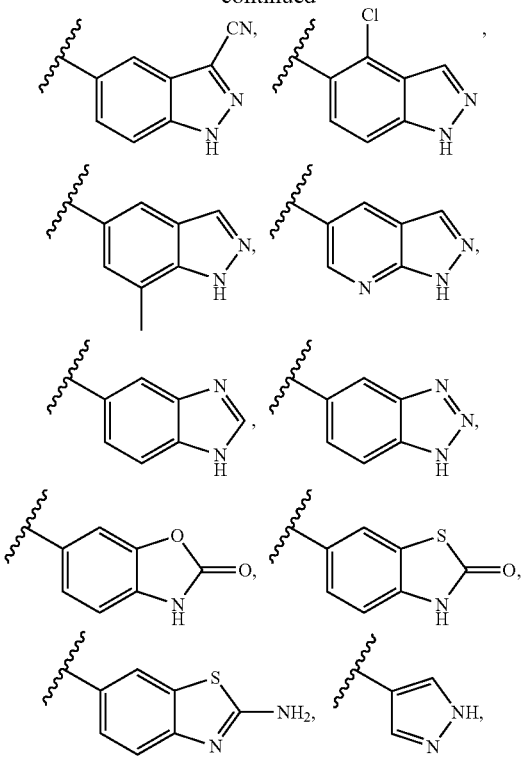

Ar³, ((thiazolyl)amino)phenyl, (pyrimidinyl)amino, or (pyrazolopyrimidinyl)amino;
R² is hydrogen, alkyl, or haloalkyl;
Ar¹ is phenyl or pyridinyl and is substituted with 0-3 substituents selected from halo, alkyl, alkoxy, haloalkoxy, and alkylSO₂;
Ar² is

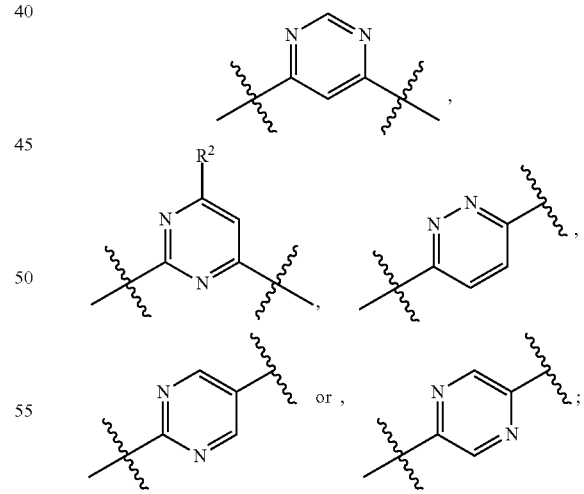

Ar³ is phenyl, pyridinyl, or pyridazinyl, and is substituted with 1 substituent selected from hydroxyl or NH₂—;
L¹ is a direct bond, or; and
L² is —O or —CH₂O—, —CH₂CH₂—CH₂CH₂—, —CH(CH₃)CH₂—, —CH₂CH(CH₃)—, —CH₂CH₂CH₂—, or cyclopropdiyl;
or a pharmaceutically acceptable salt thereof or a pharmaceutically acceptable salt thereof.

3. A compound of claim 2 where

R¹ is selected from the group consisting of

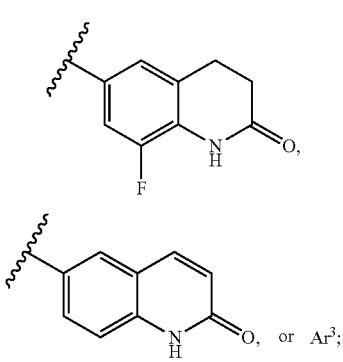

Ar¹ phenyl or pyridinyl and is substituted with 0-3 substituents selected from halo, alkyl, alkoxy, and haloalkoxy;

Ar³ is phenyl and is substituted with 1 hydroxy substituent;

L¹ is a direct bond or —CH₂—; and

L² is —CH₂O—;

or a pharmaceutically acceptable salt thereof.

4. A compound of claim 1 where R¹ is selected from the group consisting of

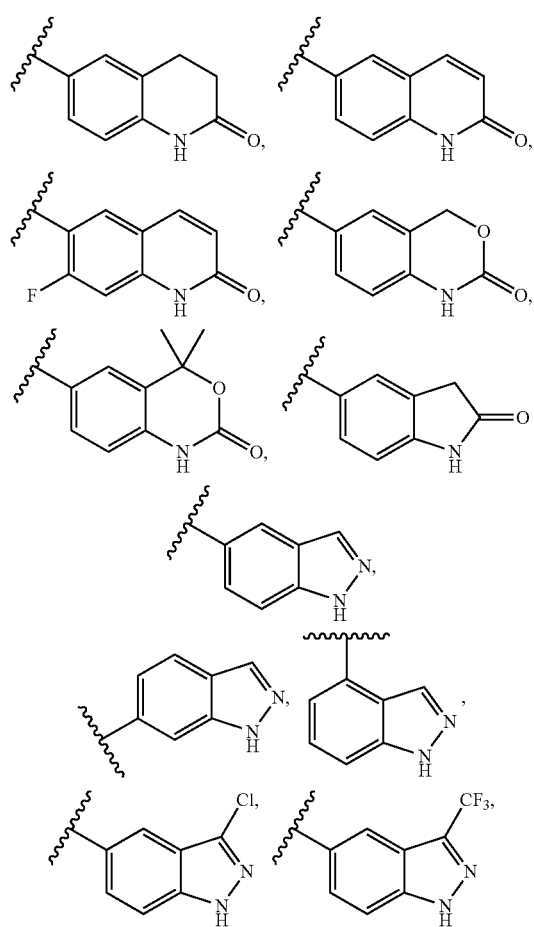

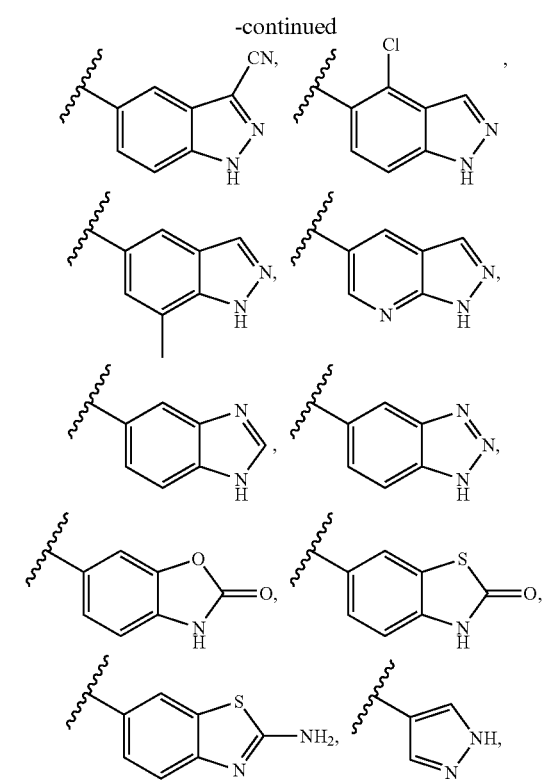

Ar³, ((thiazolyl)amino)phenyl, (pyrimidinyl)amino, or (pyrazolopyrimidinyl)amino; and Ar³ is phenyl, pyrimidinyl, or pyridazinyl, and is substituted with 1 substituent selected from hydroxy and NH₂—.

5. A compound of claim 1 where Ar² is

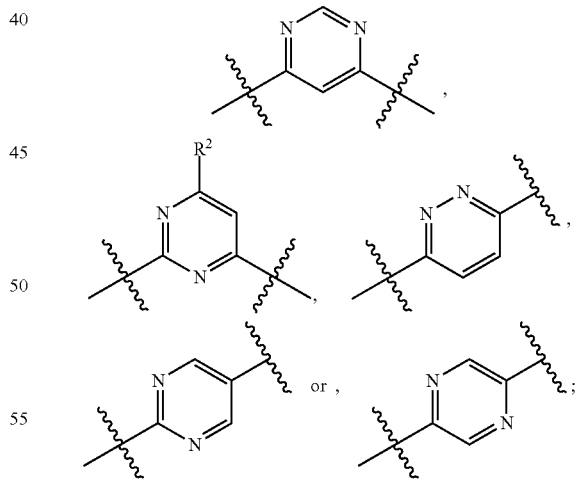

and

R² is hydrogen, alkyl, or haloalkyl.

6. A compound of claim 1 where L¹ is a direct bond, or —CH₂—; and L² is —O— or —CH₂O—; or a pharmaceutically acceptable salt thereof.

7. A pharmaceutical composition comprising a compound of claim 1 or a pharmaceutically acceptable salt thereof and a pharmaceutically acceptable carrier.

8. A method for the treatment of depression, neuropathic pain, or Parkinson's disease, which comprises administering to a patient a therapeutically affective amount of a compound of claim 1.

9. The method of claim 8 directed to the treatment of depression.

10. The method of claim 8 directed to the treatment of neuropathic pain.

* * * * *